US010525024B2

(12) United States Patent
Kadam

(10) Patent No.: US 10,525,024 B2
(45) Date of Patent: Jan. 7, 2020

(54) METHODS FOR RESCUING PHENOBARBITAL-RESISTANCE OF SEIZURES BY ANA-12 OR ANA-12 IN COMBINATION WITH CLP290

(71) Applicants: THE JOHNS HOPKINS UNIVERSITY, Baltimore, MD (US); KENNEDY KRIEGER INSTITUTE, INC., Baltimore, MD (US)

(72) Inventor: Shilpa D. Kadam, Pikesville, MD (US)

(73) Assignees: The Johns Hopkins University, Baltimore, MD (US); Kennedy Krieger Institute, Inc., Baltimore, MD (US)

(*) Notice: Subject to any disclaimer, the term of this patent is extended or adjusted under 35 U.S.C. 154(b) by 0 days.

(21) Appl. No.: 15/504,141

(22) PCT Filed: Aug. 14, 2015

(86) PCT No.: PCT/US2015/045170
§ 371 (c)(1),
(2) Date: Feb. 15, 2017

(87) PCT Pub. No.: WO2016/025778
PCT Pub. Date: Feb. 18, 2016

(65) Prior Publication Data
US 2017/0281579 A1  Oct. 5, 2017

Related U.S. Application Data

(60) Provisional application No. 62/037,654, filed on Aug. 15, 2014.

(51) Int. Cl.
| | |
|---|---|
| *A61K 31/4015* | (2006.01) |
| *A61K 31/501* | (2006.01) |
| *A61K 31/196* | (2006.01) |
| *A61K 45/06* | (2006.01) |
| *A61K 31/4166* | (2006.01) |
| *A61K 31/515* | (2006.01) |
| *A61K 31/553* | (2006.01) |
| *A61K 31/55* | (2006.01) |
| *A61K 38/08* | (2019.01) |

(52) U.S. Cl.
CPC ........ *A61K 31/196* (2013.01); *A61K 31/4015* (2013.01); *A61K 31/4166* (2013.01); *A61K 31/501* (2013.01); *A61K 31/515* (2013.01); *A61K 31/55* (2013.01); *A61K 31/553* (2013.01); *A61K 38/08* (2013.01); *A61K 45/06* (2013.01); *A01K 2207/20* (2013.01); *A01K 2207/30* (2013.01); *A01K 2267/0356* (2013.01)

(58) Field of Classification Search
CPC ............. A61K 2300/00; A61K 31/515; A61K 2207/20; A61K 2207/30; A61K 2267/0356; A61K 45/06; A61K 31/00; G01N 33/5058; C07K 14/705

See application file for complete search history.

(56) References Cited

U.S. PATENT DOCUMENTS

| | | | | |
|---|---|---|---|---|
| 7,709,207 | B2* | 5/2010 | De Koninck | .......... A61K 31/00 |
| | | | | 435/6.16 |
| 8,173,376 | B2* | 5/2012 | De Koninck | .......... A61K 31/00 |
| | | | | 435/6.1 |
| 8,734,807 | B1 | 5/2014 | Langlois-Rahme | |
| 9,415,028 | B2* | 8/2016 | Ben-Ari | ............... A61K 31/196 |
| 9,592,214 | B2* | 3/2017 | Ben-Ari | ............... A61K 31/196 |
| 2007/0043034 | A1 | 2/2007 | Staley et al. | |
| 2007/0092510 | A1* | 4/2007 | De Koninck | .......... A61K 31/00 |
| | | | | 424/143.1 |
| 2008/0260644 | A1 | 10/2008 | Cohen | |
| 2010/0330586 | A1* | 12/2010 | De Koninck | .......... A61K 31/00 |
| | | | | 435/7.1 |
| 2012/0052075 | A1 | 3/2012 | Pedersen et al. | |
| 2012/0115919 | A1 | 5/2012 | Mueller et al. | |
| 2012/0252894 | A1* | 10/2012 | Rashid | ................. A61K 31/195 |
| | | | | 514/562 |
| 2013/0022622 | A1* | 1/2013 | Ben-Ari | ............... A61K 31/196 |
| | | | | 424/172.1 |
| 2014/0080910 | A1* | 3/2014 | Ben-Ari | ............... A61K 31/196 |
| | | | | 514/562 |

(Continued)

FOREIGN PATENT DOCUMENTS

| | | |
|---|---|---|
| WO | 2004101072 A1 | 11/2004 |
| WO | 2007056510 A2 | 5/2007 |

(Continued)

OTHER PUBLICATIONS

Johns Hopkin treatment for epilepsy retrieved from the Johns hopkin medicine library website: www.hopkinsmedicine.org/healthlibrary/conditions/nervous_system_disorders/refractory_epilepsy_135,5 on Mar. 29, 2018.*
French. Epilepsy Curr. 2006; 6:177-180.*
Kwan et al. Epilepsy 2009; 50:57-62.*
Kang et al., Austin. J. Cerebrovasc. Dis. Stroke. 2014: 1: 1-11.*
Alberi, L., et al., (2010) "Neonatal stroke in mice causes long-term changes inneuronal Notch-2 expression that may contribute to prolonged injury", Stroke, vol. 41, Suppl. 1, pp. S64-S71.
Wang, Y., et al., (2006) "Hypoxic-ischemic brain injury in the neonatal rat model: relationship between lesion size at early MR imaging and irreversible infarction", American Journal of Neuroradiology, vol. 27, pp. 51-54.
Traa, B., et al., (2008) "Gabapentin neuroprotection and seizure suppression in immature mouse brain ischemia", Pediatric Research, vol. 64, No. 1, pp. 81-85.

(Continued)

Primary Examiner — Chang-Yu Wang
(74) Attorney, Agent, or Firm — Johns Hopkins Technology Ventures

(57) ABSTRACT

The present invention relates to the field of seizures. More specifically, the present invention provides compositions and methods for treating refractory seizures in neonates. In one embodiment, the method comprises the steps of (a) administering to the patient an amount of a KCC2 agonist and/or trkB antagonist effective to restore KCC2 expression to normal physiological levels; and (b) administering to the patient an effective amount of an anti-seizure medication.

2 Claims, 25 Drawing Sheets

(56) References Cited

U.S. PATENT DOCUMENTS

| | | | | |
|---|---|---|---|---|
| 2015/0335600 | A1* | 11/2015 | Ben-Ari | A61K 38/11 424/94.1 |
| 2016/0312229 | A1* | 10/2016 | Cancedda | A61K 31/64 |

FOREIGN PATENT DOCUMENTS

| | | |
|---|---|---|
| WO | 2009097695 A1 | 8/2009 |
| WO | 2009114950 A1 | 9/2009 |
| WO | 2010132999 A1 | 11/2010 |
| WO | 2011103471 A1 | 8/2011 |
| WO | 2014076235 A1 | 5/2014 |

OTHER PUBLICATIONS

Comi, A., et al., (2009) "Impact of age and strain on ischemic brain injury and seizures after carotid ligation in immature mice", International Journal of Developmental Neuroscience, vol. 27, pp. 271-277.

Comi, A., et al., (2004) "A new model of stroke and ischemic seizures in the immature mouse", Pediatric Neurology, vol. 31, No. 4, pp. 254-257.

Boulle et al., "TrkB inhibition as a therapeutic target for CNS-related disorders." Prog Neurobiol. Aug. 2012;98(2):197-206.

Cazorla et al., "Identification of a low-molecular weight TrkB antagonist with anxiolytic and antidepressant activity in mice." J Clin Invest. May 2011;121(5):1846-57.

Constandil et al.,Cyclotraxin-B, a New TrkB Antagonist, and Glial Blockade by Propentofylline, Equally Prevent and Reverse Cold Allodynia Induced by BDNF or Partial Infraorbital Nerve Constriction in Mice. 13(6) J. Pain 579-89 (2012).

Dzhala et al., NKCC1 transporter facilitates seizures in the developing brain. Nat Med. Nov. 2005;11(11):1205-13. Epub Oct. 9, 2005.

Flemming et al., Chloride extrusion alleviates neuropathic pain. Nature Reviews Drug Discovery 12, 906 (2013).

Gagnon et al., Chloride extrusion enhancers as novel therapeutics for neurological diseases. Nat Med. Nov. 2013;19(11)1524-8.

Glykys et al., Differences in cortical versus subcortical GABAergic signaling: a candidate mechanism of electroclinical uncoupling of neonatal seizures. Neuron. Sep. 10, 2009;63(5):657-72.

Harrison et al., Mood disorders: Small-molecule neurotrophin antagonist reduces anxiety. Nat Rev Drug Discov. Jun. 2011;10(6):415.

Kadam et al., Functional integration of new neurons into hippocampal networks and poststroke , comorbidities following neonatal stroke in mice. 18 Epilepsy Behav. 344-57 (2010).

Kang et al., Age-andsex-dependentsusceptibilitytophenobarbital-resistantneonatalseizures:roleofchlorideco-transporters. 9 Frontiers Cellularneurosci. Art. 173 (2015).

Khanna et al., Limitations of Current GABA Agonists in Neonatal Seizures: Toward GABA Modulation via the Targeting of Neuronal Cl(−) Transport . . . Front Neurol. Jun. 25, 2013;4:78.

Khirug et al., A single seizure episode leads to rapid functional activation of KCC2 in the neonatal rat hippocampus. J Neurosci. Sep. 8, 2010;30(36):12028-35.

Loscher et al., Cation-chloride cotransporters NKCC1 and KCC2 as potential targets for novel antiepileptic and antiepileptogenic treatments. Neuropharmacology. Jun. 2013;69:62-74.

Murguia-Castillo et al., NKCC1 and KCC2 protein expression is sexually dimorphic in the hippocampus and entorhinal cortex of neonatal rats. Neurosci Lett. Sep. 27, 2013;552:52-7.

Nardou et al., Mechanisms and effects of seizures in the immature brain. Semin Fetal Neonatal Med. Aug. 2013;18(4):175-84.

Puskarjov et al., Pharmacotherapeutic targeting of cation-chloride cotransporters in neonatal seizures. Epilepsia vol. 55, Issue 6, pp. 806-818, Jun. 2014.

Pukarjov et al., BDNF is required for seizure-induced but not developmental up-regulation of KCC2 in the neonatal hippocampus. 88 Neuropharmacology 103-09 (2015).

Uvarov et al., A Novel N-terminal Isoform of the Neuron-specific K-Cl Cotransporter KCC2. (2007) Journal of Biological Chemistry. 282(42):30670-30576.

Vassoler et al., Epigenetic Inheritance of a Cocaine Resistance Phenotype. Nat Neurosci. Jan. 2013; 16(1):42-47.

Valentino et al., "Transcranial Direct Current Stimulation for Treatment of Freezing of Gait: A cross-over Study", Movement Disorders, vol. 29, No. 8, 2014.

* cited by examiner

METHODS FOR RESCUING PHENOBARBITAL-RESISTANCE OF SEIZURES BY ANA-12 OR ANA-12 IN COMBINATION WITH CLP290

CROSS-REFERENCE TO RELATED APPLICATIONS

This application is a 35 U.S.C. § 371 U.S. national entry of International Application PCT/US2015/045170, having an international filing dates Aug. 14, 2015, which claims the benefit of U.S. Provisional Application No. 62/037,654, filed Aug. 15, 2014, the content of each of the aforementioned applications is herein incorporated by reference in its entirety.

STATEMENT OF GOVERNMENTAL INTEREST

This invention was made with government support under grant no. R21HD073105, awarded by the National Institutes of Health. The government has certain rights in the invention.

FIELD OF THE INVENTION

The present invention relates to the field of seizures. More specifically, the present invention provides compositions and methods for treating refractory seizures in neonates.

BACKGROUND OF THE INVENTION

Detected in 1 to 3.5 per 1000 newborns, neonatal convulsions refer to the seizures occurring within the first 28 days of life. Neonatal seizures, if poorly managed, can result in severe neurodevelopmental outcomes that threaten cognition, motor function, and even life. The associated pathologies include, but are not limited to hypoxic-ischemic encephalopathy (HIE), stroke, intracranial hemorrhage, brain malformation, infarction, prenatal and neonatal infections. However, HIE has been the most prevalent cause of neonatal seizures, and the HIE-associated seizures pose a great challenge to its current therapy because those have higher propensity of showing a stubborn refractoriness to conventional antiepileptic drugs (AEDs) provided as a first-line therapy in clinics.

The refractoriness in neonatal seizures can be mainly attributed to a neuronal chloride gradient that does not generate hyperpolarization as much as the one established in the adult nervous system. When the ion channels located at neuronal membrane open, the net ion influx or efflux is determined by both electrical and chemical gradient: an electrical gradient of a certain threshold voltage that a neuron wants to maintain and a chemical gradient that is determined by the net concentration of ions at extracellular and intracellular environment. The mature nervous system maintains a relatively low intracellular chloride concentration such that an opening of chloride channels results in an influx of negatively charged chloride ions which ultimately renders a post-synaptic inhibition in central nervous system (CNS). In contrast, the immature nervous system has a relatively higher intracellular chloride concentration that results in less hyperpolarization or even depolarization in some cases. Hence, the HIE-associated neonatal seizures are not efficaciously modulated by conventional anti-convulsants, phenobarbital and phenytoin, that target $GABA_A$ receptors to open the chloride channels to induce neuronal hyperpolarization and halting seizures eventually. The difference in the chloride gradient also contributes to the neonatal hyperexcitability that leads to a higher seizure susceptibility observed in seizing neonates, especially in the first 2 days in the neonatal period.

The depolarizing chloride gradient has been shown to play a critical role in neurodevelopment such as neuronal migration, proliferation, and maturation. The critical switch of neuronal chloride gradient from depolarizing to hyperpolarizing occurs within neonatal period, and cation chloride co-transporters (CCCs) are one of the pivotal players that drive the neuronal chloride gradient toward its adult level. In early developmental stage, NKCC1 pumps in chloride ions into a neuron to build up a high intracellular chloride concentration which results in a depolarizing gradient necessary for the associated neurodevelopment. In the later development, KCC2 pumps out chloride ions to lower the intracellular chloride concentration which renders a hyperpolarizing gradient when the chloride channels are opened. KCC2 expression is neuron-specific[15] whereas NKCC1 expression is relatively ubiquitous, therefore the ratio of these two CCCs are critical for the efficacy of anti-convulsants that depend on chloride ion influx. The well-studied developmental profile of CCCs in human and rodents suggests: 1) the high expression level of NKCC1 during early development decreases throughout neonatal period, and stabilizes at the lowest level after neonatal period, 2) the lower expression of KCC2 during early development gradually increases throughout neonatal period, and stabilizes at the highest level by the end of adolescent stage. Thus, in seizing adults with fully matured KCC2 expression in mature CNS, the delivery of conventional $GABA_A$-modulating AEDs drives an ideal hyperpolarization driven by the chloride influx upon channel opening. However, in seizing neonates with lower KCC2 expression in a developing CNS, refractoriness to traditional AEDs is often observed. Importantly, KCC has a caudal-rostral expression pattern that the establishment of hyperpolarizing chloride gradient starts at the spinal cord, and reaches the brain at last. This relates to a neonate-specific phenomenon of electroclinical dissociation where a neonate undergoes electrographic seizures without behavioral manifestation.

Designing and investigating an efficient therapy for treating refractory neonatal seizures is challenging because there are intrinsic difficulties in dissociating the harmful effects of hypoxic-ischemia and seizures. Many animal models have been proposed to examine the refractory neonatal seizures that mimic HIE condition such as in vitro chemo-convulsive, in vivo hypoxic, and ischemic model. Ischemic models, with the highest clinical relevance among many HIE models, have provided a crucial insight on the role of CCCs in designing an optimal pharmacotherapy for refractory seizures in neonates. Recent animal studies have focused on targeting NKCC1 using Bumetanide, a potent NKCC1 blocker, to control refractory seizures. Under ischemia, an acute upregulation of NKCC1 expression occurs such that an increased chloride influx causes hyperexcitability and more refractoriness to conventional AEDs. Prevention of chloride influx by blocking NKCC1 with Bumetanide may establish a neuronal environment that enables $GABA_A$ modulating AEDs to act efficaciously upon an ischemic insult. However, more studies are needed to ensure: 1) the safety of Bumetanide in neonates as an adjunct therapy, and 2) the true additional efficacy of Bumetanide on refractory seizures. Indeed, chronic delivery of bumetanide may induce an overwhelming diuresis in neonates with HIE suffering other pathophysiological complications such as energy failure and altered homeostasis. Accordingly, new methods for treating neonatal seizures are needed.

BRIEF DESCRIPTION OF THE FIGURES

FIGS. 7Aa & 7Ab. Expanded time scale traces for time-points in A. Arrowheads denote the start and end of the ictal event. 7A1 & 7A2. Raw EEG trace in A filtered by high and low frequency band pass.

DETAILED DESCRIPTION OF THE INVENTION

Figure 1:
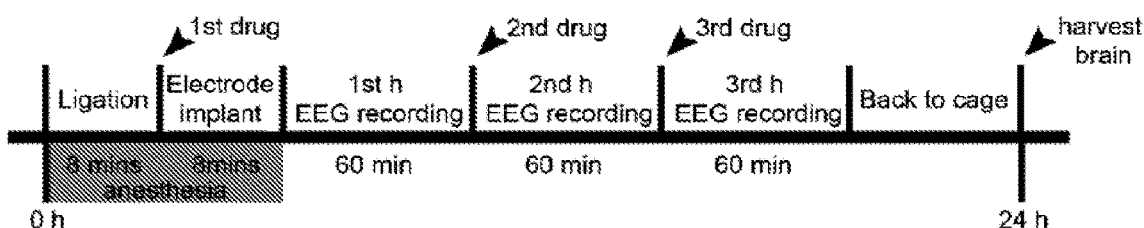
FIG. 1A-1D. Effect of ANA12+PB on the total seizure burden at P7 and P10. I. Schematics of the experimental design. Experimental paradigm for the acute ligation surgery and synchronous video-EEG recordings with the time-course of drug administrations and the durations for each procedure. Arrowheads indicate time-points of drug administration after carotid-ligation and brain-harvesting for 24 h WB data. II. A-D. Total time spent seizing on EEG was quantitated as seizure burden at P7 and P10 over a 3 h period, and was represented by bar graphs (black bar=baseline, gray=2nd h, and white=3rd h) A&C) vehicle (5% DMSO) and ANA12-alone treatment groups. The data from A&C were pooled to form a ligate-control group represented in B&D. B&D) ligate control vs. ANA12+PB+BTN. Within-group comparison was done using repeated measures ANOVA (i.e., *=p<0.05; =p<0.01; *=p<0.001). Brackets (@) denote significant between-group comparisons at each hour (independent sample t-tests; p<0.05).
Figure 1:
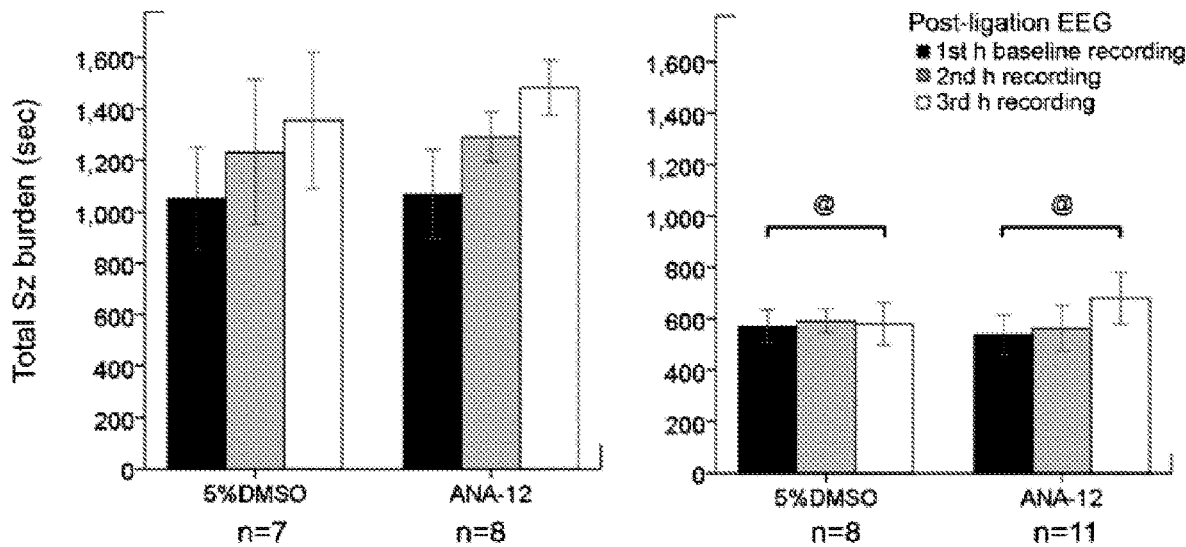
Figure 1:
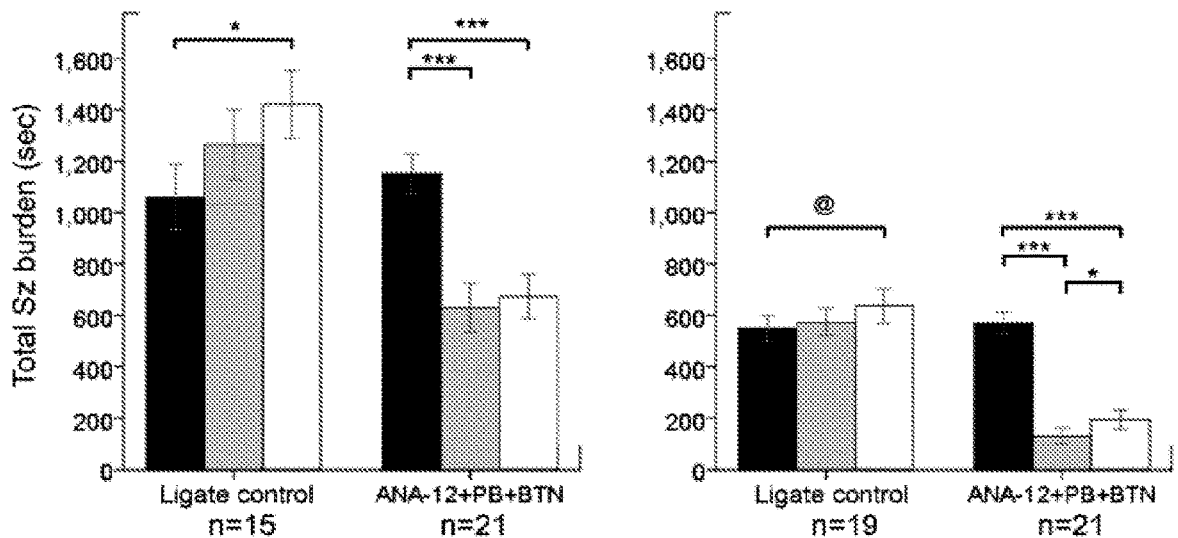

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The present invention is based, at least in part, on the discovery that refractory seizures can be treated using KCC2 agonists and/or trkB antagonists. More specifically, in particular embodiments, the present invention provides novel pharmaceutical interventions that enhance KCC2 function by using a KCC2 agonist and/or small molecule Trk-B receptor antagonists as adjunct therapies to convert phenobarbital (PB)-resistant seizures into phenobarbital responsive seizures in neonates. Both drugs act through very different mechanisms but achieve the same goal. They help enhance KCC2 activity in injured neonatal brains and thus, improve the outflow of chloride from neurons.

As described herein, the present inventors have shown that, unlike in adult brains, KCC2 expression in the neonatal brain is much lower and undergoes further down-regulation following an ischemic insult, which is one of the most common causes of neonatal seizures. Because it is the KCC2 activity on neuronal cell membranes that help reduce the intracellular Cl concentrations; the present inventors hypothesized that enhancing its activity in an injured/seizing neonatal brain will act as an effective adjunct treatment to convert PB-resistant seizures into PB-responsive seizures. The present inventors have shown that a Trk-B antagonist (ANA-12), when administered systemically to block the action of excessive BDNF release following ischemic injury in immature brains in conditions like ischemia, hypoxia, infection and inflammation, prevents the disruption of the normally increasing KCC2 expression profile and makes the refractory seizures responsive to PB. The present inventors have also achieved similar results with a KCC2 agonist, CLP290.

This discovery provides a novel approach to treat and prevent the emergence of refractory seizures in both neonates and adults. Additionally, by correcting the developmental dysfunction of ischemia related KCC2 downregulation, the present invention may prevent the emergence of long-term neurological morbidities in the form of ADHD, learning disabilities, autism spectrum disorders and psychiatric disorders associated with a history a neonatal CNS injury.

It has long been known that blocking Trk-B receptors may be able to prevent some deleterious downstream effects in neurological diseases (especially in pain research). However, the old generation of Trk-B receptors antagonists was incapable of crossing the blood brain barrier (BBB) and, therefore, clinical applicability remained elusive. The current generation of small molecule antagonists have been shown to be able to cross the BBB and therefore systemic application during periods of acute CNS injury are now feasible and are a novel approach to treat conditions where KCC2 down-regulation plays a role in neurological pathogenesis. The present inventors have identified a novel mechanism of seizure refractoriness in neonatal ischemic seizures that involves the reduction and delay in the developmental profile of KCC2 up-regulation that is important to developing brains. This acute down-regulation and severe attenuation of KCC2 function may underlie both the acute symptoms but also the appearance of long-term morbidity due to the dysfunctional period in early brain development. The novel approach of enhancing KCC2 function using KCC2 agonists and/or Trk-B receptor antagonists would be a short, acute systemic (i.e., non-CNS-invasive) intervention that would help better treat the acute symptoms where current line of treatments are found non-efficacious but more importantly prevent future morbidities involving the brain by preventing disruption of early developmental processes.

Examples of KCC2 agonists include, but are not limited to, N-ethylmaleimide (NEM), the chloride channel inhibitor 5-nitro-2-(3-phenylpropylamino) benzoic acid (NPPB), CLP257, CLP290 and analogs, functional derivatives and prodrugs thereof. Examples of KCC2 agonists are described in WO2009/114950, WO2009/097695 and WO2010132999.

Specific examples of trkB antagonists include, but are not limited to, ANA-12 (Cazorla et al., 121(5) J. CLIN. INVEST. 1846-57 (2011)); N-T19 (Cazorla et al. (2011)); K252a; and cyclotraxin-B (CTX-B) (Constandil et al., 13(6) J. PAIN 579-89 (2012)).

As used herein, the term "modulate" indicates the ability to control or influence directly or indirectly, and by way of non-limiting examples, can alternatively mean inhibit or stimulate, agonize or antagonize, hinder or promote, and strengthen or weaken. Thus, the term "modulator" refers to an agent that modulates KCC2 and/or trkB. Modulators may be organic or inorganic, small to large molecular weight individual compounds, mixtures and combinatorial libraries of inhibitors, agonists, antagonists, and biopolymers such as peptides, nucleic acids, or oligonucleotides. A modulator may be a natural product or a naturally-occurring small molecule organic compound. In particular, a modulator may be a carbohydrate; monosaccharide; oligosaccharide; polysaccharide; amino acid; peptide; oligopeptide; polypeptide; protein; receptor; nucleic acid; nucleoside; nucleotide; oligonucleotide; polynucleotide including DNA and DNA fragments, RNA and RNA fragments and the like; lipid; retinoid; steroid; glycopeptides; glycoprotein; proteoglycan and the like; and synthetic analogues or derivatives thereof, including peptidomimetics, small molecule organic compounds and the like, and mixtures thereof. A modulator identified according to the invention is preferably useful in the treatment of a disease disclosed herein.

As used herein, an "antagonist" is a type of modulator and the term refers to an agent that can, directly or indirectly, block, suppress or reduce one or more functions or biological activities of the target. An "agonist" is a type of modulator and refers to an agent that, directly or indirectly, can activate, stimulate or increase one or more functions or biological activities of the target.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies.

The terms "specifically binds to," "specific for," and related grammatical variants refer to that binding which occurs between such paired species as antibody/antigen, enzyme/substrate, receptor/agonist, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

Optional" or "optionally" means that the subsequently described event or circumstance can or cannot occur, and that the description includes instances where the event or circumstance occurs and instances where it does not.

The terms "subject," "individual," or "patient" are used interchangeably herein, and refer to a mammal, particularly, a human. In certain embodiments, the patient is an adult and/or a neonate. In particular embodiments, the patient suffers from seizures.

As used herein, the term "effective," means adequate to accomplish a desired, expected, or intended result. More particularly, a "therapeutically effective amount" as provided herein refers to an amount of a KCC2 and/or trkB modulator of the present invention, either alone or in combination with another therapeutic agent, necessary to provide the desired therapeutic effect, e.g., an amount that is effective to prevent, alleviate, or ameliorate symptoms of a condition. In a specific embodiment, the term "therapeutically effective amount" as provided herein refers to an amount of a KCC2 agonist and/or trkB antagonist, necessary to provide the desired therapeutic effect, e.g., an amount that is effective to prevent, alleviate, or ameliorate symptoms of seizures, e.g., refractory seizures. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

As used herein, the terms "treatment," "treating," and the like, refer to obtaining a desired pharmacologic and/or physiologic effect. The effect may be prophylactic in terms of completely or partially preventing a disease, condition or symptom thereof and/or may be therapeutic in terms of a partial or complete cure for a disease or condition and/or adverse effect attributable to the disease or condition. "Treatment," as used herein, covers any treatment of a disease or condition in a subject, particularly in a human, and includes: (a) preventing the disease or condition from occurring in a subject which may be predisposed to the disease or condition but has not yet been diagnosed as having it; (b) inhibiting the disease or condition, i.e., arresting its development; and (c) relieving the disease or condition, e.g., causing regression of the disease or condition, e.g., to completely or partially remove symptoms of the disease or condition.

A "trkB antagonist" refers to an agent that is able to block, suppress or reduce (including significantly) trkB biological activity, including downstream pathways mediated by trkB signaling, such as binding of trkB to BDNF or NT-4/5 and/or elicitation of a cellular response to BDNF or NT-4/5. The term "antagonist" implies no specific mechanism of biological action whatsoever, and is deemed to expressly include and encompass all possible pharmacological, physiological, and biochemical interactions with trkB whether direct or indirect, or whether interacting with BDNF, NT-4/5, trkB, or through another mechanism, and its consequences which can be achieved by a variety of different, and chemically divergent, compositions. Exemplary trkB antagonists include, but are not limited to, an anti-BDNF antibody, an anti-NT-4/5 antibody, a BDNF or an NT-4/5 inhibitory compound, a BDNF or an NT-4/5 structural analog, a dominant-negative mutation of a trkB receptor that binds BDNF and/or NT-4/5, a trkB immunoadhesin, an anti-trkB antibody, and a trkB inhibitory compound. For purpose of the present invention, it will be explicitly understood that the term "antagonist" encompass all the previously identified terms, titles, and functional states and characteristics whereby the trkB receptor itself, a trkB biological activity or the consequences of the biological activity, are substantially nullified, decreased, or neutralized in any meaningful degree.

"Biological activity" of trkB receptor generally refers to the ability to bind BDNF and NT-4/5 and/or activate trkB receptor signaling pathways. Without limitation, a biological activity includes any one or more of the following: the ability to bind its ligand BDNF and/or NT-4/5; the ability to dimerize and/or autophosphorylate after the ligand binding; the ability to activate the trkB signaling pathway; the ability to promote cell differentiation, proliferation, survival, growth and other changes in cell physiology, including (in the case of neurons, including peripheral and central neuron) change in neuronal morphology, synaptogenesis, synaptic function, neurotransmitter and/or neuropeptide release and regeneration following damage.

Accordingly, in one aspect, the present invention provides compositions and methods for treating refractory seizures in a neonatal patient. In one embodiment, the method comprises the steps of (a) administering to the patient an effective amount of a KCC2 agonist and/or trkB antagonist; and (b) administering to the patient an effective amount of an anti-seizure medication. In certain embodiments, the amount of a KCC2 agonist and/or trkB antagonist is effective to restore KCC2 expression to normal physiological levels. In particular embodiments, the seizure is an ischemia-related seizure. The KCC2 agonist can be, but is not limited to, N-ethylmaleimide (NEM), the chloride channel inhibitor 5-nitro-2-(3-phenylpropylamino) benzoic acid (NPPB), CLP257, or CLP290. In a specific embodiment, the KCC2 agonist is CLP290. The trkB antagonist can be, but is not limited to, ANA-12, N-T19, K252a or cyclotraxin-B. In a specific embodiment, the trkB antagonist is ANA-12. In particular embodiments, the anti-seizure medication is phenobarbital or phenytoin.

The present invention also provides a method for treating refractory seizures in a neonatal patient comprising the steps of (a) administering to the patient an amount of ANA-12 and/or CLP290 effective to restore KCC2 expression to normal physiological levels; and (b) administering to the patient an effective amount of an anti-seizure medication. In a specific embodiment, the seizure is an ischemia-related seizure. In other embodiments, the anti-seizure medication is phenobarbital (PB) or phenytoin.

In particular embodiments, the present invention provides methods and compositions for reducing the loading dose of PB required as first line treatment for neonatal seizures. The first loading dose is often ineffective in >50% of cases. Higher and repeated doses of PB can be detrimental for immature brains both acutely and in the long-term with associated cell death. In a further embodiment, a method for treating refractory seizures in a neonatal patient comprises the steps of (a) administering to the patient an amount of ANA-12 and/or CLP290 effective to restore KCC2 expression to normal physiological levels; and (b) administering to the patient an effective amount of phenobarbital. In methods comprising the use of CLP290 or any KCC2 agonist or trkB antagonist that shows some anti-seizure effects by itself, the effective amount of the anti-seizure medication or phenobarbital is reduced due to anti-seizure activity of CLP290.

In yet another embodiment, a method for treating refractory seizures in a patient comprises the steps of (a) administering to the patient an effective amount of an agent that increases KCC2 expression back to normal levels, wherein the seizure downregulates KCC2 expression; and (b) administering to the patient an effective amount of an anti-seizure medication. In particular embodiments, the patient is a neonate. In certain embodiments, the neonate is administered a transient dose of an anti-seizure medication. The present invention also provides a method for treating ischemia-related seizures in a neonatal patient comprising the steps of (a) administering a KCC2 agonist and/or a trkB antagonist in an amount(s) effective to restore KCC2 expression back to normal physiological levels; and (b) administering a transient dose of an anti-seizure medication in an amount effective to stop the seizures.

The compositions of the present invention can comprise an effective amount of a KCC2 agonist and an anti-seizure medication. In other embodiments, the compositions can comprise an effective amount of a trkB antagonist and an anti-seizure medication. In certain embodiments, the compositions can comprise an effective amount of a KCC2 agonist, a trkB antagonist and an anti-seizure medication. In a specific embodiment, a composition comprises ANA-12 and PB. In another embodiment, a composition comprises CLP290 and PB. In further embodiments, a composition comprises ANA-12, CLP290 and PB.

Typically, a loading dose of PB for a neonate comprises 15-25 mg/kg and additional doses of 5-10 mg/kg can be given if seizures are not controlled. The maximum loading dose is typically about 40 mg/kg. The effective amount of administered PB can be reduced by combining with a KCC2 agonist and/or trkB antagonist (co-administered or PB following KCC2 agonist and/or trkB antagonist administration) (particularly in embodiments in which CLP290 is used). The compositions of the present invention can comprise a lower amount of PB than is typically used. For example the dose of PB can comprise about 5-90% less than the typical dose for neonates including, but not limited to, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% less than a typical PB dose. The dose of PB can comprise about 5-90%, 10-85%, 15-75%, 20-70%, 25-65%, 30-60%, 35-55%, 40-50% less than the typical PB dose. In specific embodiments, a composition can comprise an amount of PB equivalent to about 1, 2, 3, 4, 5, 6, 7, 8, 9, 10, 11, 12, 13, 14, 15, 16, 17, 18, 19, or 20 mg/kg. In other embodiments, phenytoin can be used and the effective amount reduced accordingly as recited above.

In another aspect, the present invention provides compositions and methods for making a rodent ischemic seizure model. In one embodiment, a method for making a rodent ischemic seizure model comprises the steps of (a) anesthetizing the rodent; (b) permanently double ligating the right common carotid artery; and (c) closing the outer skin of the rodent. In particular embodiments, the rodent is a mouse. In a more specific embodiment, the mouse is a CD1 mouse. The rodent can be any species/strains that can be manipulated using the present methods to provide an ischemia only seizure background, as opposed to other strains that require ischemia and a 90 minute low oxygen hypoxia to generate a similar insult. In certain embodiments, the present invention provides a rodent ischemic seizure model produced by the methods described herein.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Acute Trk-β Inhibition Rescues Phenobarbital-Resistant Seizures in a Mouse Model of Neonatal Ischemia Neonatal seizures are commonly associated with hypoxic-ischemic encephalopathy (HIE). Phenobarbital (PB)-resistance is common and poses a serious challenge in clinical management. Using a newly characterized neonatal mouse model of ischemic seizures, this study investigated a novel strategy to rescue PB-resistance. A small-molecule TrkB antagonist, ANA12, used to selectively and transiently block post-ischemic BDNF-TrkB signaling in vivo determined whether rescuing TrkB-mediated post-ischemic degradation of KCC2 rescued PB-resistant seizures. The anti-seizure efficacy of ANA12+PB was quantitated by; 1) electrographic seizure burden using acute continuous video-EEGs and 2) post-treatment expression levels of KCC2 and NKCC1 using western blot analysis in postnatal day 7 and 10 (P7, P10) CD1 pups with unilateral carotid ligation. ANA12 significantly rescued PB-resistant seizures at P7, and improved PB-efficacy at P10. Single dose of ANA12+PB prevented the post-ischemic degradation of KCC2 up to 24 h. As anticipated, ANA12 by itself had no anti-seizure properties and was unable to prevent KCC2 degradation at 24 h without follow-on PB. This indicates that unsubdued seizures can independently lead to KCC2 degradation by non-TrkB dependent pathways. This study, for the first time, reports the potential therapeutic value of KCC2 modulation for the management of PB-resistant seizures in neonates.

Introduction

The neonatal period is a critical window for the increased occurrence of seizures, with a prevalence of 1 to 3.5 per 1000 newborns. Neonatal seizures, acquired from diverse pathologies, are associated with severe morbidity and mortality. Hypoxic-ischemic encephalopathy (HIE) accounts for 50-60% of the cases for neonatal seizures. HIE-associated seizures in neonates are known for their resistance to the conventional 1st-line anti-seizure drugs. GABAA agonists like phenobarbital (PB) and benzodiazepines, which are consistently efficacious in adults, fail as anti-seizure agents in neonates. Viable alternative strategies in overcoming these hurdles are currently lacking.

The pharmaco-resistance of 1st-line GABAA agonists in immature brains has been largely attributed to the developmental physiology of [Cl−]i that is 20-40 mM higher in immature neurons than in mature neurons. The age-dependent upregulation of K+Cl− co-transporter (KCC2), operating as a Cl− extruder in an electroneutral manner, has been shown to play a critical role in the shift of GABAergic signaling from depolarizing to hyperpolarizing. The expression of KCC2, which is predominantly neuronal, increases exponentially with conceptional age, especially perinatally, starting in the second half of gestation in humans to reach the significantly higher and stable adult levels. Similar developmental profiles for KCC2 have been noted in mice from the age of P3 to P15 where P7 is considered as term. Recent findings in both pre-clinical and human studies highlighting the important role of KCC2 in excitotoxicity have helped shape our novel strategy of modulating KCC2 to improve the efficacy of GABAA agonists in neonatal seizures.

The activation of BDNF-TrkB signaling has been associated with KCC2 downregulation in diverse pathological environments associated with excitotoxicity. Despite this known causal-effect relationship of BDNF-TrkB activation associated with degradation of KCC2, the novel strategy of preventing post-ischemic degradation of KCC2 by using a TrkB antagonist has never been tested in vivo. This may have primarily been due to the inability of old-generation TrkB antagonists to cross blood brain barrier and remain proteolytically stable. The identification of a small-molecule TrkB antagonist, ANA12, that can selectively block BDNF-TrkB binding directly at the extracellular domain of TrkB receptor in a non-competitive manner, allowed to test the following hypotheses: 1. Blocking BDNF-TrkB pathway after the onset of ischemia will prevent the post-ischemic degradation of KCC2; 2. If KCC2 degradation following ischemia results in the emergence of PB-resistant seizures, preventing KCC2 degradation will rescue the emergence of PB-resistance by maintaining KCC2 expression and function. This study investigated the following "proof-of-concept" question: Can the age-dependent PB-resistance for P7 seizures in a mouse model of neonatal ischemic seizures be reversed by a small-molecule TrkB antagonist? Does adding a NKCC1 antagonist, BTN, help improve this rescue?

Materials and Methods

Study approval. All experimental procedures were conducted in compliance with guidelines by the Committee on the Ethics of Animal Experiments, Johns Hopkins University (Permit Number: A3272-01) and all protocols were approved by the Animal Care and Use of Committee (IACUC) of Johns Hopkins. All litters of CD1 mice with dams were purchased from Charles River Laboratories Inc. (Wilmington, Mass.). Newly born litters of pups were delivered at postnatal 3 days old (P3) and were allowed to acclimate. Food and water were provided ad libitum. Equal numbers of male and female pups were introduced into the study. The number of pups and litters used in this study are listed in Table 2.

TABLE 2

Sample sizes for sham and ligated pups for each age group for EEG and histology experiments.

| | Age | | P7 | P10 | P12 | Sum |
|---|---|---|---|---|---|---|
| EEG | Sham | | 5 | 4 | 3 | 12 |
| | Ligated | Untreated | 9 | 8 | 9 | 26 |
| | Ligated | PB + BTN | 20 | 16 | 18 | 54 |
| | | Sum | 34 | 28 | 30 | 92 |
| P18 Histology: CV stain | | | 15 | 15 | 19 | 49 |

Surgical procedure for ischemic insult and sub-dermal EEG electrode implantation.

The surgical protocol was similar to the previously published work (Kang et al., 9 FRONTIERS CELLULAR NEUROSCI. Art. 173 (2015); Kadam et al., 18 EPILEPSY BEHAV. 344-57 (2010)). At P7 or P10, animals were subjected to permanent unilateral ligation of right common carotid artery using 6-0 surgisilk (Fine Science Tools, BC Canada) under isoflurane anesthesia. The outer skin was closed with 6-0 monofilament nylon (Covidien, MA), and lidocaine was applied as an additional local anesthetic. Under continued anesthesia, animals were then implanted with 3 sub-dermal EEG scalp electrodes: 1 reference, 1 ground, and 1 recording overlying the parietal cortex. Wire electrodes made for use in humans (IVES EEG; Model # SWE-L25-MA, USA) were implanted sub-dermally and fixed in position with adhesive. Pups were then allowed to recover from anesthesia which took a couple of minutes. Finally, animals were tethered to a preamplifier by connecting sub-dermal electrodes within a recording chamber for 3 h of video-EEG, maintained at 36° C. with isothermal pads. At the end of the recording session, the animals were returned to the dam after removal of the sub-dermal electrodes. The average duration of anesthesia for both ligation and electrode implantation in this study added up to 16.18±4.37 min. There is a known mortality rate of ~10-20% associated with the surgical procedure of carotid-ligation and severe seizures in the model. The mortality rates for the pups 24 h after surgery were n/n=9/45 (20%) pups at P7 (6 males and 3 females) and n/n=7/52 (13%) pups at P10 (3 males and 4 females), and were not significantly different, by age nor by sex in this study ($p=0.42$ and $p=0.57$ respectively; Fisher's exact test, two-tailed). Mortality rates following the surgical procedure were also not significantly different by treatment (ligated control vs. treated group; $p=0.26$).

Figure 3:
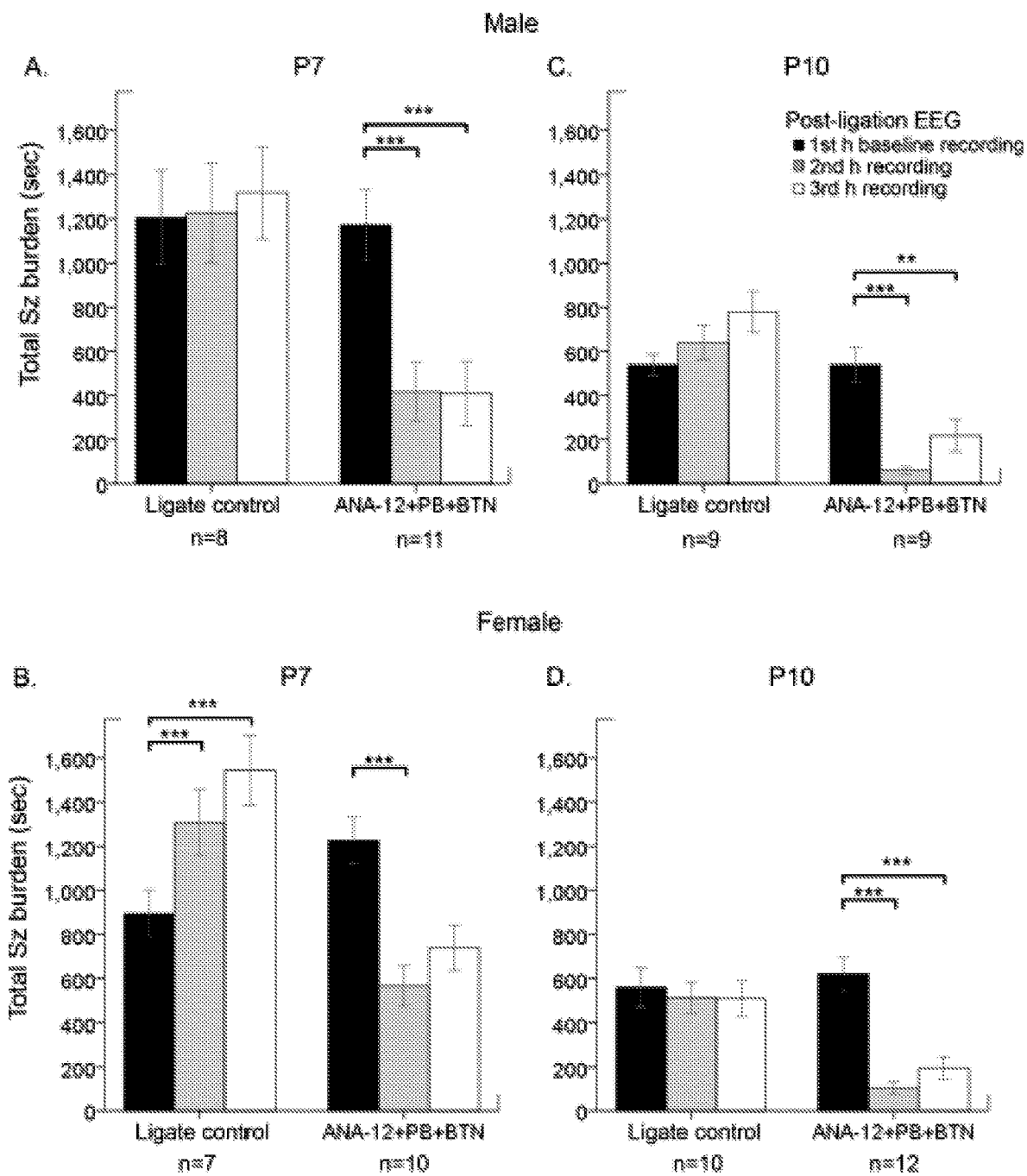
FIG. 3A-3D. The anti-seizure efficacy of ANA12+PB was not different by sex. The efficacy of ANA12+PB on total seizure burden was evaluated by sex at P7 and P10. A&C. Males at both ages of P7 and P10 responded significantly to ANA12+PB. However, at P10, BTN administration following PB weakened the statistical significance of seizure suppression achieved by PB. B&D. ANA12+PB efficacy was significant in females at both P7 and P10. Additionally, a significant temporal increase in the total seizure burden over time-course of 3 h period was detected in P7 females, but was absent in P7 males. At P7, BTN aggravated PB-subdued seizures in females such that PB-efficacy was lost. ANA12+PB efficacy was not significantly different between males and females. (Repeated measures ANOVA; *=p<0.05; =p<0.01; *=p<0.001).

Experimental paradigm. Following unilateral permanent carotid-ligation, vehicle [5% dimethyl sulfoxide (DMSO)], ANA12 (2.5 mg/kg; N-[2-[[(Hexahydro-2-oxo-1H-azepin-3-yl) amino] carbonyl] phenyl] benzo[b]thiophene-2-carboxamide), or 0.9% sodium chloride (Saline) was injected intraperitoneally (IP). The general outline of the experimental paradigm is depicted in FIG. 1 (top panel, I). Pups were randomly assigned to three different treatment regimens over the 3 h acute and continuous EEG recording period: 1) vehicle+saline+saline, 2) ANA12+saline+saline, and 3) ANA12+PB+BTN. Injection of 1st drug occurred immediately after ligation, and the subsequent injections followed every hour (i.e.; FIGS. 1, II B&D). Each color in the bar graphs (FIGS. 1&3) represents the parameters (i.e.; total EEG seizure burdens) quantitated for the 60 min duration of EEG recordings during each hour: 1st h (black bars), 2nd h (gray bars), and 3rd h (white bars).

The vehicle, 5% DMSO (Cat. No. 472301) was made in phosphate buffered saline (v/v; pH 7.4). ANA12 (2.5 mg/kg) was dissolved in the vehicle. ANA12 was stored at −20° C. in aliquots ready for use (Sigma-Aldrich; Cat. No. SML0209). PB was (25 mg/kg: Sigma-Aldrich; Cat. No. P5178) dissolved in phosphate buffered saline (made on the day of experiment) injection followed 1 h after the vehicle or ANA12 injection, and BTN injection [0.1-0.2 mg/kg dissolved in 100% alcohol; aliquoted and stored at −20° C.; protocol similar to Example 2 below (Kang et al. (2015)] followed 1 h after PB injection.

In vivo synchronous video-EEG recording and analyses. EEG recording was acquired using Sirenia Acquisition software (v 1.6.4) with synchronous video capture (Pinnacle Technology Inc. KS, USA). Data acquisition was done with sampling rates of 400 Hz that had a pre-amplifier gain of 100 and the filters of 1 Hz high-pass and 60 Hz low-pass to remove ambient noise. The data were scored by binning the raw EEG trace in 10 sec epochs. Similar to Example 2 (Kang et al., 2015), seizures were defined as electrographic ictal events that consisted of rhythmic spikes of high amplitude, diffuse peak frequency of ≥7-8 Hz (i.e.; peak frequency detected by automated spectral power analysis) lasting ≥6 seconds. Short duration burst activity lasting <6 seconds (brief runs of epileptiform discharge) was not included for seizure burden calculations in this study.

Western blot at 3 h and 24 h post-ligation. All animals were anesthetized with chloral hydrate (90 mg/ml; IP) before being transcardially perfused. The whole brains of P7 and P10 pups were harvested at either 3 h or 24 h post-ligation, and were frozen as ipsilateral and contralateral hemisphere. The brains were stored in −80° C. until further use. Homogenized whole brain lysates were suspended in cell lysis buffer with 10% protease/phosphatase inhibitor cocktail. Total protein concentrations were quantified through Bradford Assay (Bio-Rad) at 570 nm wavelength, and the samples were diluted for 50 ug of protein at 20 ul of loading volume for gel electrophoresis.

Samples were run on 4-20% gradient 1.5 mm 15 wells SDS gels (Invitrogen) for 100-120 min with 130V, and were transferred onto nitrocellulose membranes for overnight wet-transfer for minimum of 18 hours at 30V. After the transfer, the nitrocellulose membranes underwent 1 h blocking step in odyssey buffer, before overnight incubation in primary antibodies: rabbit α-KCC2 (1:1000, Millipore; Cat. No. 07-432); rabbit α-NKCC1 (1:500, Millipore, Cat. No. AB3560P); mouse α-actin (1:10000, LI-COR Biosciences, Cat. No. 926-42214). On the next day, nitrocellulose membranes were washed with TBS containing tween detergent, and then were incubated in chemiluminescence secondaries for 1 h (1:5000 for both goat α-mouse 680LT and goat α-rabbit 800CW, LI-COR Biosciences). Chemiluminescent protein bands were analyzed using the Odyssey infrared imaging system 2.1 (LI-COR Biosciences). The optical density of each protein sample was normalized to the actin bands run on each lane for internal control. The expression levels of the proteins of interest in ipsilateral hemispheres were normalized to the same in contralateral hemispheres for each pup. The human brain was recently shown to express two splice variants of NKCC1 (a and b) and the NKCC1 probe used in this study and all previous studies referenced here can only detect the NKCC1a isoform because the targeted epitope site of this probe overlaps with exon 21 that is spliced in the dominant isoform NKCC1b. A reliable pan-NKCC1 probe is not currently available.

A smaller sample of naïve age-matched controls (n=8, 4 each at P8 and P11, equal sexes) was run with the 24 h WB data (brains harvested at P8 and P11, i.e.; 24 h after P7 and P10 ligations). KCC2 and NKCC1 expression in the contralateral uninjured hemispheres from the ligate control pups (n=8, 4 each at P8 and P11, equal sexes) was not significantly different from their age-matched naïve controls ($p=0.49$ and $p=0.23$; KCC2 and NKCC1 respectively). This pilot established that contralateral hemispheres were ideal controls for normalization of KCC2 and NKCC1 expression in ipsilateral injured hemispheres for this study similar to previously reported conclusions in another ischemia model.

Statistics. Group means of total seizure burden, number of ictal events, and ictal duration within each treatment group were compared using repeated measures ANOVA with Bonferroni's post-hoc correlations. Differences with $p<0.05$ were considered statistically significant (repeated measures ANOVA; *=p<0.05 =p<0.01; *=p<0.001). The assumption of sphericity for data was confirmed by Mauchly's test, similar to Example 2 (Kang et al., 2015). Pairwise t-tests for group means were also reported. Independent sample t-tests were used to make comparisons between groups: i.e.; seizure burdens for P7 vs. P10. Western blot quantifications were compared among treatment groups using One-way ANOVAs. Correlation analyses were performed using non-parametric comparisons (Spearman's test, two-tail). Error bars depicted in figures represent mean±SEM.

TABLE 1

Sample sizes of ligated pups in each treatment- and age-group for EEG and WB experiments.

| EEG | | | | |
|---|---|---|---|---|
| P7 | Vehicle | ANA12 alone | ANA12 + PB + BTN | PB alone |
| Male | 4 | 4 | 11 | 4 |
| Female | 3 | 5 | 10 | 4 |
| Total | 7 | 9 | 21 | 8 |
| P10 | Vehicle | ANA12 alone | ANA12 + PB + BTN | PB alone |
| Male | 4 | 5 | 9 | 7 |
| Female | 4 | 6 | 12 | 5 |
| Total | 8 | 11 | 21 | 12 |

| Western Blot | | | |
|---|---|---|---|
| P7 | Vehicle | ANA12 alone | ANA12 + PB + BTN |
| Male | 3 | 4 | 7 |
| Female | 2 | 4 | 9 |
| Total | 5 | 8 | 16 |
| P10 | Vehicle | ANA12 alone | ANA12 + PB + BTN |
| Male | 4 | 3 | 7 |
| Female | 4 | 6 | 7 |
| Total | 8 | 9 | 14 |

Results

Figure 2:
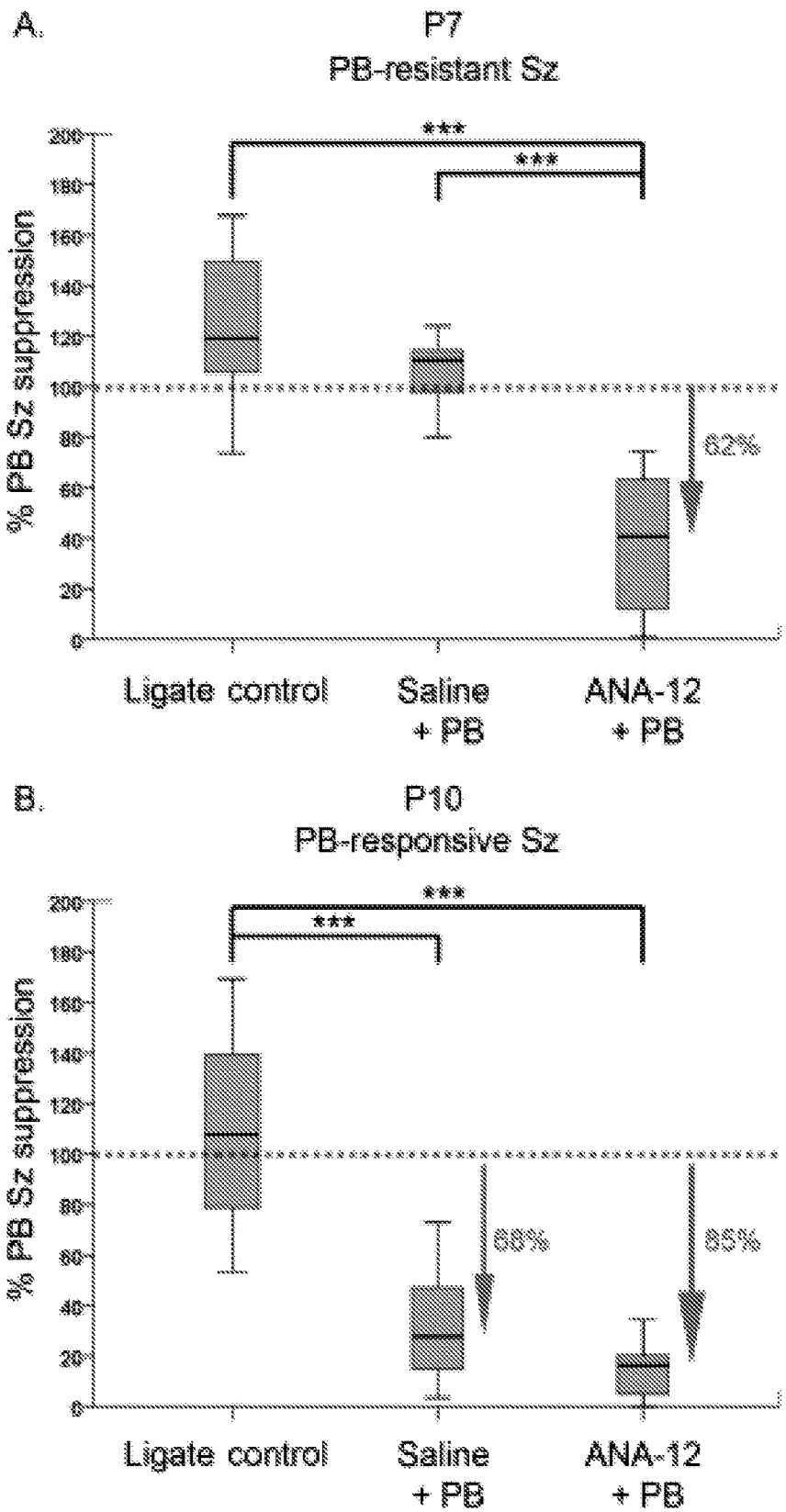
FIG. 2A-2B. ANA12 rescued PB-resistance at P7 and improved PB-efficacy at P10. The effect of ANA12 on PB-efficacy was evaluated as percent PB seizure suppression over baseline: % PB seizure suppression=100*[Post-PB seizure burden/baseline seizure burden]. A. PB by itself failed to subdue ischemic seizures at P7. ANA12+PB significantly subdued ischemic seizures by 62% (One-way ANOVA; ***=p<0.001). B. PB alone subdued seizures by 68% at P10. ANA12+PB improved this efficacy to 85%. This improved PB-efficacy however was not statistically significant when compared to the efficacy of PB alone. The sample size for saline+PB group was n=13 and n=1 for P7 and P10 respectively; n for ligate control and treated group was same as listed in FIG. 1 (see Table 2). Sz: Seizure.
Figure 8:
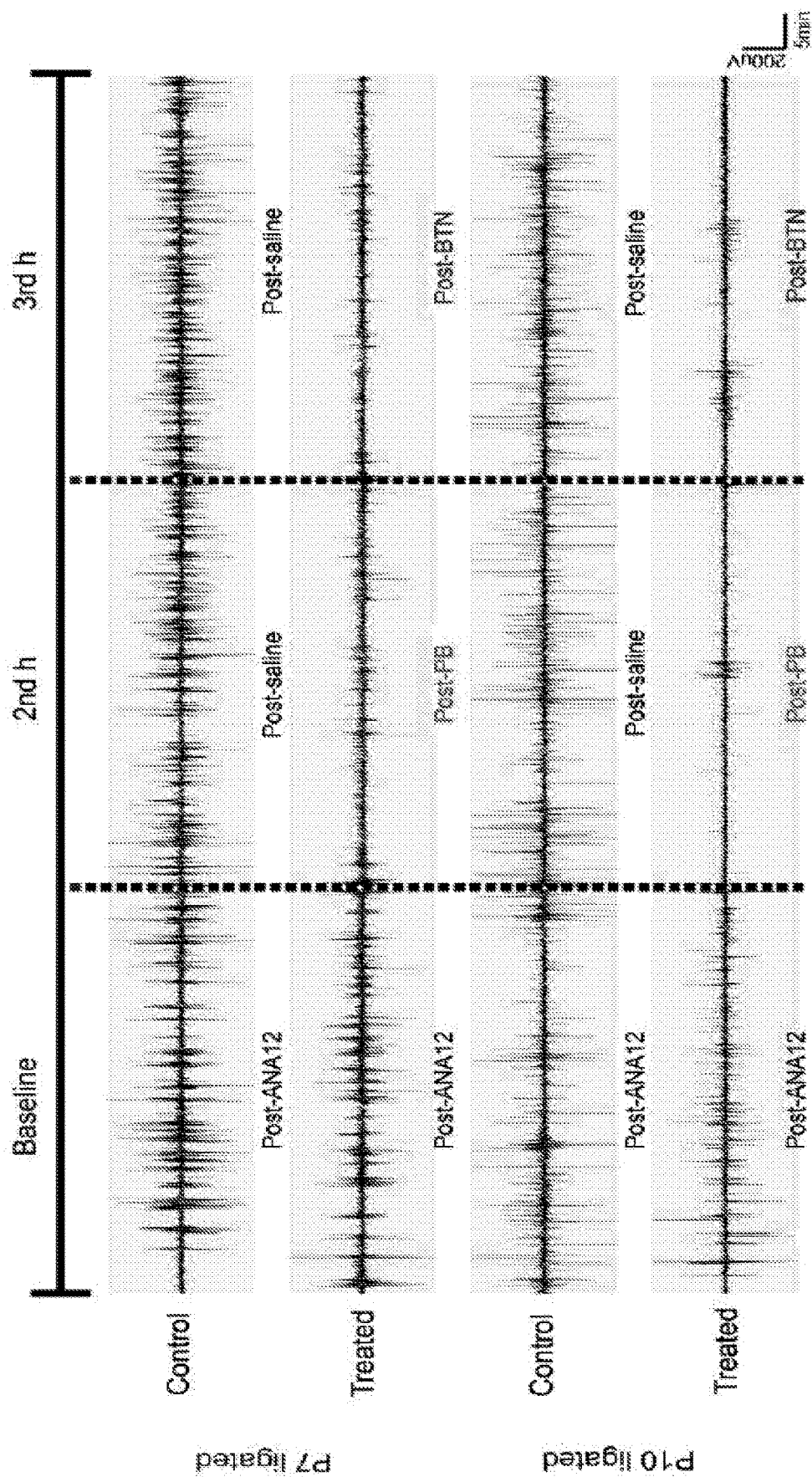
FIG. 8. Representative time-compressed plot (60×3=180 min) of continuous EEG traces recorded from P7 and P10 pups by ligate control vs. treated group. Timeline of 3 h EEG recording (top) and the representative compressed raw EEG traces for same duration are depicted for ligate control vs. treated group at each age. The timepoints of drug administrations (IP) are represented below each 1 h time-slot. All traces were selected from female pups that represented the mean total seizure burdens for each treatment group. ANA12+PB administration significantly suppressed seizures at P7 and P10, and BTN aggravated the PB-subdued seizures at P7 in females.
Figures 9A, 9B, 9C, 9D:
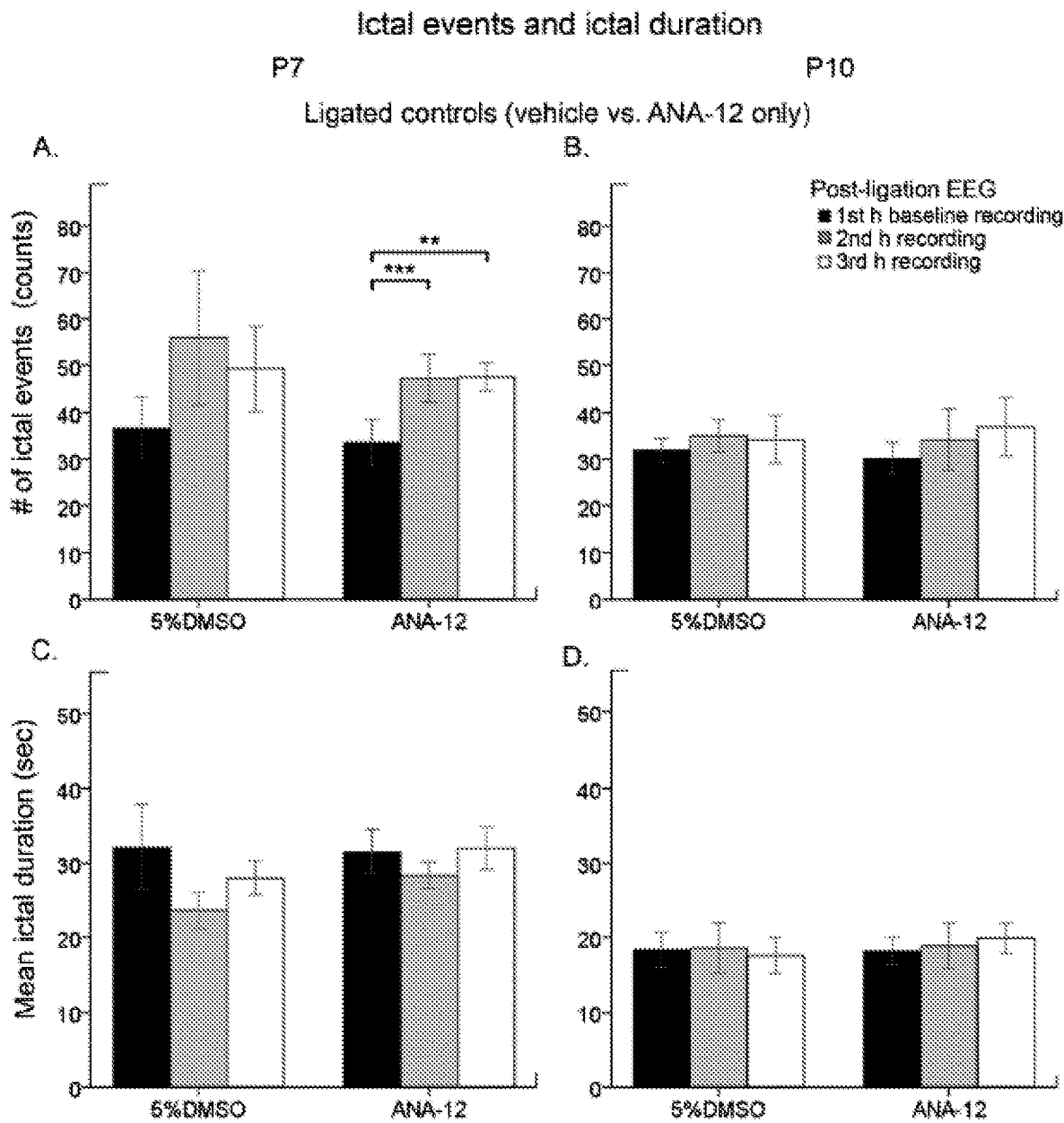
FIG. 9A-9H. Ictal events and ictal duration of electrographic seizures quantitated for different treatment groups. The number of ictal events and mean ictal durations were quantitated. A-B. ANA12-alone group showed a significant temporal increase in the number of ictal events at P7. However, pair-wise comparisons for the ictal events and duration of vehicle vs. ANA-alone group for each hour did not detect a statistical significance. C-D. Ictal durations were not significantly different between vehicle and ANA-alone treated groups. E-F. Ligate control group at P7 showed a significant temporal increase in the number of ictal events. The number of ictal events in treated group significantly dropped post-PB at both ages of P7 and P10. However, BTN administration significantly increased the number of ictal events at P10. G-H. Ictal durations for ligate control and the treated group were not significantly different. (Repeated measures ANOVA; *=p<0.05 =p<0.01; *=p<0.001).
Figures 9E, 9F, 9G, 9H:
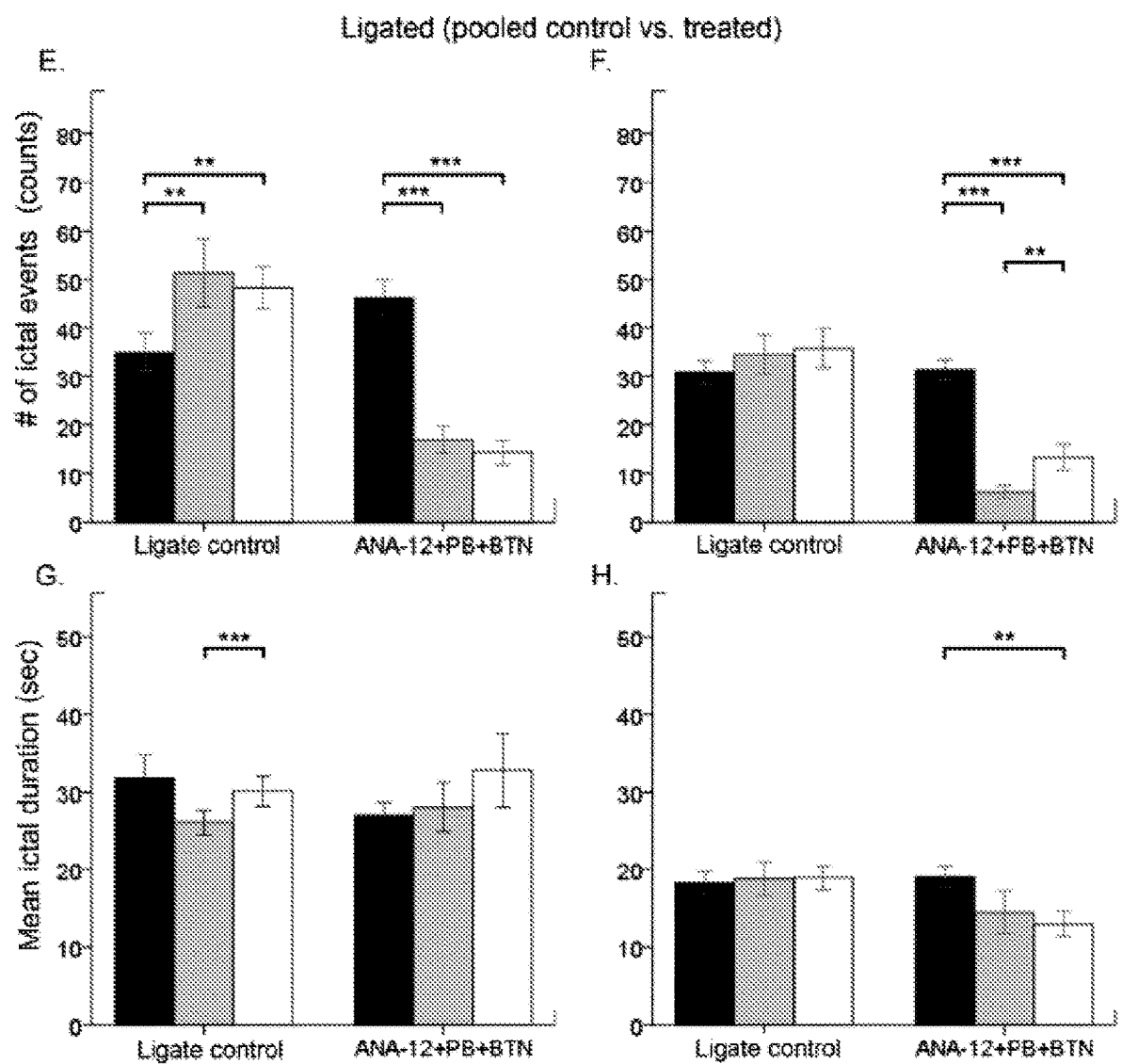

Small-molecule TrkB antagonist ANA12, rescued PB-resistance of seizures at P7 and improved PB-efficacy at P10. The effect of an acute single post-ischemic dose of ANA12 on PB-resistant seizures was evaluated at P7 and P10. PB administration at 1 h following ischemic insult in the ANA12 treated group significantly reduced the seizure burden at P7 and P10 (FIGS. 1B&D, FIG. 8: repeated measures ANOVA). ANA12+PB significantly suppressed seizures by 62% in P7 ischemic pups and by 85% in P10 ischemic pups (FIGS. 2A&B, FIG. 8: One-way ANOVA). In the absence of ANA12, PB failed to suppress seizures at P7, replicating the hallmark of the age-dependent PB-resistance in the ischemic model (Example 2, Kang et al., 2015). Similar to previous findings in the model, PB by itself suppressed seizures by 68% (FIG. 2B, p=0.001) in P10 pups. ANA12+PB improved PB-efficacy to from 68% to 85%, however this improvement was not significant (p=0.08). The seizure burdens quantitated here were additionally evaluated by the number of ictal events and the average ictal durations that constituted each seizure burden. The data showed that the anti-seizure efficacy of ANA12+PB at both ages was driven by a significant reduction in the number of ictal events (FIGS. 9E&F). The mean ictal durations did not change from baseline to the post-PB hour (FIGS. 9C-D and G-H). Therefore, acute TrkB inhibition significantly rescued PB-resistance at P7 and improved PB-efficacy at P10 by significantly reducing the number of ictal events post-treatment. Similar to Example 2 (Kang et al., 2015), PB-efficacy had no effect on ictal durations.

The between-group comparison of vehicle vs. ANA12-alone group did not differ significantly for any of the parameters of baseline seizure burden, the number of ictal events, and mean ictal duration at either P7 or P10 (FIGS. 1A&C). Additionally, Fisher's exact test comparing post-treatment mortality rate did not show a statistical significance (p=0.58 for P7, 1.00 for P10). Based on these observations, the data for vehicle and ANA12-alone group were pooled to form the "ligate control" group (n=15 and 19 for P7 and P10 respectively).

The efficacy of ANA12-alone as an anti-seizure agent was evaluated. As expected, ANA12-alone without PB administration did not have any anti-seizure effect at either P7 or P10. The baseline seizure burdens of ANA12-alone group did not differ significantly from that of vehicle group at either age (i.e., P7 p=1.00 and P10 p=0.63; One-way ANOVA). Additionally, ANA12 did not suppress the baseline seizure burden prior to PB administration in the treated groups at either age (FIGS. 1B&D). Therefore, an acute single dose of ANA12, in the absence of subsequent PB administration, failed to suppress ischemic seizures.

To evaluate whether vehicle or ANA12-alone had any effect on seizure susceptibility, the latency to onset of ischemic seizures following unilateral carotid ligation was evaluated in each pup. Neither vehicle nor ANA12-alone significantly altered the seizure onset latency. The effect of post-ligation drugs (saline, vehicle, and ANA12) on the latency to the 1 st-detected seizure were not statistically different at either age tested: P7; saline (321.7±58.8 sec), vehicle (321.7±171.3 sec), ANA12 (202.3±38.8 sec), P10; saline (150.73±40.4 sec), vehicle (164.4±44.4 sec), ANA12 (245.8±39.8 sec; One-way ANOVA: P7, p=0.28; P10, p=0.30 respectively). The latency to seizures in each treatment group did not significantly differ by age either. In summary, vehicle and ANA12 did not have any significant effects on age-dependent seizure susceptibility when evaluated by seizure onset latency in the model.

The effect of adding an adjunct NKCC1 antagonist, BTN, was also evaluated at the 3rd h of post-ischemia recording. BTN, delivered 1 h after PB, failed to act as an efficacious anti-seizure adjunct at either P7 or P10, similar to Example 2 (Kang et al., 2015). BTN did not reduce either the total seizure burden or the number of ictal events (FIGS. 1B&D, white bars; FIG. 8) at P7. BTN administration significantly blunted PB-efficacy by increasing the seizure burden in P10 pups (FIG. 1D; white bar p=0.01, FIG. 8). This aggravation occurred due to an increase in the number of ictal events following BTN administration (FIG. 9F; white bar p=0.02). Therefore, the blockage of NKCC1 after the successful rescue of PB-resistance did not help enhance PB-efficacy; instead, it resulted in an age- and sex-dependent aggravation of PB-subdued seizures, replicating previous observations in the model (Example 2, Kang et al., 2015).

Figures 10A, 10B, 10C, 10D:
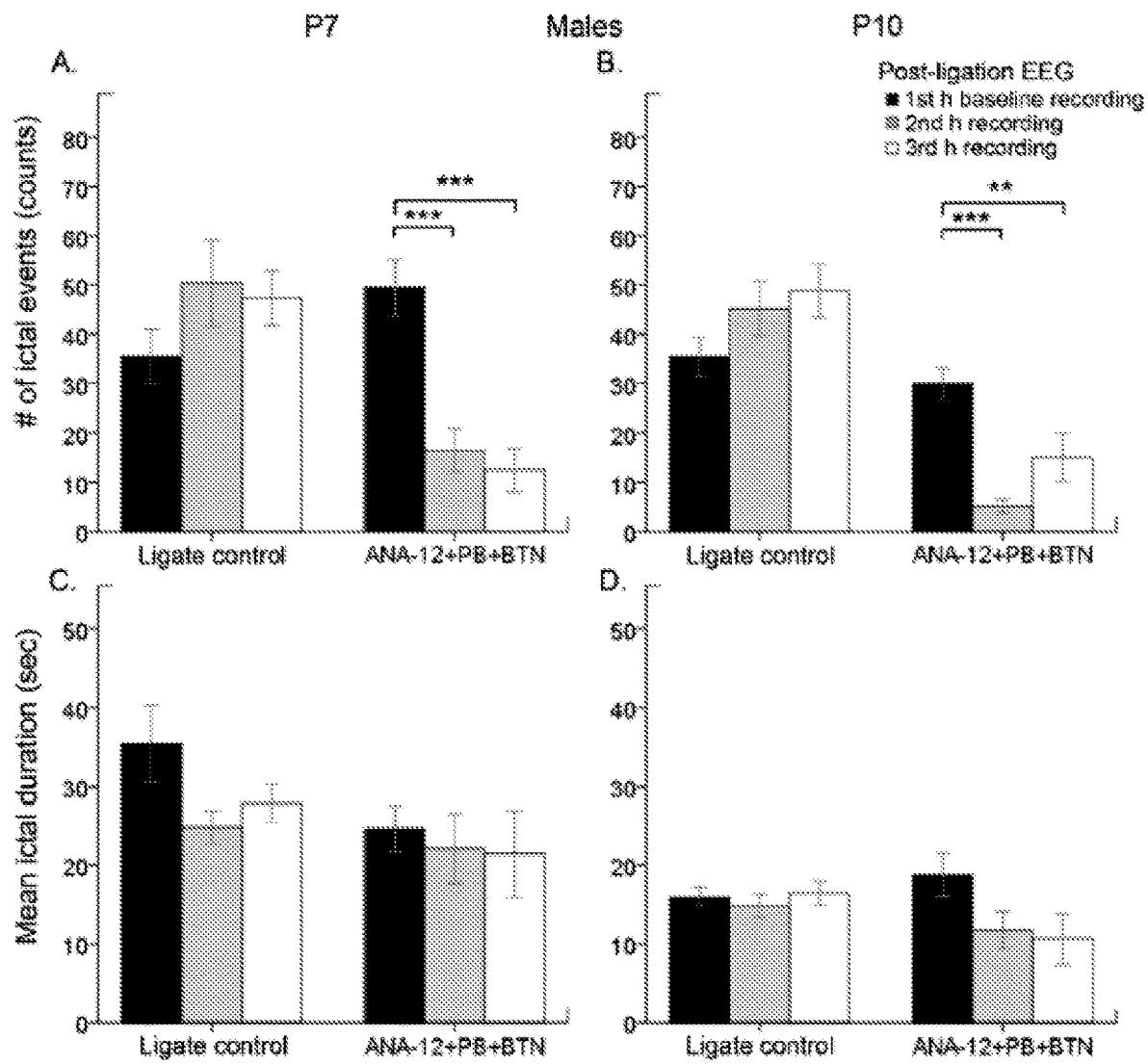
FIG. 10A-10H. Ictal events and ictal duration of EEG seizures quantitated for treatment groups by sex. The quantitation of ictal events and ictal durations for treated group was further separated by sex. A-B. ANA12+PB significantly suppressed the number of ictal events in males at both P7 and P10 compared to ligate controls. C-D. Ictal durations for ligate control and the treated group were not significantly different in males. E-F. ANA12+PB significantly suppressed the number of ictal events in females at both P7 and P10 compared to ligate controls. G-H. Ictal durations were not different by age or treatment in females. Overall, the ictal events and durations were not significantly different between male and female pups at either age tested. (Repeated measures ANOVA; *=p<0.05 =p<0.01; *=p<0.001).
Figures 10E, 10F, 10G, 10H:
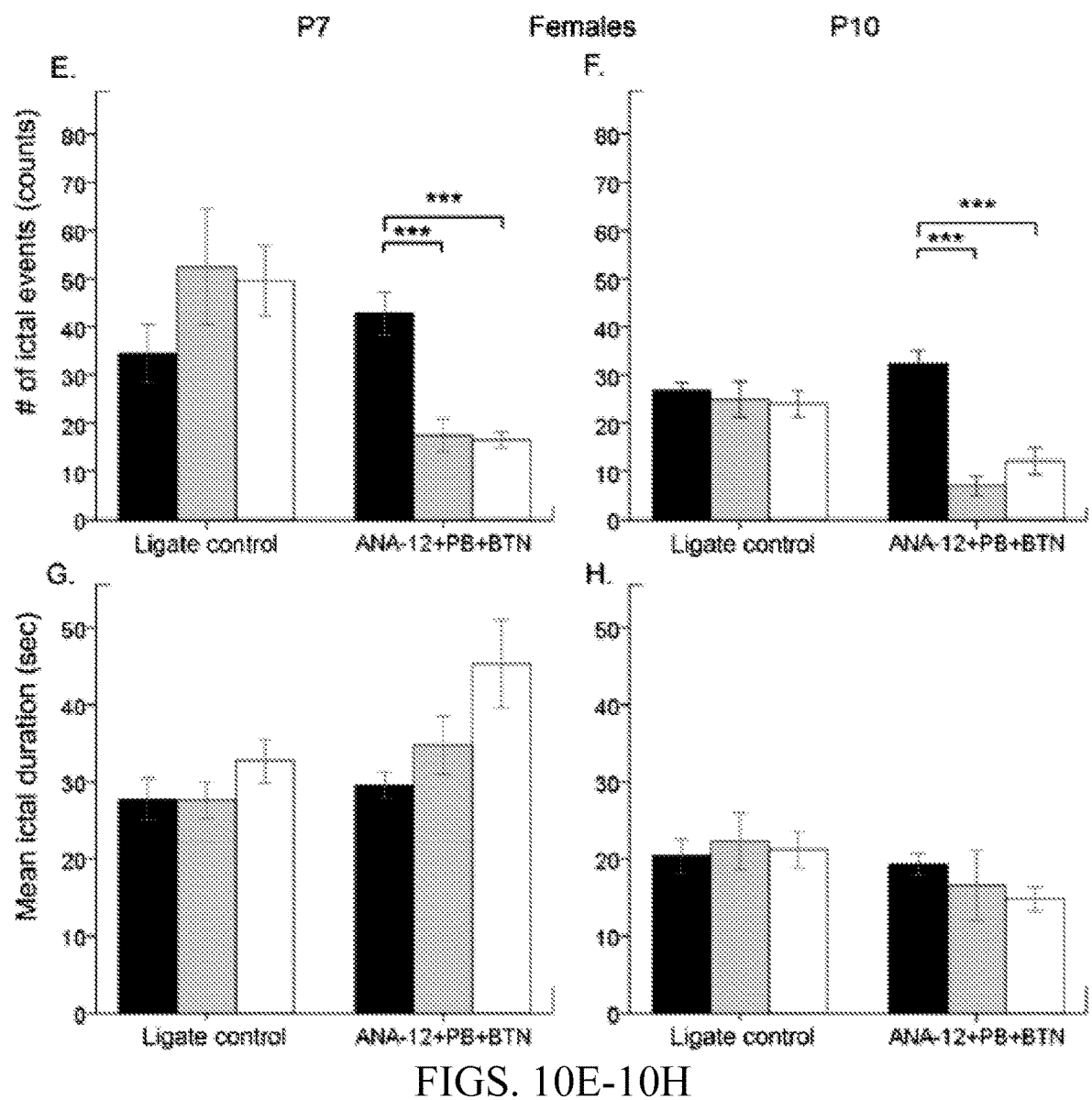

ANA12 significantly reversed PB-resistance at P7 and improved PB-efficacy at P10 in both sexes. The developmental expression profile of chloride co-transporters has been reported to be sexually dimorphic. To evaluate the role of biological sex in the efficacy of ANA12, the data presented in FIGS. 1B and D were evaluated by sex. PB-efficacy was significant for both sexes at P7 and P10 (FIG. 3A-D, FIGS. 10A-B and E-F; p<0.001 for all). In P7 pups, BTN significantly blunted ANA12+PB efficacy only in females (FIG. 3B). At P10, BTN blunted ANA12+PB anti-seizure efficacy in males but not in females (FIG. 10B; white bars). In summary, PB-efficacy was not different by sex and age. However, the BTN-associated aggravation of ischemic seizures was sex-dependent.

Age- and sex-dependent seizure susceptibility to ischemic seizures was unaltered by TrkB antagonist. The developmental regulation of chloride gradients is one of the known mechanisms that makes immature neurons hyper-excitable and more susceptible to ischemic seizures compared to mature neurons. The ligate control group displayed graded increase in the total seizure burden over the 3 h window of EEG recording (FIG. 1B), which was statistically significant at P7 but not at P10. Temporal increase of seizure burden during acute post-ischemic window is one of the characteristic features of the model (Kang et al., 2015). ANA12, administered after the onset of ischemia did not alter the significant age-dependent seizure susceptibility previously documented in this model (Example 2, Kang et al., 2015). Total seizure burden for ligate control group (i.e., over 3 h duration post-ischemia) was significantly higher in P7 (213%) pups compared to P10 pups (p=0.01), thus replicating the characteristic feature of the model (FIGS. 1A&C).

Figure 4:
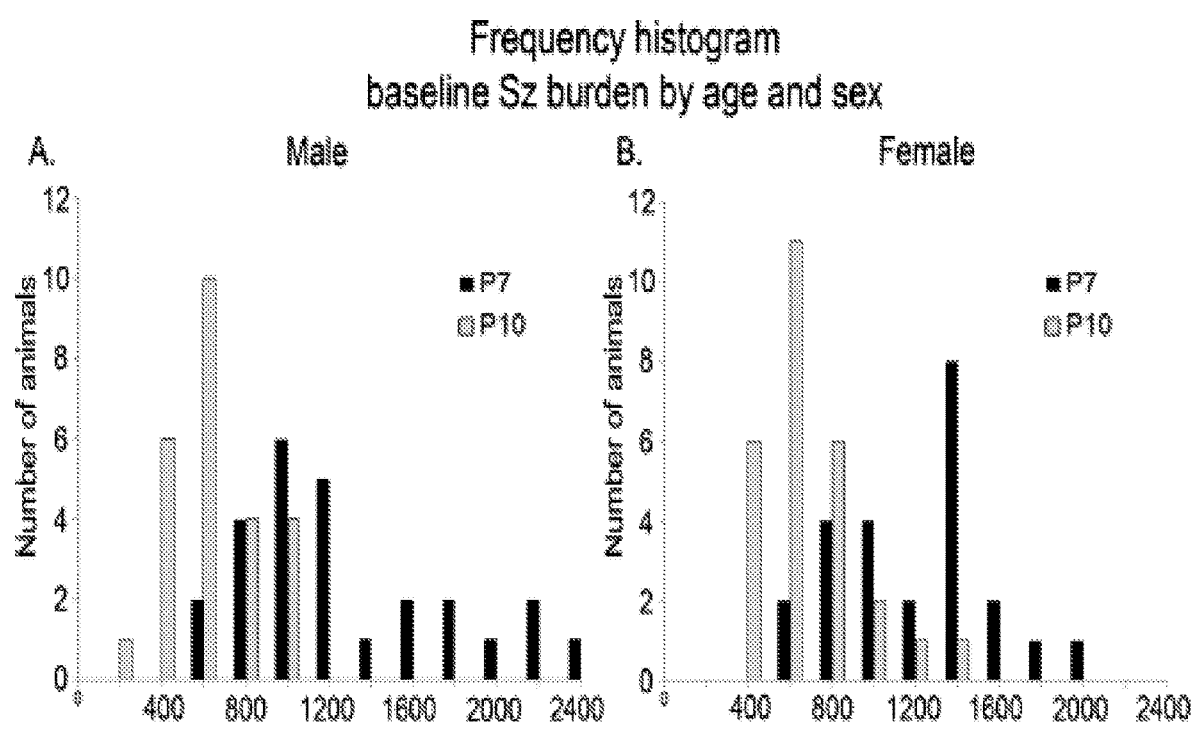
FIG. 4A-4B. Frequency distribution of baseline seizure burdens shows age-dependent susceptibility. A&B. Frequency histogram of baseline seizure burdens was plotted, separated by age and sex. Both sexes displayed higher seizure susceptibility at P7 compared to P10: sample size P7 (n=50) and P10 (n=39). The between-group comparison of baseline seizure burdens by sex was not statistically different at either P7 or P10.

The ligate control and treated groups did not differ in their baseline seizure burdens (i.e.; black bars FIGS. 1B&D) at P7 or P10. Additionally, similar to the characteristics previously noted for the model, a significantly higher seizure susceptibility was observed in P7 male pups compared to P10 male pups (p=0.001). This age-dependent susceptibility was not significant (p=0.76) between P7 and P10 females (FIGS. 4A&B). Therefore, the age- and sex-dependent seizure susceptibility to ischemic seizures established in the model was not altered by ANA12.

Figure 5:
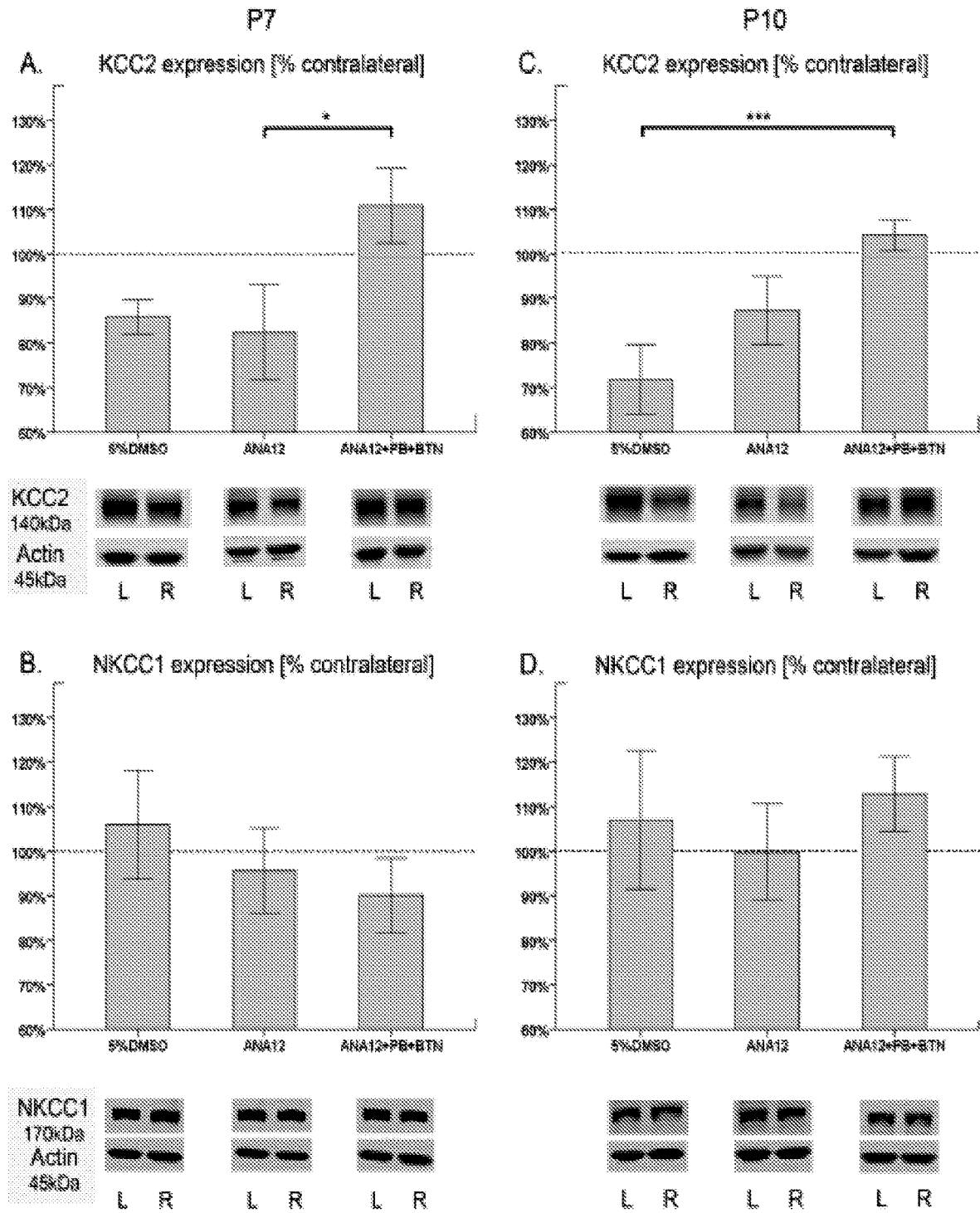
FIG. 5A-5D. ANA12+PB rescued KCC2 expression but had no effect on NKCC1 expression at 24 h. A-D. Bar graphs represent mean expression of KCC2 and NKCC1 in ipsilateral hemisphere normalized to the contralateral at 24 h after ischemia. β-actin was used as an internal control. The protein bands for both co-transporters were: 1) normalized to the level of actin for the same sample, 2) followed by normalization of ipsilateral co-transporter expression levels to contralateral hemisphere of the same pup A&C. The post-ischemic degradation of KCC2 expression (~20%) was prevented in the ANA12+PB+BTN treated group at P7 and P10. B&D. Post-ischemic expression levels of NKCC1 in the treated group were not significantly different from ligate controls (One-way ANOVA; *=p<0.05; ***=p<0.001).

ANA12 followed by PB rescues the ischemic downregulation of KCC2 expression at both P7 and P10. Approximately ~20% downregulation of KCC2 expression in the ipsilateral ischemic hemisphere compared to the contralateral hemisphere was previously documented in the model when evaluated at 24 h post-ischemia (Example 2, Kang et al., 2015). The effect of TrkB inhibition on post-ischemic KCC2 degradation was evaluated. Quantification of KCC2 expression at 24 h after an ischemic insult indicated that the post-ischemic degradation of KCC2 expression was significantly prevented in the treated group at both P7 and P10 (FIGS. 5A&C). At P7, both vehicle and ANA12-alone group exhibited KCC2 degradation that was approximately 15-18% lower compared to the contralateral hemisphere; which was statistically significant between ANA12-alone and the treated group (FIG. 5A; p<0.05). The expression levels of KCC2 in the PB-resistance rescued group was ~110%, and therefore similar to the contralateral hemisphere. At P10, both vehicle and ANA12-alone group displayed KCC2 degradation, while the treated group showed significant rescue. However, the vehicle group showed ~30% KCC2 degradation whereas ANA12-alone group showed ~12% KCC2 degradation, compared to the contralateral hemisphere. The KCC2 downregulation was only significant between the vehicle group and the treated group (FIG. 5C). The ligate control group representing the vehicle and ANA12-alone data pooled together similar to the seizure burden data in FIGS. 1B&D, showed significant post-ischemic degradation of KCC2 expression (16.2% and 20.0% for P7 and P10 respectively) when compared to the ANA12+PB treated group (p=0.04 and 0.002; P7 and P10 respectively). NKCC1 expression was also quantitated in the same manner as it was done for KCC2, and no statistically significant differences were detected amongst treatment groups (FIGS. 5B&D). Additionally, the overall percent NKCC1 change in the treated group was also not significantly different by age (P7 vs. P10; One-way ANOVA p=0.28). In summary, a single acute dose of ANA12, in the presence of follow-on PB, significantly prevented the post-ischemic degradation of KCC2 expression even at 24 h post-ischemia, and did not significantly alter NKCC1 expression.

Figures 11A, 11B, 11C, 11D:
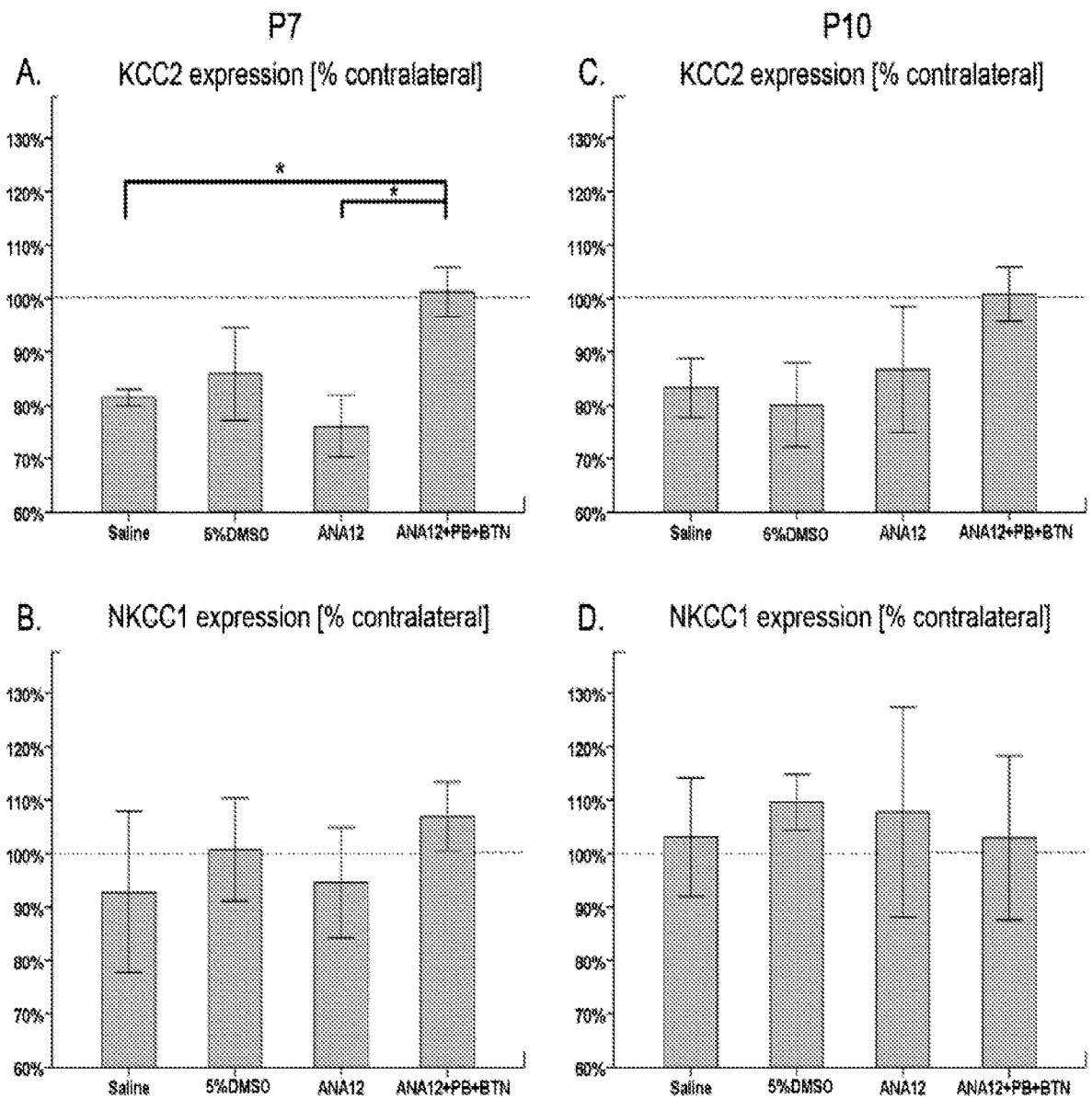
FIG. 11A-11D. ANA12+PB rescued KCC2 expression but had no effect on NKCC1 expression at 3 h. Brains harvested at 3 h post-ischemia underwent WB analyses to quantitate expression levels of KCC2 and NKCC1, similar to 24 h WB analyses (FIG. 5). An additional group of saline-only treatment group was included. A&C. ANA12+PB+BTN treated group showed that the post-ischemic degradation of KCC2 expression was rescued at both ages of P7 and P10. The statistical significance for the rescue in KCC2 expression was only present at P7 at the 3 h time-point (One-way ANOVA; *=p<0.05; ***=p<0.001). B&D. NKCC1a expression remained similar to saline controls regardless of the treatment paradigm, replicating the 24 h WB data.

KCC2 expression levels were also evaluated acutely at 3 h post-ischemia. An additional group of saline treatment was included in this experiment, to establish the KCC2 expression in untreated ischemic pups. The results were similar to the findings for the 24 h data. At P7, all groups except the ANA12+PB treated group underwent approximately 15-20% downregulation of KCC2 expression (FIG. 11A). A similar 20% loss of KCC2 surface expression has been shown to decrease KCC2 function by 50%. The KCC2 expression levels for saline group and ANA12-alone group significantly differed from the treated group, but the vehicle group did not (One-way ANOVA; p<0.05). At P10, the vehicle and ANA12-alone groups also underwent degradation of KCC2, however no statistical significance was detected when compared to the ANA12+PB treated group (FIG. 11C). Similar to the 24 h results, NKCC1 expression among groups was not statistically different (FIGS. 11B&D).

Since severe seizures can independently degrade KCC2 in a non-TrkB dependent pathway, a pilot experiment to evaluate the efficacy of ANA12 to rescue PB-resistance after the occurrence of status-like seizures was additionally conducted. In contrast to experimental paradigm described in FIG. 1, ANA12 was administered 1 h after PB in P7 seizing pups (i.e.; 2 h after repetitive ischemic seizures, PB+ANA12). The post-PB administration of ANA12 protocol, failed to subdue the PB-resistant seizures at P7 (p=1.00; n=3). Additionally, this treatment protocol also failed to rescue post-ischemic KCC2 degradation when evaluated at 24 h (p=1.00; n=5) similar to the vehicle-treated pups. These data indicate that the TrkB-pathway-mediated KCC2 degradation (~20%) starts early after ischemia and is irreversible by administration of ANA-12 after emergence of PB-resistance.

Figure 6:
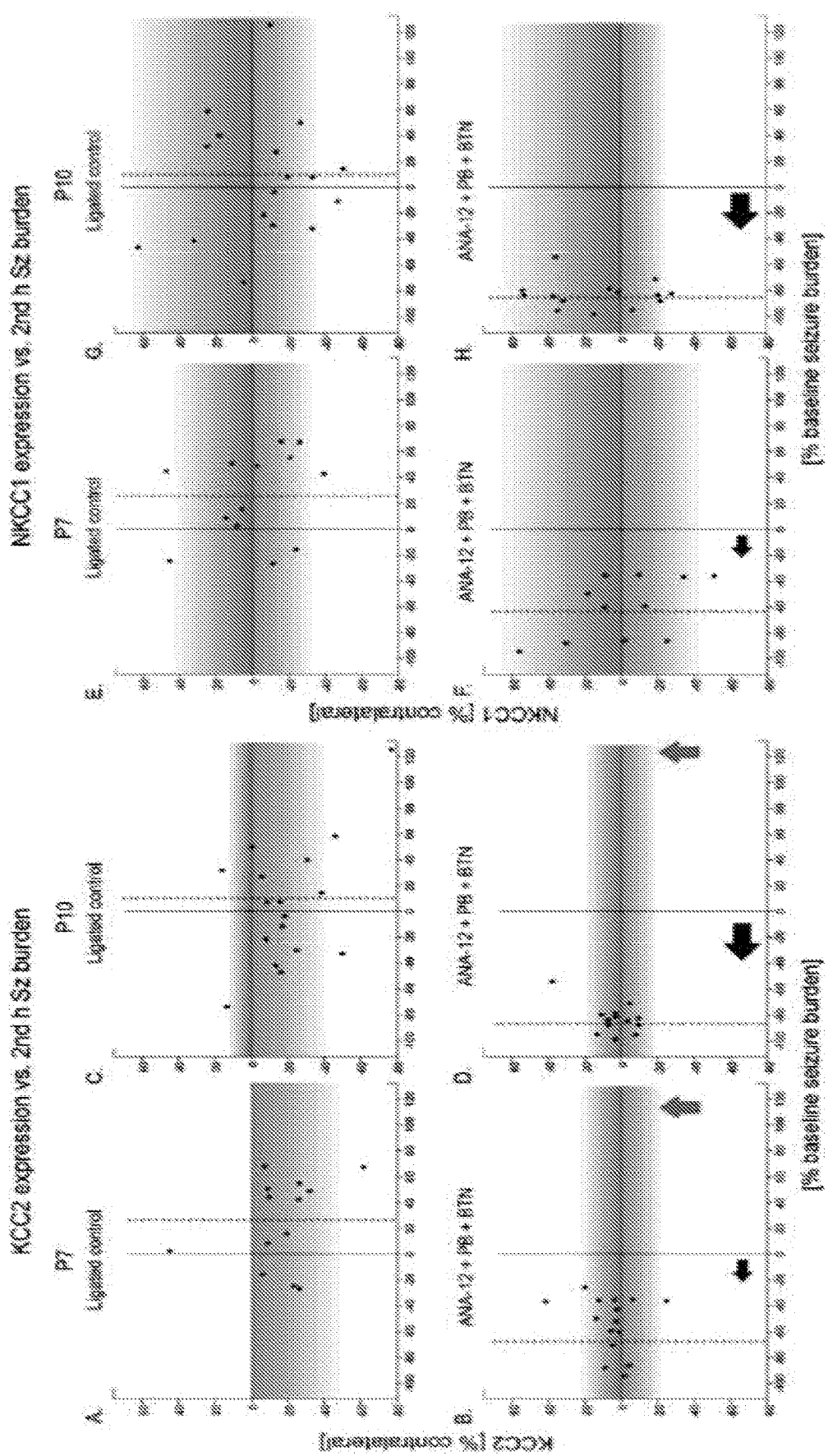
FIG. 6A-6H. Significant correlation between rescue of KCC2 degradation at 24 h and seizure suppression was detected. The percent change of KCC2 (or NKCC1) expression of an ipsilateral hemisphere [% change=100*(ipsi−contra/contra KCC2 expression)] was correlated to the percent seizure suppression [% baseline seizure burden=100*(baseline seizure burden−post-PB seizure burden)/baseline seizure burden)]. The color gradient (blue or red) applied to the background represents the data distribution in the positive (blue) or negative (red) direction of KCC2 expression after ligation/treatment. The dotted gray lines within each scatter plot represent the mean values for percent seizure suppression in each group (x axis). A&C. The ligated control group at both ages of P7 and P10 showed the post-ischemic degradation of KCC2 expression evident by predominant distribution of dots on the red gradient. B&D. The post-ischemic KCC2 expression of the treated group was rescued at both ages of P7 and P10, as seen in the positive-shift of the dots towards the blue gradient (red arrows). The correlation between the percent KCC2 expression and percent seizure suppression (black arrows) was significant at P10 (Spearman's test; p=0.04) but not at P7. When P7 data were binned by baseline seizure burden (<1200 sec vs.≥1200 sec), the correlation became significant for the pups that seized <1200 sec (p=0.02; data not shown). E&G. The ligated control group at both ages of P7 and P10 showed inconsistent and non-significant changes in the post-ischemic NKCC1a expression. F&H. NKCC1 expression levels of post ANA12+PB+BTN treatment did not show any significant correlations with efficacious PB seizure suppression.
Figure 7:
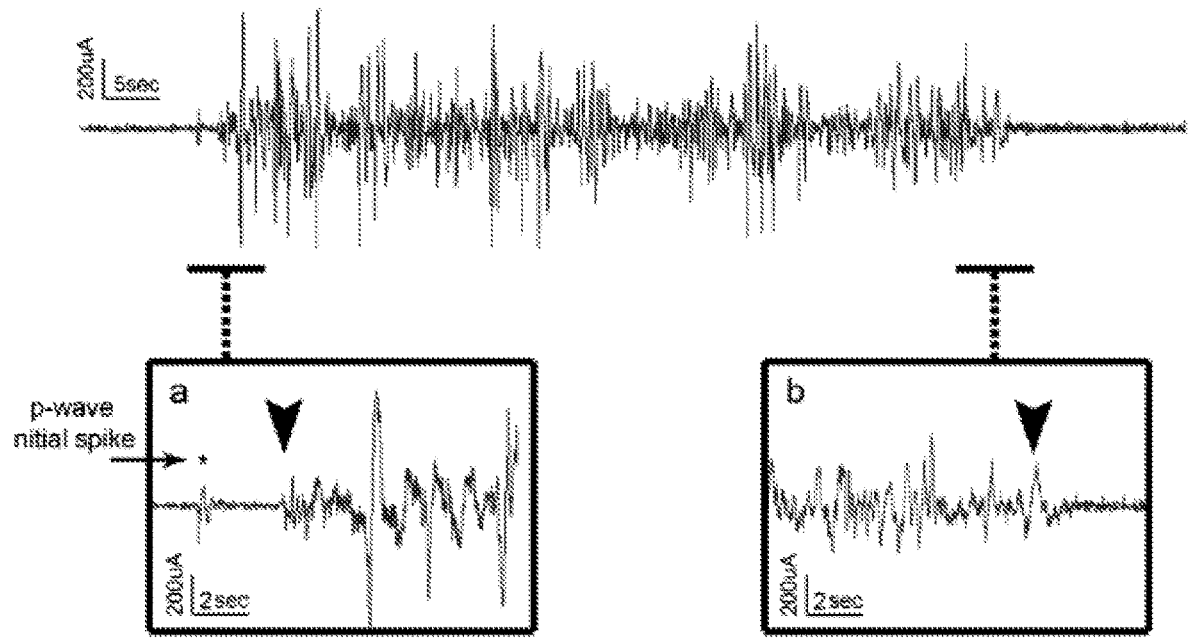
FIG. 7A. Representative electrographic seizure. Representative trace of a raw EEG recording of an ictal event associated with tonic-clonic convulsive behavior on video lasting 90 seconds.
Figure 7:
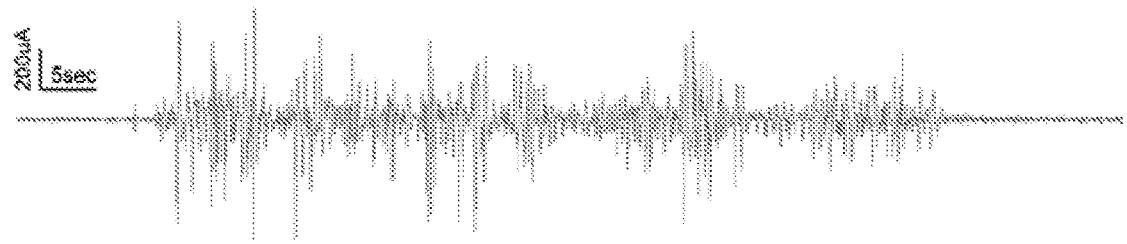
Figure 7:
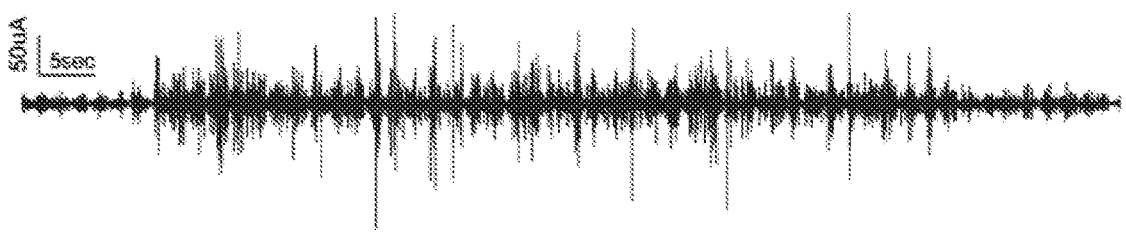

Correlation of PB-efficacy and KCC2 expression. Correlations between seizure suppression and KCC2 degradation were evaluated to determine whether the PB-efficacy was driven by the prevention of KCC2 degradation. P10 pups showed a significant correlation between efficacious seizure suppression and rescue of KCC2 expression at P10 (FIG. 6D; p=0.04, r=0.6). This correlation was not significant at P7 (FIG. 6A-D; p=0.35, r=0.2). This differential correlation may be in part due to age-dependent upregulation of KCC2 in naïve brains during this developmental window (Example 2, Kang et al., 2015). Naïve P10 pups have been reported to have a higher age-dependent expression of KCC2 compared to P7 (Example 2, Kang et al., 2015). However, the percentage of KCC2 degradation following ischemia at both P7 and P10 were similar (i.e.; ~20%) and not significantly different (One-way ANOVA; p=0.84). No significant correlations between seizure suppression and NKCC1 expression were detected at P7 or P10 (FIG. 6E-H), which was expected from the inconsistent (FIGS. 6 E&G) post-ischemic expression levels of NKCC1 detected at both ages for all treatment groups (FIGS. 5B&D and FIGS. 11B&D).

The efficacy of PB seizure suppression was significantly dependent on the baseline seizure burden at P7 but not at P10 (Spearman's test: i.e.; P7; p=0.001, P10; p=0.30). P7 pups with severe baseline seizure burden (i.e.; >1200/3600 sec) were less responsive to ANA12+PB with a 54.9±6.6% seizure suppression (n=10, p<0.001) in contrast to their age-matched ligated-pups with lower baseline seizure burden (<1200/3600 sec) that responded with a 68.5±8.3% seizure suppression to ANA12+PB (n=11, p<0.001). Using this binning for moderate and severe baseline seizure severity at P7 (i.e.; seizing for < or >⅓ of the total baseline hour), correlations between seizure suppression and rescue of KCC2 degradation became evident. Ligated pups at P7 that seized for less than ⅓rd of the hour before PB administration, showed a significant positive correlation with rescue of KCC2 degradation (p=0.02, r=0.8) similar to that detected in P10 rescued pups. In contrast, in pups which seized for >⅓rd of the hour, this correlation was not only lost significance but became negative (p=0.31, r=−0.4). In summary, if the baseline seizure burden was status-like at P7 (i.e.; >1200/3600 sec), the ANA12+PB anti-seizure efficacy did not correlate significantly with percent KCC2 expression (FIG. 6B). In contrast, the percent change in the expression levels of NKCC1 did not correlate significantly with the percent post-PB seizure suppression (FIGS. 6F&H), and further binning by baseline seizure severity did not reveal any significant correlations either. Ligated pups at P10 responded significantly to PB regardless of the severity of their baseline seizures burden. The age-dependent seizure susceptibility and PB-resistance has been previously reported and this study replicated that hallmark characteristic for the model (Example 2, Kang et al., 2015).

Discussion

Using a small-molecule TrkB antagonist and a single systemic (IP) dosing protocol, this study reports for the first time, the proof-of-concept results for the pharmaco-modulation of KCC2 expression as a novel strategy for preventing the emergence of PB-resistant seizures in neonatal ischemia. The salient findings are: 1) a single post-insult dose of TrkB antagonist, ANA12, significantly rescued the PB-resistance of ischemic seizures at P7; 2) the combination of a single dose ANA12+PB at 1 h, not only prevented the acute post-ischemic degradation of KCC2 expression at 3 h but also maintained age-dependent KCC2 expression 24 h later; 3) the TrkB antagonist by itself could neither prevent the occurrence of ischemic seizures nor rescue post-ischemic KCC2 degradation, suggesting that PB-resistant seizures can independently degrade KCC2 by non-TrkB dependent pathways; 4) At P10, ANA12 helped improve PB-efficacy; and 5) NKCC1 antagonist BTN failed to further improve PB-efficacy as an adjunct therapy at both ages. These findings highlight the pivotal role of KCC2 in seizure susceptibility and the emergence of PB-resistant seizures in neonatal ischemia. Therefore, transient pharmaco-modulation of KCC2 with the goal to restore the developmental profile of KCC2 upregulation may be a promising strategy for preventing the emergence of PB-resistant seizures in HIE.

A single dose of ANA12 reversed PB-resistance at P7. Age-dependent PB-resistance of ischemic seizures was the hallmark of the neonatal ischemic seizure model used here (Example 2, Kang et al., 2015). ANA12 successfully reversed PB-resistance at P7 at a dose of 2.5 mg/kg. Therefore, the inability of old-generation TrkB antagonists crossing the blood brain barrier was successfully circumvented by the small molecule TrkB antagonist, ANA12. The brain bioavailability of ANA12 after systemic injection, examined in adult mouse brains indicates that ANA12 administered IP at 0.5 mg/kg dose was active as early as 0.5 h [400 nM] up to 6 h [10 nM] (Cazorla et al., 121 J. CLIN. INVEST. 1846-57 (2011)). Additionally, a single dose of 0.5 mg/kg ANA12, in the same study, suppressed the ratio of phospho-/total TrkB activity in the whole brain by 8% at 2 h and 25% at 4 h. The post-insult transient opening of blood brain barrier in the immature brain has been shown to result in the increased bioavailability of small and large molecules, and may suggest a similar enhancement in the pharmacokinetics of the single dose ANA12 given acutely in this model of neonatal ischemia. In summary, acute TrkB inhibition by a single dose of ANA12, achieved significant rescue of PB-resistance even when PB was given 1 h after the occurrence of severe recurrent seizures.

ANA12 required 5% DMSO to stay in solution. DMSO can independently act as an anti-epileptic drug by modifying brain bioelectric activity, specifically at above 50% concentration but not at below 10%. To evaluate the anti-seizure effect of 5% DMSO used as vehicle for ANA12 in this study, a separate vehicle-treatment group of 5% DMSO was investigated. 5% DMSO administered following ischemia did not have any anti-seizure effect in this study, and the baseline seizure burdens remained unaltered and similar to Example 2 (Kang et al., 2015).

A single dose of ANA12 with PB prevented both early and late downregulation of KCC2 expression after ischemia. The BDNF-TrkB pathway has been shown to be responsible for excitoxicity related degradation of KCC2 in in vitro experiments. This degradation has been shown to occur within minutes of an ischemic insult in vitro. BDNF-TrkB pathway has also been implicated in epileptogenesis, neuropathic pain, and psychiatric disorders. Ischemic insults resulted in the downregulation of KCC2 expression levels in several studies. Our previous studies have shown that neonatal ischemia resulted in a transient downregulation of KCC2 expression that recovered over the period of a few days and caught up with the age-dependent KCC2 upregulation occurring during this developmental window (Example 2, Kang et al., 2015). Similar KCC2 degradation has also been reported to occur hours after the onset of status epilepticus. However, those studies used chemoconvulsants to induce seizures that also resulted in an early upregulation of KCC2 similar to a hypoxia-only model of neonatal seizures. The mechanism underlying this early upregulation of KCC2 was not explored by either group. However, recent research has reported that the kainate-dependent upregulation of KCC2 was a homeostatic response to increased neuronal firing during early seizures and occurs via the ERK1/2 signaling cascade that may help improve inhibition.

In contrast, when status epilepticus continued to occur over a period of >240 min in the Puskarjov et al. study (Puskarjov et al., 88 NEUROPHARMACOLOGY 103-09 (2015) (Epub 2014 Sep. 16., doi: 10.1016/j.neuropharm.2014.09.005), KCC2 degradation via the calpain-mediated pathway became evident. These findings indicate that early KCC2 homeostatic upregulation may fail in etiologies associated with energy deprivation like ischemia. Additionally, after severe and repeated seizures have occurred, seizures alone may degrade KCC2 function through non-TrkB mediated pathways. However, our results also indicate that if the PB-resistant seizures are subdued early by blocking TrkB, the late onset KCC2 degradation can also be prevented.

Repeated seizures can independently lead to KCC2 degradation. Prevention of KCC2 degradation only occurred in the presence of both TrkB inhibition and efficacious seizure suppression. In contrast, the vehicle and ANA12-alone groups both underwent significant KCC2 downregulation in the ipsilateral hemisphere (FIG. 5) similar to untreated pups (Example 2, Kang et al., 2015). ANA12-alone failed to prevent the post-ischemic KCC2 degradation in pups where ischemic seizures continued. This indicates that prolonged recurrent seizures are capable of degrading KCC2 expression likely through a non-TrkB mediated pathway. Calpain-dependent downregulation of KCC2 had been shown to occur following 3 h of status epilepticus induced seizures. Calpain is a calcium-sensitive protease which is activated in conditions associated with long duration status epilepticus. Similarly, the failure of ANA12 to improve PB-efficacy when given 1 h after PB showed that when many repeated ischemic seizures have already occurred (i.e.; 2 hours of repetitive post-ischemic seizures), ANA12 failed to reverse KCC2 downregulation even in the presence of PB, indicating that TrkB pathway related KCC2 degradation starts early after ischemia. Both of these observations support the previous conclusions that severe seizures are independently detrimental in ischemia and can lead to KCC2 downregulation initiated by both TrkB and non-TrkB dependent pathways. Since the calpain pathway has been shown to be triggered later during a severe status-like seizure cascade in a slice culture model and in acute slices derived from mice after kainate induced status, it may be temporally different from the BDNF/TrkB pathway in the sequence of initiation post-insult. Inability of calpain inhibitors to cross the BBB is currently prohibitive to test the hypothesis in an in vivo model.

At P10, with the age-dependent lower seizure burden as compared to P7, and developmentally higher expression profile of KCC2 in naïve brains, the ANA12-alone group showed a trend towards the recovery of KCC2 expression compared to the vehicle groups at both 3 h and 24 h, however it was not statistically significant. This indicates that TrkB inhibition, in the absence of PB, may be able to marginally rescue KCC2 degradation by itself at P10 but not at P7. This difference may be due to the age-dependent susceptibility to ischemic seizure burden and the developmental profile of KCC2 upregulation (i.e.; P10>P7).

Correlation between rescue of KCC2 downregulation and efficacious seizure suppression. The results of this study indicated that when seizures were efficaciously suppressed, there was an associated significant rescue of KCC2 degradation at both P7 and P10 (FIG. 6). This was not true for NKCC1, highlighting the critical role of Cl− extrusion played by KCC2 in determining the efficacy of GABAA agonists like PB. However, it is important to note that the currently available NKCC1 probes can only detect the non-dominant isoform NKCC1a. The dominant isoform NKCC1b expressed in the brain is a spice variant with missing exon 21 that remains undetected with currently available probes. Unlike NKCC1a, NKCC1b has been shown to have stable expression throughout development and adulthood in human brains. These findings from human brain research, indicate that the previous interpretations related to the developmental downregulation of the immature form Cl− transporter, NKCC1 with age, in animal research models may not be accurate. A reliable pan-NKCC1 probe is not currently available, but is an area of active research. Therefore, in the absence of a probe capable of detecting simultaneous NKCC1a and NKCC1b expression levels, interpretations related to the expression profile of NKCC1 and the BTN-inefficacy replicated in this study, remain elusive. In contrast, the KCC2 probe used in this study, detects both brain isoforms with rigorous specificity (Williams et al., 1999). In addition, KCC2 protein can stay internalized in cytosolic vesicles or remain inactive in the plasmalemma, therefore, additional strategies to increase the membrane insertion kinetics of KCC2 proteins may also be an appropriate alternative to test the proof-of-concept approach investigated here.

The significant positive correlation of seizure suppression to rescue of KCC2 degradation at P10 was absent at P7. However, when data were binned by baseline seizure severity (< or ≥1200 sec), there was a strong positive correlation of the rescue of KCC2 degradation to the severity of the baseline seizure burden before PB was administered at P7. This indicated that when a P7 ligated pup seized for >⅓rd of the first hour (i.e.; status-like severity) before PB administration, non-TrkB related pathways like calpain-mediated KCC2 degradation, may get initiated earlier, weakening the significant correlation detected in pups with relatively lower seizure burdens. This observation highlights the important role of seizure severity in the emergence of refractoriness. Severe repeated seizures can degrade KCC2 by multiple pathways. Therefore, both the etiology and severity of seizures dictate the pharmacological consequences in neonates.

Role of KCC2 in brain development and long-term sequelae of transient KCC2 down-regulation.

KCC2 is known to play a role in early development, spine formation, interneuron migration, and synaptogenesis, which may occur independently to KCC2's function as a Cl− extruder. KCC2 is robustly expressed in the dendritic spines of cortical neurons. KCC2 also plays a crucial role in development of interneurons and their response to injury. The stronger tolerance of CA1 interneurons to ischemic injury compared to pyramidal cells reported in the hippocampus, may suggest that the higher density of KCC2 in CA1 interneurons may drive the exceptional resistance of parvalbumin-positive interneurons to excitotoxic injury associated with ischemia. Ischemic insults can result in long-term damage to interneurons that become evident after months. The transient ischemia-related KCC2 degradation during early development detected in this model may have neurological consequences that are not evident in the acute stages but may manifest as late-onset co-morbidities.

A study conducted in human brains has reported that KCC2 expression was significantly lost in the brain samples of preterm infants with white matter damage. Therefore, KCC2 degradation may be a common pathology associated with perinatal brain insults that are excitotoxic. Pharmacomodulation of KCC2 with the goal of restoring normal expression levels seems to be a viable path forward not only for acutely preventing the emergence of PB-resistant seizures in neonates as shown in the results but also possibly preventing the long-term neurodevelopmental deficits. These hypotheses require follow-on long-term studies. The known action of ANA12 as an anti-depressant and anxiolytic in rodent studies supports the further evaluation of the long-term effects of ANA12 following neonatal use in this model. The prevention of KCC2 degradation documented in this study should be clearly differentiated from KCC2 overexpression, because upregulation of KCC2, above its normal developmental expression levels, that is not physiological, may lead to a precocious maturation of neuronal circuits in immature brains. Ischemic seizures are transient during the neonatal period, and therefore a single acute intervention to prevent KCC2 degradation similar to that reported here during the critical stage may be sufficient.

Blocking NKCC1 fails to improve PB-efficacy. The efficacy of BTN as an adjuvant anti-seizure agent has been controversial. The recent termination of NEMO clinical trial [NCT01434225] reported the inefficacy of BTN for HIE seizures. Our recent studies have also reported a similar BTN inefficacy for acute ischemic seizures and detected an age- and sex-specific aggravation of PB-subdued seizures in P10 CD1 pups (Example 2, Kang et al., 2015). These findings were replicated in the current study. In spite of the improved PB-efficacy elicited by acute TrkB inhibition, BTN still failed to act as an adjunct therapy. The expression level of NKCC1a was not significantly altered regardless of the treatment paradigm or anti-seizure efficacy, further supporting the importance of KCC2 rather than NKCC1 in regulating Cl− gradient and modulating seizures. BTN has also been reported to have poor brain bioavailability and short half-life. However, recent studies evaluating the efficacy of a BTN pro-drug designed to have improved brain bioavailability have reported no clear anti-seizure effect. BTN also has been shown to have non-safety issues associated with ototoxicity detected in the NEMO trial, adding to an unfavorable risk-benefit ratio as an adjuvant in neonates. NKCC1 serves a critical function in the circuit formation during early development, and is also expressed systemically. The long-term side-effects to blocking NKCC1 function during development, although not fully investigated, indicate potential pitfalls. In this study, transient inhibition of BDNF-TrkB pathway with a single dose of ANA12 allowed for efficacious treatment of PB-resistant seizures by preventing degradation of KCC2 in a model where BTN was shown to be inefficacious (Example 2, Kang et al., 2015). The goal of preventing KCC2 degradation was to help maintain the developmental expression profile of KCC2 and prevent the emergence of refractoriness. Helping maintain KCC2 function during ischemia or preventing insult-related KCC2 degradation during development may have the additional potential benefit of preventing long-term co-morbidities associated with the transient loss of KCC2 function during this critical period.

Conclusion

This study reports the successful rescue of PB-resistance associated with the rescue of KCC2 degradation in a model of neonatal ischemic seizures. Pre-clinical studies of neonatal seizures utilizing various translational models have reported: a) differential alteration of KCC2 expression, and b) differential severity of the seizure burdens in response to various seizure induction methods. The main findings of this study suggest a critical association between the anti-seizure efficacy of GABA-agonists and post-ischemic KCC2 degradation. An ongoing debate in clinical management of neonatal seizures is whether they can independently harm the developing brain and how aggressively do they need to be managed?, When compared to the results from other pre-clinical models, studies in this model suggest that the etiology and severity of neonatal seizures dictate their deleterious effects. Therefore, severe seizure burdens commonly reported in HIE may independently cause KCC2 degradation that leads to the emergence of refractory seizures. This study highlights the potential of KCC2 pharmaco-modulation as a novel therapeutic strategy in treating PB-resistant seizures in neonates. The non-efficacy and safety issues that have arisen from the previous strategy of antagonizing NKCC1 using BTN as an adjunct therapy in HIE was based on results using non-ischemic pre-clinical models. The novel approach proposed here uses a translationally relevant pre-clinical model for HIE with comparable seizure burdens which also demonstrates non-efficacy of BTN for ischemic seizures. The model therefore, highlights the importance of methods of seizure induction and associated seizure burdens in pre-clinical modelling.

Example 2

Age- and Sex-Dependent Susceptibility to Phenobarbital-Resistant Neonatal Seizures: Role of Chloride Transporters Ischemia in the immature brain is an important cause of neonatal seizures. Temporal evolution of acquired neonatal seizures and their response to anticonvulsants are of great interest, given the unreliability of the clinical correlates and poor efficacy of first-line anti-seizure drugs. The expression and function of the electroneutral chloride co-transporters KCC2 and NKCC1 influence the anti-seizure efficacy of $GABA_A$-agonists. To investigate ischemia-induced seizure susceptibility and efficacy of the $GABA_A$-agonist phenobarbital (PB), with NKCC1 antagonist bumetanide (BTN) as an adjunct treatment, we utilized permanent unilateral carotid-ligation to produce acute ischemic-seizures in postnatal day 7, 10 and 12 CD1 mice. Immediate post-ligation video-electroencephalograms (EEGs) quantitatively evaluated baseline and post-treatment seizure burdens. Brains were examined for stroke-injury and western blot analyses to evaluate the expression of KCC2 and NKCC1. Severity of acute ischemic seizures post-ligation was highest at P7. PB was an efficacious anti-seizure agent at P10 and P12, but not at P7. BTN failed as an adjunct, at all ages tested and significantly blunted PB-efficacy at P10. Significant acute post-ischemic downregulation of KCC2 was detected at all ages. At P7, males displayed higher age-dependent seizure susceptibility, associated with a significant developmental lag in their KCC2 expression. This study established a novel neonatal mouse model of PB-resistant seizures that demonstrates age/sex-dependent susceptibility. The age-dependent profile of KCC2 expression and its post-insult downregulation may underlie the PB-resistance reported in this model. Blocking NKCC1 with low-dose BTN following PB treatment failed to improve PB-efficacy.

Introduction

Neonatal seizures are the most frequent clinical manifestation of central nervous system dysfunction in newborns, with an incidence of 1.5-3.5/1000 in term newborns, and an incidence as high as 10-130/1000 in preterm newborns. Ischemia is a major cause of neonatal seizures and first-line anticonvulsant pharmacotherapy by commonly used anti-seizure drugs like PB often proves insufficient. Both animal-model and human studies suggest that neonatal seizures themselves may worsen brain injury, decrease the threshold for subsequent seizures, and result in poor long-term neurological co-morbidities. Electroclinical dissociation is now a fairly well-accepted concept in human neonates, wherein GABA agonists are able to block the clinical manifestations of seizures; however, as displayed with electrographic monitoring, the brain continues to seize.

Early in development, the depolarizing $GABA_A$ ergic signaling that is instrumental in normal neuronal differentiation and migration has been shown to be responsible for the inefficacy of $GABA_A$ agonists like PB, as an anti-seizure agent. Therefore, cation chloride co-transporters, specifically NKCC1 and KCC2, could be used as potential targets for novel anti-seizure and anti-epileptogenic treatments. NKCC1 is expressed in neurons and astrocytes throughout the brain, systemically in the kidney and inner hair cells of the ear, and is robustly involved in early neural development. The co-transporter KCC2 is CNS-specific predominantly in neurons and has a developmental expression profile that increases exponentially during the third trimester and continues to increase postnatally with advancing age.

BTN, a potent NKCC1 antagonist that has been used as a diuretic in newborns, was also shown to be effective in reducing kainic acid-induced and hypoxic seizures in neonatal animals by blocking NKCC1 especially when used in combination with PB. BTN later became the focus of clinical trials to test its efficacy in seizing neonates with hypoxic ischemic encephalopathy. However in pre-clinical studies, the anti-seizure effect of BTN has been shown to depend on the experimental model. BTN enhanced, suppressed, or had no effect on paroxysmal activity in vitro in different models, none of which modeled ischemia. Additionally, a recent study showed that kainic acid-induced seizures increased the surface expression of KCC2, shifting $E_{(GABA)}$ close to the adult levels. However, under ischemic conditions, a substantial neuron-specific downregulation of KCC2 expression has been reported, which was also detected in our mouse model of neonatal ischemia. Such discordant model-specificity in the post-injury KCC2 expression may significantly alter the efficacy of drugs that depend on the Cl⁻ gradient for their anti-seizure effects. In new developments, the European clinical trial has recently been terminated for non-efficacy of BTN with associated ototoxicity following hypoxic ischemic encephalopathy (HIE) induced seizures in neonates.

This study utilized cerebral ischemia alone to induce acute ischemic seizures in the CD1 mouse strain, and investigated the following: 1. Quantitative analyses of EEG recordings of early post-stroke events at P7, P10, and P12 to determine the acute age-dependent seizure susceptibilities and seizure burdens following ischemia. 2. Response of the ischemic seizures to standard anti-seizure agent PB, as well as novel agent BTN at doses similar to the clinical trials, to evaluate for the first time, the effect of the NKCC1 blocker BTN, as an adjunct in a model of acute ischemic seizures. 3. Effect of neonatal ischemia on the developmental expression profile of KCC2 and NKCC1.

Materials and Methods

Figure 12:
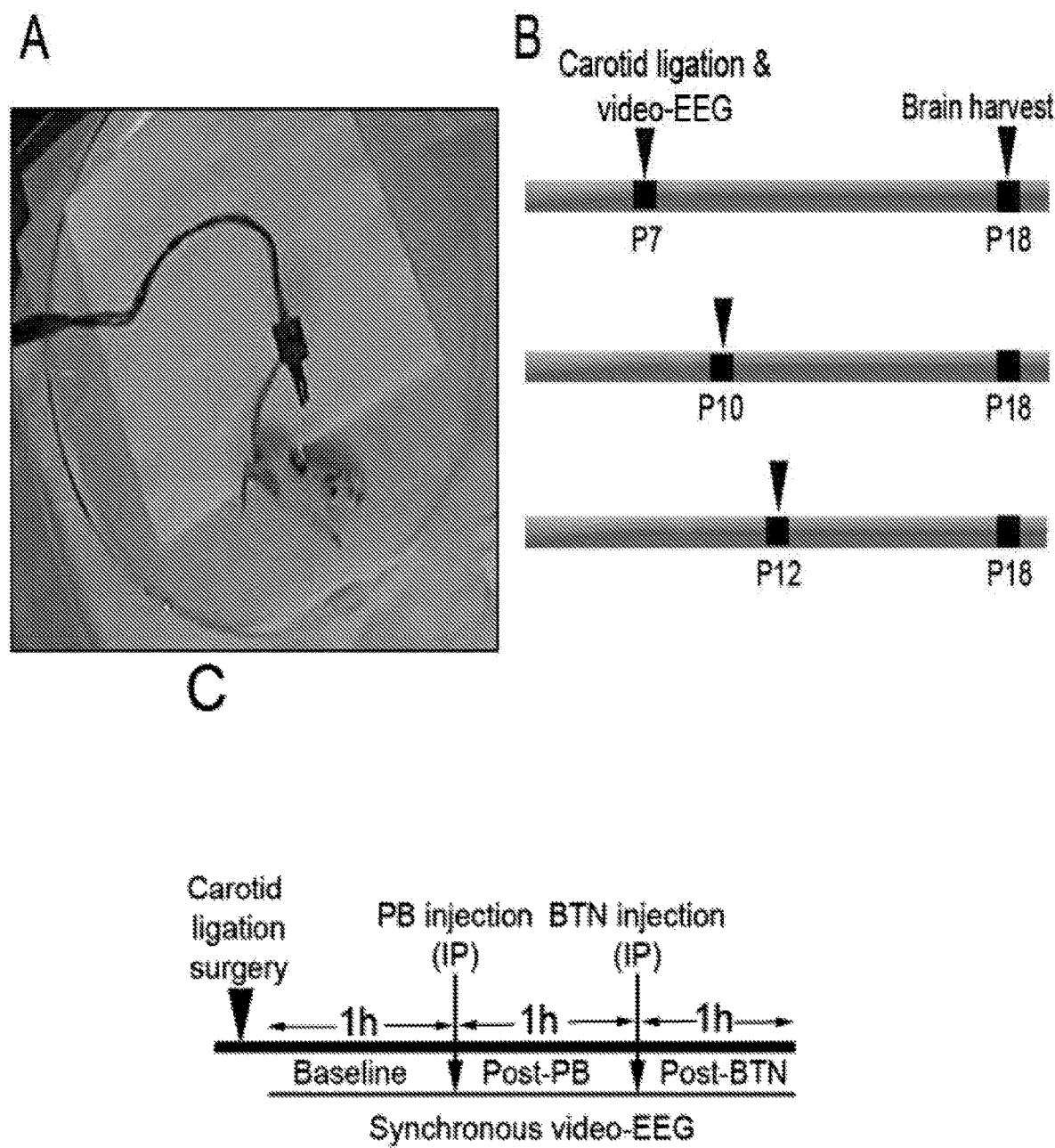
FIG. 12. A. Representative video-frame from a ligated pup having an ischemic tonic-clonic seizure. B and C. Schematics of the time-line and experimental design.

Experimental design. This study was carried out in strict accordance with the recommendations in the Guide for the Care and Use of Laboratory Animals of the National Institutes of Health. The protocol was approved by the Committee on the Ethics of Animal Experiments of the Johns Hopkins University (Permit Number: A3272-01). All surgery was performed under isoflurane general anesthesia, and all efforts were made to minimize suffering. All litters of CD1 mice were purchased from Charles River Laboratories Inc. (Wilmington, Mass.). Newly born litters of pups arrived at postnatal 3 or 4 days old, and were allowed to acclimate. Animals were housed in polycarbonate cages on a 12 h light-dark cycle and food provided ad libitum. Ninety two pups from 12 litters were included in the video-EEG study (n=48 male and n=44 female). The susceptibility to ischemic seizures was tested at 3 developmental ages i.e., 7, 10 and 12 days old CD1 pups (n=80 ligated and 12 shams). The experimental paradigm is depicted in FIG. 12. The pups underwent permanent ligation and sham surgeries followed by 3 h of EEG recording each, as described in methods (total pups=92 of which ligates P7=29, P10=24 and P12=27 and sham P7=5, P10=4 and P12=3; see Table 2). From the ligated group of pups (total n=80), the ligated-control pups also underwent 3 h EEG recordings to evaluate natural progression of ischemic seizure burden over the duration of treatment efficacy evaluated in this study (total pups n/n=26/80, P7=8, P10=9 and P12=9). Following ligation, the ligated-treated group of pups [total pups n/n=54/80; P7=20 (13 male & 7 female); P10=16 (8 male & 8 female) and P12=18 (9 male & 9 female)] were used to evaluate every baseline EEG (i.e., $1^{st}$ h of recording) that was then compared to post-PB ($2^{nd}$ h of recording) and post-BTN ($3^{rd}$ h of recording) EEGs. Since the severity of stroke-injury and seizure varies between pups, the baseline EEG of each pup served as an important internal control. Additionally, since the exact time-point of onset for ischemia in human neonates is not known and may not be a single massive event, the 1 h of non-treatment also served as an important delay expected in the treatment of neonatal seizures that are detected hours after stroke in humans. There was an age-dependent mortality associated with survival to age P18 following the ischemic seizures in this study [i.e.; 8 out of 29 pups at P7 (2 males and 6 females); 6 out of 24 pups at P10 (3 males and 3 females); and none at P12].

Surgical procedure for ischemic insult and electrode implantation. Animals were anesthetized with 2% isoflurane. The right common carotid artery was permanently double-ligated with 6-0 surgisilk and the outer skin closed with 6-0 monofilament nylon to induce ischemia (i.e.; ischemia was induced by unilateral common carotid ligation alone. Unlike other rat models commonly used for neonatal stroke, no global hypoxia is needed to induce acute ischemic seizures). Since the ligated carotid is not transected in our model, the intact pulsating carotid artery with silk ligatures can lead to reperfusion over time in this model. The constrictive efficacy (which drops cerebral perfusion to 40% or less) of the silk ligatures is known to diminish, due to the loss of their tensile strength in-vivo against the pulsating artery as a function of time. Sham-control animals were treated identically except for the carotid ligation, and did not seize (not shown). The animals were then implanted with three sub-dermal EEG electrodes (1 recording, 1 reference, and 1 ground) on the skull overlying the parietal cortex using bregma as a reference. Scalp wire electrodes made for sub-dermal use in humans (IVES EEG; Model # SWE-L25-MA, USA) were implanted, sub-dermally fixed with adhesive, in the pups. The suggested spacing for human scalp electrodes is 5-8 mm, which allows for optimal acquisition of EEG signal from mouse brains. In this study, the recording and reference electrodes were implanted less than 1 cm apart. Pups were then allowed to recover from anesthesia in a 36° C. isothermal chamber for 3 h recording of video-EEG (FIG. 12). At the end of the recording session, the pups were returned to the dams after removal of the sub-dermal electrodes and application of local anesthetic medication.

In vivo synchronous video-EEG recording. After the completion of the surgical procedures (i.e.; ligation+electrode implantation (8 min+8 min~16 min total), the EEG recordings were initiated after the pups recovered from anesthesia. Bumetanide (0.1-0.2 mg/kg dissolved in 100% alcohol, aliquoted and stored at −20° C.; protocol similar to previous study, phenobarbital (25 mg/kg dissolved in 0.9% sodium chloride, made on the day of experiment), or 0.9% sodium chloride was injected intraperitoneally (IP) after baseline post-stroke EEGs were recorded (FIG. 12C). Since these experiments were also designed to test BTN-efficacy as an adjunct therapy to PB (based on the currently recruiting clinical trials), ligated mice underwent one of two regimens: 1) Treatment with saline only at 1 h and 2 h post-surgery; 2) Treatment with PB at 1 h and BTN at 2 h post-surgery. The treatment regimen of BTN before PB or BTN without PB was not relevant to this translational design. Pharmacokinetics of PB and BTN additionally supports our treatment regimen, because PB is a long acting drug even in immature rodents [half-life ~15 h whereas BTN has a very short half-life of <30 min]. Data acquisition was done using PAL-8400 software with synchronous video capture (Pinnacle Technology Inc.). The data acquisition and conditioning system had a 14-bit resolution, sampling rates of 500 Hz, high pass filters of 0.5 Hz and low pass filters of 1 kHz. The files were stored in .EDF format and scored in real time using the review and scoring software package. Manual scoring of all EEG files was done blinded to treatment protocols by simultaneously scoring EEG traces and the synchronous video in real time. Seizure burden scoring was done on EEG with sampling rates of 400 Hz that had a pre-amplifier gain of 100. The filters of 1 Hz high-pass and 60 Hz low-pass were used to remove ambient noise, and the binning was done in 10 sec intervals. Seizures were defined as electrographic ictal events that consisted of rhythmic spikes of high amplitude, diffuse peak frequency of ≥7-8 Hz (i.e.; peak frequency detected by automated spectral power analysis) lasting more than 6 seconds. Short duration burst activity lasting <6 seconds (brief runs of epileptiform discharge) was not included for seizure burden calculations in this study.

Behavioral seizure scoring after EEG seizure detection. After an EEG seizure was detected, its time and duration of occurrence were noted, and the synchronous behavioral activity recorded on video was scored according to a seizure rating scale modified for mouse pups from a previously reported scale used for adult mice. Behavioral seizures recorded on video for EEG-identified seizures (FIGS. 13 A, B and C) were scored as follows: 0=motionless/inactive; 1=flexor spasms; 2=jittery movements; 3=repetitive grooming/scratching, circling towards side of ischemia, with head bobbing; 4=limb clonus, unstable posture; 5=mice that exhibited level four behaviors for >30 seconds or with loss of posture; and 6=severe tonic-clonic behavior with inability to regain loss of posture. After video-EEG recording, the mice were returned to the dam and littermates. Electrographic seizures associated with grade 0-2 behaviors were grouped as non-convulsive seizures and grade 3-6 behaviors were graded as convulsive seizures.

Histology. All animals were anesthetized with chloral hydrate (90 mg/ml; IP) before being transcardially perfused with saline and 10% formalin in phosphate buffer (pH 7.4). The whole brain was removed and submerged in the same fixative. The brains were cryoprotected by first immersing in 15% sucrose for 24 h, followed by 30% sucrose for 24 h. The brains were rapidly frozen using dry ice and placed in −80° C. storage. Coronal brain sections (40 μm thick) were cut on a cryostat in serial order to create 5 series of sections and mounted on super frost plus glass slides. One series of sections from the EEG recorded pups was cresyl violet (CV) stained to quantitate ischemia injury using a previously described method of computer-assisted comparison of brain tissue area in ipsilateral versus contralateral hemispheres of fixed CV stained mouse brain sections (i.e., Basic MCID). Stroke injury severities were quantitated at P18 for all brains processed for CV (n=49/80; P7=15, P10=15 and P12=19) to compare differences in infarct injury evolution between age groups. The remaining brains from study were fresh frozen for western blot analysis.

Immunohistochemistry with triple labeling: Serial sections from frontal and parietal cortex and dorsal hippocampi from a separate cohort of naïve CD1 pups aged P3 to P22 were labeled with neuronal marker NeuN (1:100, Chemicon International; Catalog # MAB377) and then processed for double labeling with NKCC1 [1:100, Chemicon International: detecting 22 amino acid peptide sequence near the C-terminus (exon 21); Catalog #AB3560P] and KCC2 (1:200, Upstate: targeting N-terminal His-tag fusion protein corresponding to residues 932-1043; Catalog #07-432). The NKCC1 antibody used in this study is similar to those used in related published literature and is incapable of detecting NKCC1b, due to the post-transcriptional splicing of exon 21 that overlaps with the targeted epitope site for the antibody. Currently no pan-NKCC1 (i.e.; splice isoforms a and b) antibodies are available. To block nonspecific binding, sections were first incubated for 1 h at room temperature (RT) in a solution containing 0.2% Triton X-100 and 10% normal goat serum in PBS (Invitrogen). The sections were incubated with primary antibodies overnight at 4° C. After 3×10 min wash in PBS, slides were incubated at RT with secondary antibodies (Alexa flour 488 and 594). After secondary antibody incubation, sections were washed 3×10 min in PBS and cover-slipped with an anti-fade medium for further image processing (Axiovision, Zeiss). Confocal microscopy of FV 1000 system with Olympus IX81 inverted microscope stand was used to acquire images of immuno-stained sections. Z-stack images with 5 um step-size for bilateral cortices was obtained from coronal sections cut at 40 um thickness. The Z-stacks were fused to obtain the final images.

Western blots. All animals for immunochemical characterizations were anesthetized with chloral hydrate (90 mg/ml; IP) before being transcardially perfused with ice-cold saline. The whole fresh brains were removed, separated into left and right cerebral hemispheres and frozen in liquid nitrogen and stored at −80° C. in preparation for further processing. Brain tissue homogenates were made and suspended in RIPA buffer containing one Complete Mini, Ethylenediaminetetraacetic acid (EDTA)-free protease inhibitor cocktail tablet (Roche Indianapolis; Catalog #04693159001) per 10 mL of buffer. Total protein amounts were measured using the Bradford protein assay (Bio-Rad) and samples diluted for equal amounts of protein in each sample. 50 ug of protein samples were run on 4-12% gradient SDS gels (Bio-Rad) and transferred onto polyvinylidene difluoride (PVDF) membranes. Membranes were blocked for 1 h in odyssey buffer before overnight incubation in primary antibodies, NKCC1 and KCC2. Blots were then incubated for 1 h in secondary antibodies (Licor; IR Dye 800CW Donkey anti-Rabbit IgG: Product #926-32213 and IR Dye 680LT Goat anti-Mouse IgG: Product #926-68070). Protein bands were visualized by chemiluminescence, using the Odyssey infrared imaging system 2.1 (LI-COR biosciences). The optical density of each sample was normalized to the level of expression of the actin run on each blot, for each antibody for statistical analysis. KCC2 and NKCC1 expression profiles in ipsilateral ischemic hemispheres were normalized to contralateral non-ischemic hemispheres in the same brain homogenized samples to compare differential effects of ischemic injury in the model [n=3 for each age group represented in FIG. 18B; n=2 for each age/sex in FIG. 18C; n=3 for each time-point group shown in FIG. 19A-C; n=13 in FIG. 19D (n pooled for time-points 6-48 h post-ischemia].

Statistics. Group means for seizure severity between treated and control mice were analyzed with independent sample student's t-tests. Treatment efficacy following PB+BTN administration for seizure burdens was analyzed using repeated measures one-way ANOVAs followed by pairwise t-tests. Mauchly's test was used to confirm the equal variances of the differences detected in repeated measures ANOVA, which is known for testing a statistical assumption of sphericity. No significance detected in Mauchly's test indicates that the assumption of sphericity for the relevant F-test in repeated measure ANOVA is not violated. Non-parametric correlations among severities of infarct lesion, seizure counts, and seizure frequency (both electrographic and behavioral) were assessed by Spearman's test. Differences with p<0.05 were considered statistically significant.

Results

Age-dependent susceptibility to ischemic seizures and response to anticonvulsants.

EEG recordings in the post-ligation period (FIG. 13) revealed ictal events along with interictal spikes and non-convulsive epileptiform discharges between ictal events (i.e., short duration bursts lasting 2-5 seconds). Ictal events on EEG (i.e., lasting >6 sec) associated with video correlates where pup was seen to be motionless or inactive (grade 0) or ictal events with behavioral correlates of grade 1 or 2 [i.e.; scale 1-6] were graded as non-convulsive (since these behaviors are also seen in naïve littermates), as described in methods. The baseline acute ischemic seizures recorded in the $1^{st}$ post-ischemic hour were significantly more severe at P7 (ligated control and ligation-treated group pooled) compared to P10 and P12 (FIGS. 13D&G black bars, p<0.0001 between P7 vs. P10 and P7 vs. P12). The ligated-control group of P10 pups showed a significant decrease in the number of ictal events in the $3^{rd}$ h of EEG recording (FIG. 13E) not seen at P12.

Figure 13A:
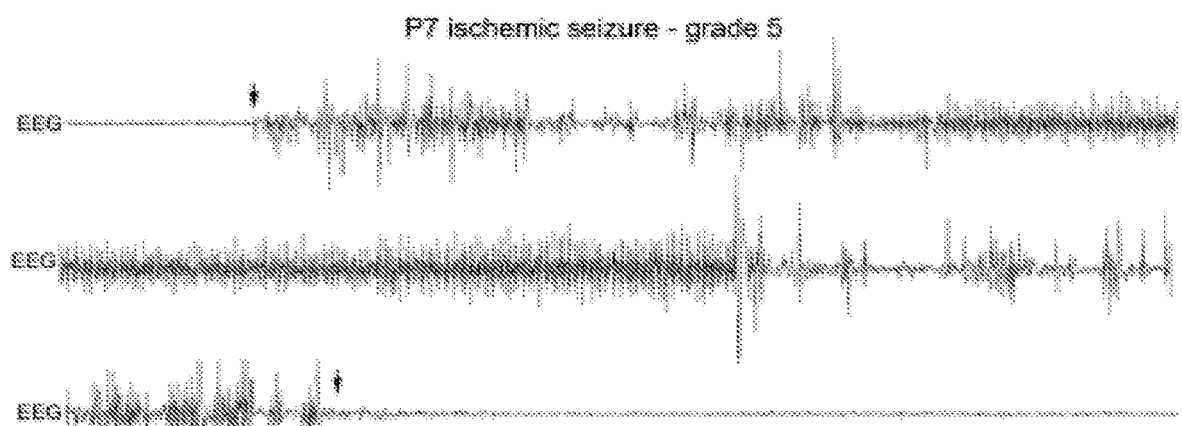
FIG. 13. Age dependent seizure burden and PB-efficacy. A-C. Representative electrographic traces of ischemic seizures recorded with sub-dermal scalp electrodes at P7, P10, and P12 and their associated behavioral grades on video. Arrowheads show the start and end of ictal events. D-F. EEG seizure burden, mean number of ictal events and ictal durations in ligated-controls that received saline injections at each hour after ligation. Seizure burden after ischemia at baseline recording was highest at P7, and was significantly more severe than at P10 (p=0.01) and P12 (p=0.03): pairwise t-test G-I. Electrographic seizure burden, mean number of ictal events and ictal durations in ligated-treated mice that received PB (1 h post-ligation) and BTN (2 h post-ligation; adjunct to PB). PB (25 mg/kg; IP) was inefficacious as an anti-seizure agent at P7. At the same loading dose, PB was significantly efficacious as an anti-seizure agent at P10 and P12. BTN as an adjunct failed to improve PB-efficacy at any age tested, and significantly blunted PB-efficacy at P10. PB-efficacy at P10 and P12 (G) was due to significant reduction in mean number of ictal events (H). Ictal durations were not significantly different at any age tested (I).
Figure 13B:
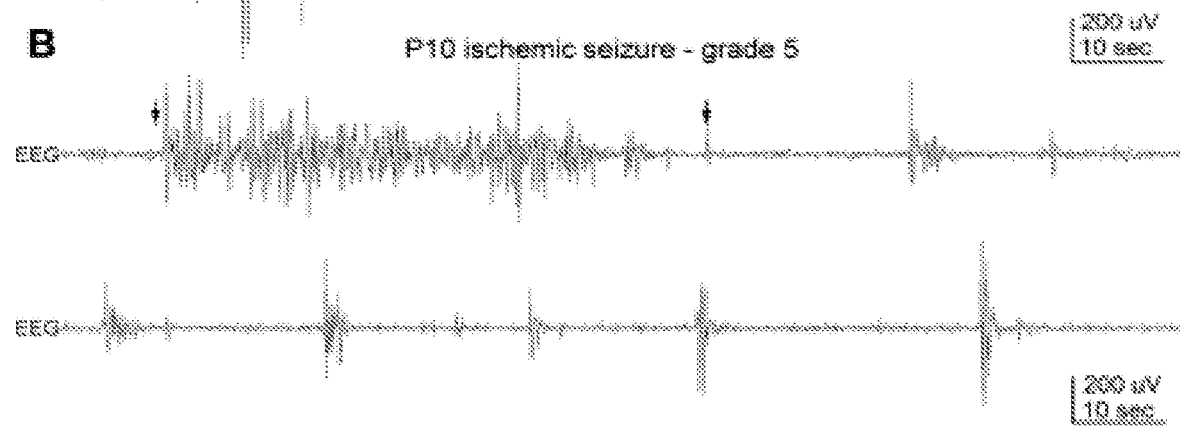
Figure 13C:
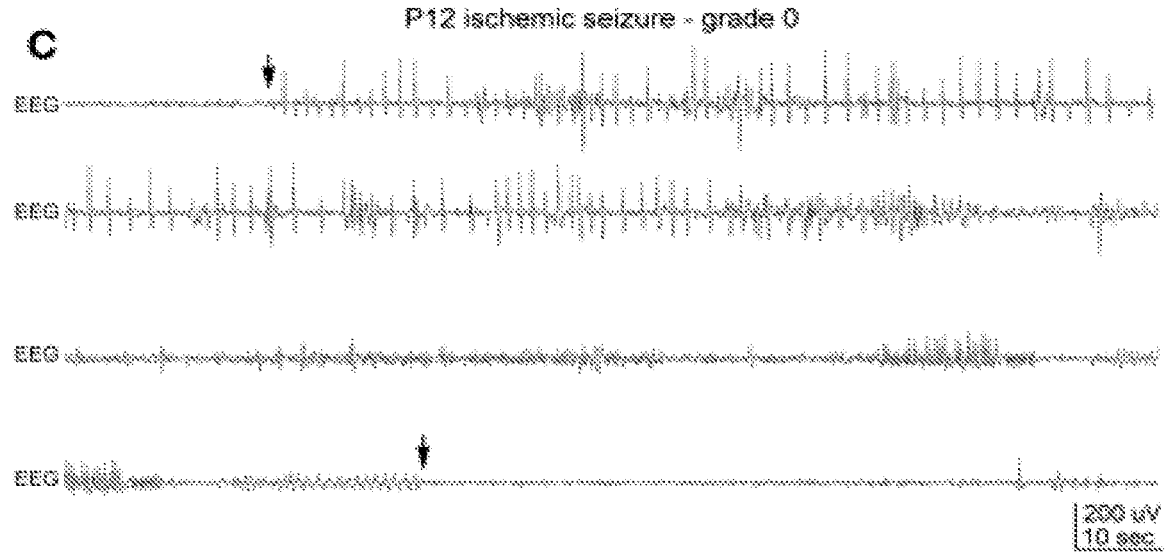
Figures 13D, 13E, 13F, 13G, 13H, 13I:
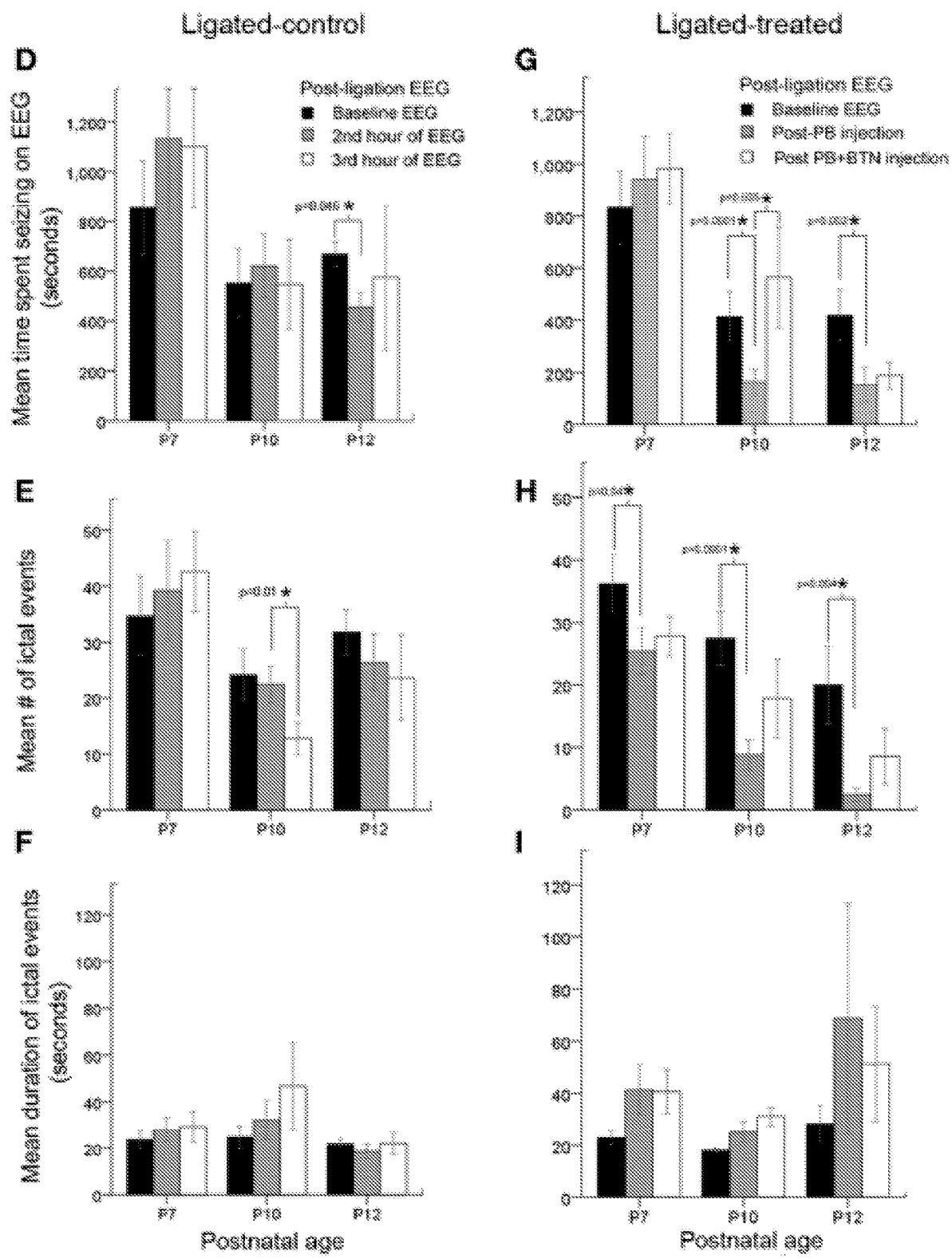

Ligated-treated pups using the same 3 h recording paradigm with PB (25 mg/kg) treatment at 1 h post-ligation and BTN (0.1-0.2 mg/kg) as an adjunct 2 h post-ligation followed similar trends for baseline EEG severities as the ligated-control group (FIGS. 13G, H and I—black bars). However, interesting age-dependent drug efficacies were detected within the treated group of pups. At P7, PB and BTN both failed to have any significant anti-seizure effect on total time spent seizing on EEG (FIG. 13G). PB, however, did modulate the ischemic seizures by significantly reducing the number of ictal events in the $2^{nd}$ h recording (FIG. 13H, p=0.04). The lack of overall PB-efficacy as an anti-seizure therapy resulted from a sustained increase in the duration of post-treatment ictal events (FIG. 13I) that was not seen in the ligated-control group (FIG. 13F). Adjunct BTN administration did not improve PB-efficacy, and the longer ictal durations persisted at P7. In contrast, at P10, PB administration 1 h after ligation, significantly reduced the seizure burden by 61% (FIG. 13G, gray bar) by significantly reducing the number of ictal events (FIG. 13H, gray bar). No significant effect on the duration of the ictal events was detected (FIG. 13I, gray bar). Follow-on BTN administration, failed to improve PB-efficacy, and additionally PB-induced seizure suppression was lost at P10 (FIG. 13G). This significant aggravation of seizures was driven by an increase in the number of ictal events (FIG. 13H) following BTN IP injection. At P12, post-PB seizure suppressions were similarly effective compared to P10. PB treatment after $1^{st}$ h significantly reduced the seizure burden by 64% due to a significant reduction in overall number of ictal events. BTN again failed to act as an effective adjuvant as it did not improve PB-efficacy (FIG. 13G).

When ligated-control and ligated-treated groups were directly compared to each other by pairwise t-tests, no significant difference was detected among the different groups for baseline seizure burden at P7 (p=0.67, black bars FIG. 13D compared to 13G), P10 (p=0.9, black bars FIG. 13D compared to 13G), or at P12 (p=0.1, black bars FIG. 13D compared to 13G). Additionally, at P7, post-treatment seizure burdens in ligated-treated group were not significantly different from the ligated-control group in the $2^{nd}$ and $3^{rd}$ hour of recordings [P=0.6 (gray bars) and 0.6 (white bars) respectively]. In contrast, at P10 and P12, post-PB (i.e.; $2^{nd}$ hour) seizure burden was significantly lower in ligated-treated group than in the ligated-control group during the same period (p=0.007 and 0.03 respectively, gray bars).

Repeated measures ANOVAs using a within subjects design for efficacious drug effects using the PB+BTN protocol in the ligation-treated group were also evaluated. At P7, Mauchly's test for sphericity was not significant (p=0.2) and within-subject drug effect was not significant (df=2, F=0.62 and p=0.55). At P10, Mauchly's test for sphericity was significant (p=0.02) and within-subjects drug effect was also significant (df=2, F=6.54 and p=0.01). The within-subjects contrast showed that the linear drug effect was not significant, but the quadratic drug effect was significant (p=0.01). At P12, Mauchly's test for sphericity was not significant (p=0.9) and within subject drug effect was not significant (df=2, F=3.690 and p=0.06). At P12, the within-subjects contrast was not significant for either the linear or quadratic drug effect. In summary, PB was a significantly efficacious anti-seizure agent both at P10 and P12 when evaluated by within-group pairwise t-tests and by independent sample t-tests compared to the ligated-control group. However at P7, PB+BTN failed to act as an efficacious anti-seizure therapy. At all three ages evaluated, BTN failed to improve PB-efficacy, but significantly blunted the PB-subdued ischemic seizures at P10. The overall lack of BTN-efficacy in the model and PB inefficacy at P7 could not be attributed to the clustering of seizures (not shown).

Figure 14:
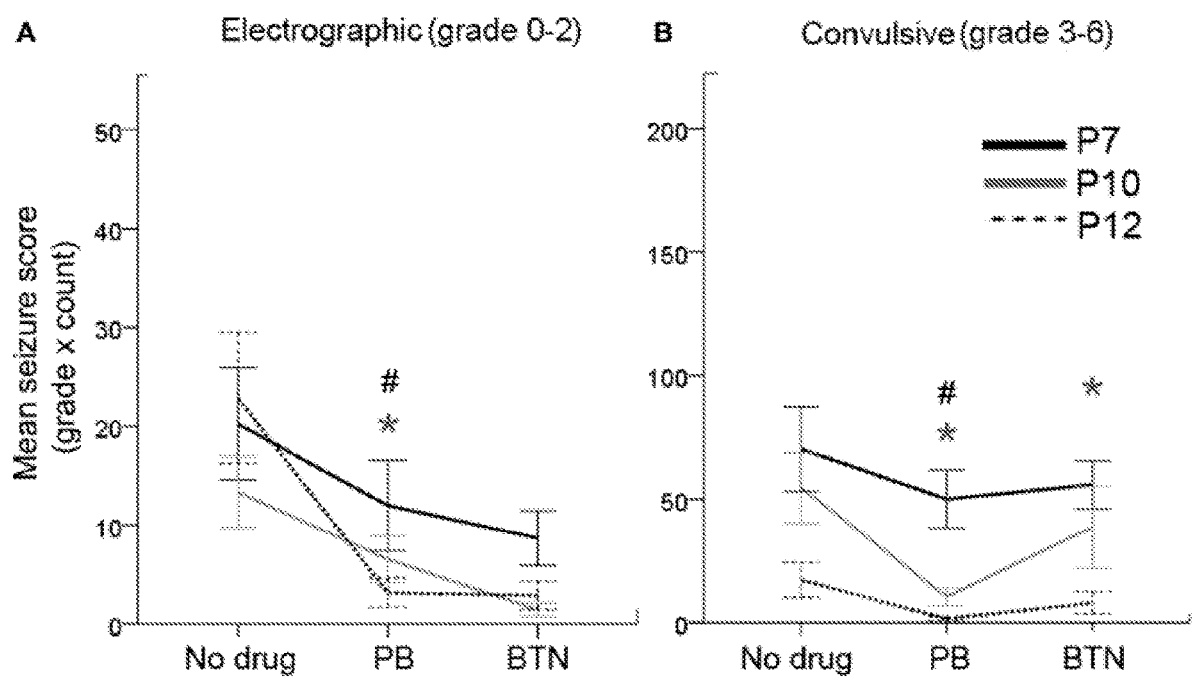
FIG. 14. Behavioral correlates of EEG seizures and PB-efficacy. Electrographic seizures (grade 0-2) occurred at all ages tested, and responded well to PB treatment at P10 and P12. This response was not significant at P7 (repeated measures ANOVA). Likewise, the convulsive seizures (grades 3-6) also showed significant PB-efficacy at P10 and P12 only with significant BTN aggravation of the convulsive seizures at P10 (repeated measures ANOVA). gray*=P10, #=P12, represent significant p-values for pairwise t-tests. Therefore, PB failed to block either electrographic or convulsive seizures at P7.

Non-convulsive vs. convulsive seizures at P7, P10 and P12. The unique advantage of synchronous video-EEG in this study was its ability to identify and quantitate the non-convulsive seizures for the entire data set. Similar to humans, neonatal seizures in rodents can be difficult to identify by behavioral parameters alone. To evaluate if the treatment efficacy was different for seizures graded as 0-2 (i.e., electrographic—ranging from inactive to behavioral correlates associated with movements not overtly convulsive—see methods) and 3-6 (i.e., convulsive), the data were grouped by these seizure scores as the sum of [grade of the seizure X count] in each epoch of the recording (FIG. 14). Electrographic seizures were detected at every age investigated in this study, and were not significantly different for the probability of occurrence during the baseline EEG (i.e., early seizures in immediate post-stroke period; FIG. 14A). Convulsive seizures showed an age-dependent decrease of occurrences for baseline EEG (FIG. 14B); however, this difference was not significant. Repeated measures ANOVAs for PB+BTN treatment efficacy showed that the within-subjects drug effects were significantly efficacious for electrographic seizures at P10 and P12 but not at P7 (P7 df=2, F=3.025, p=0.07, P10 df=2, F=5.224, p=0.03 and P12 df=2, F=9.144, p=0.004). However, for grade 3-6 seizures, the within-subjects drug effects for PB+BTN efficacy were not significant at P7 and P12 but significant at P10 (i.e.; P7 df=2, F=1.224, p=0.3, P10 df=2, F=6.604, p=0.02, and P12 df=2, F=3.262, p=0.07). For the pairwise t-tests, PB significantly dropped the scores of both electrographic and convulsive seizures at P10 and P12, but failed to curb either at P7. In contrast, follow-on BTN treatment did not add any significant therapeutic benefit on electrographic seizure scores at any age and the post-BTN increase of seizure burden at P10 was driven by significant increase in the occurrence of convulsive seizures following effective PB-driven seizure suppression.

Figure 15:
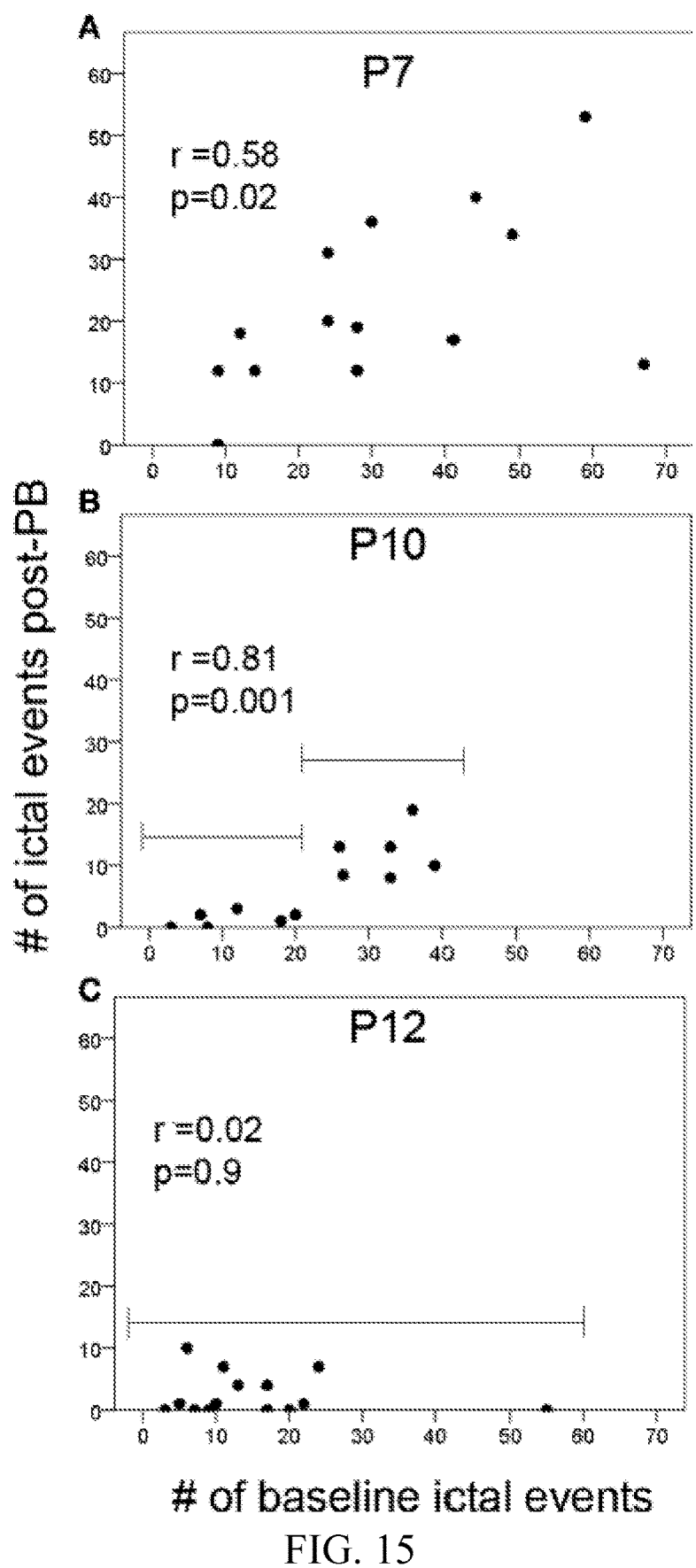
FIG. 15. Ictal events vs. PB-efficacy. A, B, and C. Correlations of the number of ictal events before treatment (i.e.; during baseline EEG recording) to the number of ictal events post-PB treatment at P7, P10 and P12. Brackets in B and C show the difference in the PB-efficacy at P10 vs. P12. Post-PB seizure suppression at P12 was consistently significant and uniform regardless of baseline seizure severities (p=0.09). In contrast, at P10 PB-efficacy was significantly dependent on the baseline seizure severity (i.e., better efficacy with lower baseline seizure loads compared to higher baseline seizure loads). Additional correlations run for baseline vs. post-PB seizure burdens showed similar results (see brackets in B); low baseline seizure burdens and PB efficacy were not significantly correlated (for baseline seizure burden <=250 sec; r=0.35, p=0.39; high baseline seizure burdens showed significant positive correlations to their post-PB seizure burdens (for baseline seizure burden>250 sec; r=0.61, p=0.03). This may indicate the potential role of the number of ictal events that have occurred before treatment on the efficacy of anti-seizure agents at P10 (p=0.001).

Correlation of baseline seizure severity to post-PB efficacy as a function of postnatal age. To evaluate whether the severity of seizure burden during baseline EEG with no drug on board contributed to the PB-efficacy given 1 h later, correlations between the numbers of ictal events during baseline recording and during post-PB recording were evaluated in the ligated-treated group (FIG. 15). At P7, there was a significant positive correlation between the number of ictal events in the $1^{st}$ and $2^{nd}$ post-PB treatment hours (FIG. 15A; p=0.02). Since PB was inefficacious at P7, this indicated that PB had no effect on overall post-PB ictal counts in each pup. Interestingly, correlations at P10 after PB-treatment compared to baseline showed a significantly stronger positive correlation than at P7 (FIG. 15B; p=0.001). Since PB was an efficacious anti-seizure agent at P10, this may indicate that the anti-seizure efficacy of PB was dependent on baseline seizure burdens (i.e.; if initial seizure burden was high, follow-on post-treatment seizure burden remained high. Additionally, FIG. 15B, group brackets representing low and high baseline seizure burdens indicate that PB was very efficacious in subduing all low seizure burdens (i.e.; ≤250 sec). This is supported by additional correlations run for baseline vs. post-PB seizure burdens which showed that low baseline seizure burdens and PB efficacy at P10 were not significant (for baseline seizure burden<=250 sec; r=0.35, p=0.39) but high baseline seizure burdens at P10 showed significant positive correlations to their post-PB seizure burdens (for baseline seizure burden>250 sec; r=0.61, p=0.03). In contrast, at P12, baselines vs. post-PB correlations were not significant (FIG. 15C). Since PB was highly efficacious at P12, this illustrates a strong anti-seizure efficacy of PB, irrespective of baseline seizure burdens.

Figure 16:
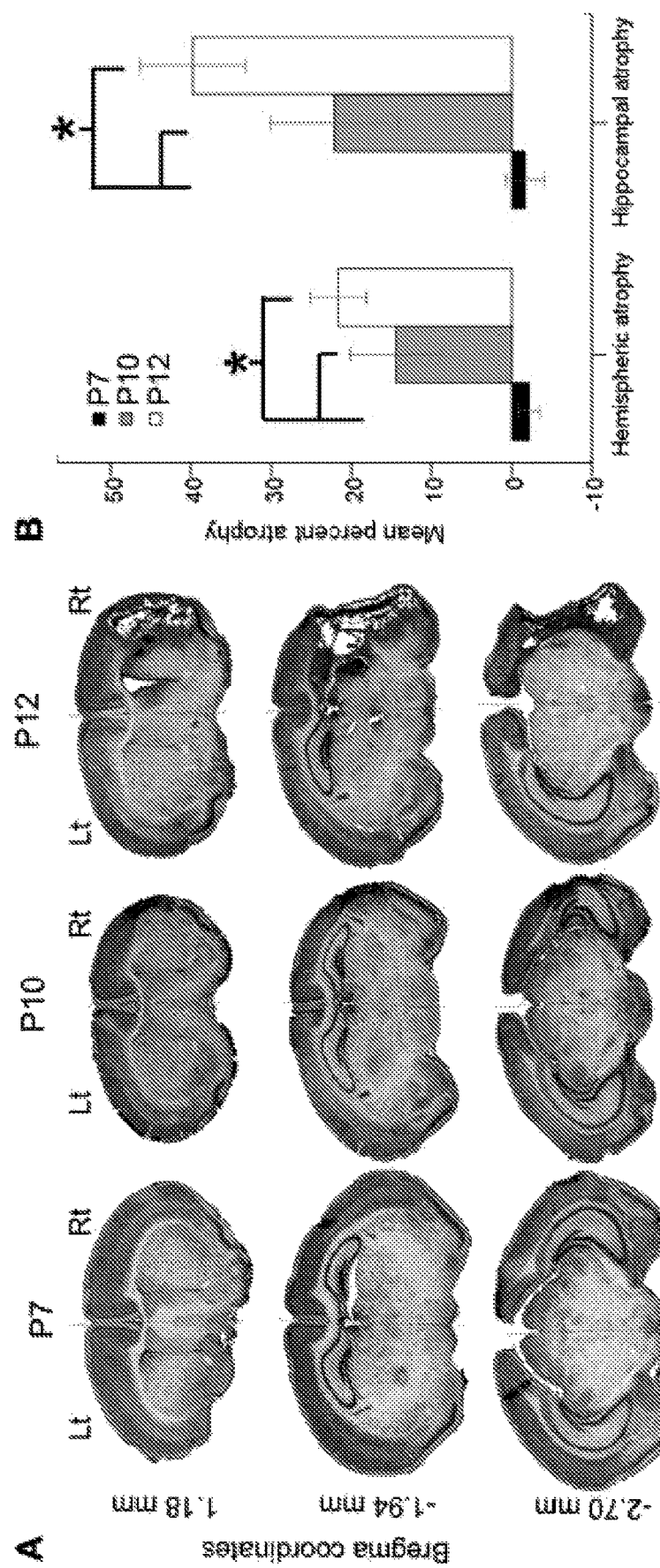
FIG. 16. Age-dependent stroke injury. A and B. Severity of the ischemic injury evaluated at P18 in ligated-treated mice. Histopathological analyses were performed on a series of coronal brain sections harvested at P18 for all the ages investigated. Post-ischemic P7 brains were significantly less vulnerable to necrotic infract injury compared to P10 and P12. Both hemispheric and hippocampal atrophies associated with stroke injury were significantly higher at P10 and P12. The stroke severities between P10 and P12 were not significantly different.

Age-dependent stroke injury. Stroke injury severities were quantitated at P18 for all brains processed for histology (n=49; P7=15, P10=15, and P12=19) and the remaining brains from study were fresh frozen for western blot analysis. Ligations at P7 did not result in a cystic infarct injury when evaluated at P18 (FIG. 16A). Although the P7 ligated brains, when harvested for western blot analysis at 6-8 h after ligation showed edema of the ipsilateral hemisphere, no measurable atrophy was detected when P7 ligated brains were harvested and processed for histology at P18 (FIG. 16). Microscopic examination also did not reveal obvious cell death in the watershed zones. Post-stroke diffuse cell death cannot be ruled out in the P7 brains however; compared to the P10 and P12 ligated pups, injury at P7 in CD1 ischemic pups may have white matter injury, which was not evaluated in this study. Overall, P7 pups showed a significant resistance to necrotic infarcts in the middle cerebral artery perfusion territory detected at P10 and P12 (FIGS. 16A and B; p=0.005 P7 vs. P10 for both hemispheric and hippocampal atrophy and p<0.0001 P7 vs. P12 for both hemispheric and hippocampal atrophy). The mean hemispheric and hippocampal atrophy in P10 were not significantly different from those in P12 (p=0.3 and 0.1 respectively).

To determine whether injury severity evaluated at P18 correlated with the seizure severity in the $1^{st}$ three hours after ischemic insult at the three ages examined, hippocampal and hemispheric atrophies were compared to the time spent seizing on EEG. No significant correlations were detected at any age. Additionally, significant positive correlations between hemispheric to hippocampal atrophy were detected for the P12 (p=0.008) ligated group at P18, which has been reported previously for ligated-control P12 mice at P40. Similar correlations were not detected for the P10 ligated-treated group. No significant correlations were detected between the severities of ischemic seizure burdens at baseline and the severity of the ischemic injury at P18, in either the P10 or P12 pups. No significant sex differences in injury severity were noted at P10 and P12 either. Since stroke injuries evolve over time, injury assessments at longer survival time-points may be more predictive of initial seizure burdens.

Age- and sex-dependent seizure susceptibilities: is KCC2 a major player?

Figures 17A, 17B:
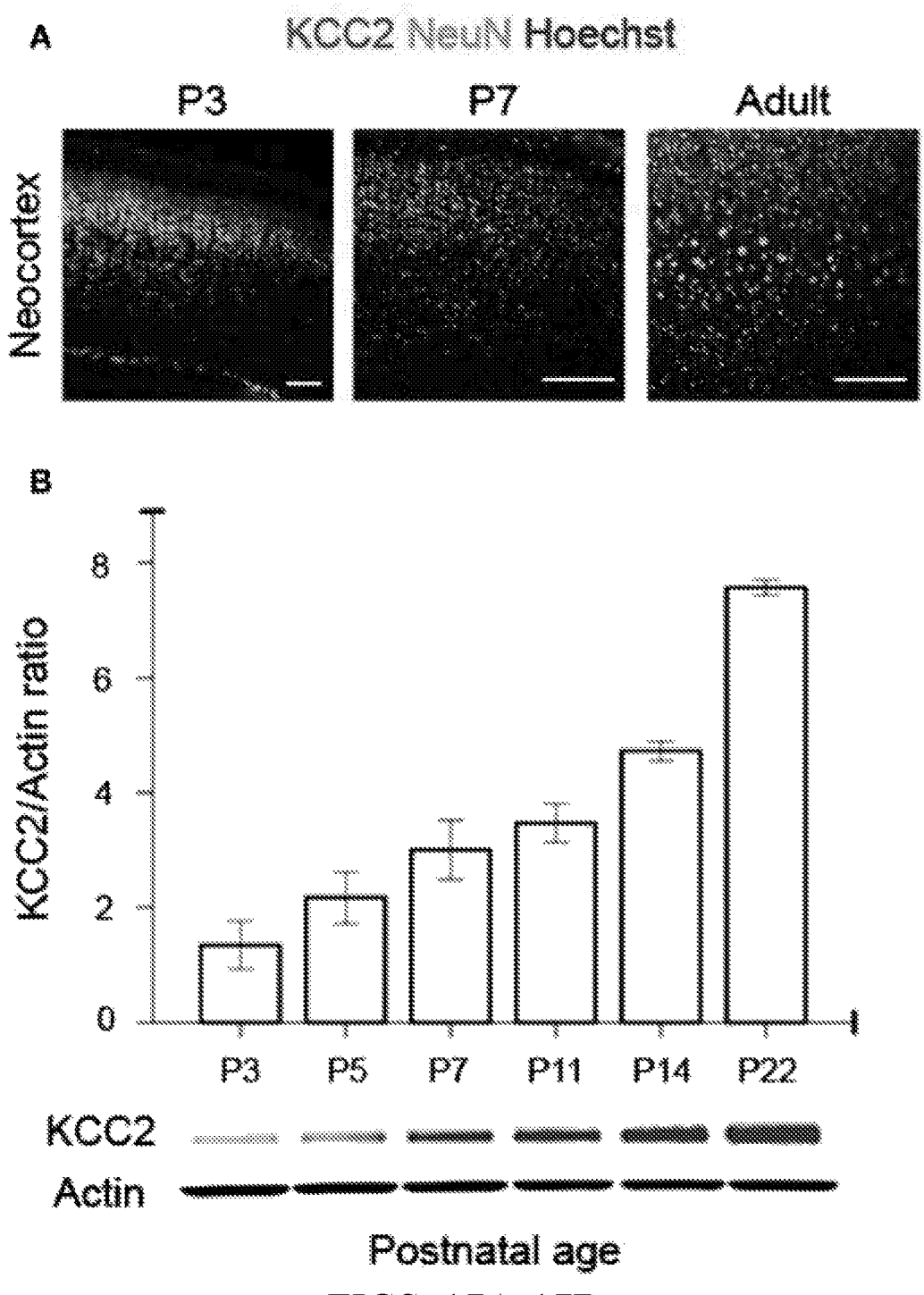
FIG. 17. Developmental profile of KCC2 expression. A. IHC for KCC2 in cortex as a function of postnatal age in naïve brains respectively (Scale bar=250 um) showed increased neuronal expression with age. B. Western blot quantitation of KCC2 expression as a function of postnatal age in naïve brains (n=3 for each age). Bar graphs show the co-transporter expression normalized to actin expression of the same brains. C. A significant sex-dependent lag of KCC2 expression was detected at P7 in naïve males compared to age-matched naïve females (p<0.05), and this dimorphism was not significant at older ages [M=male F=female (n=2 each at every age)]. Analyses for NKCC1 in the same brain samples are not shown.
Figure 17C:
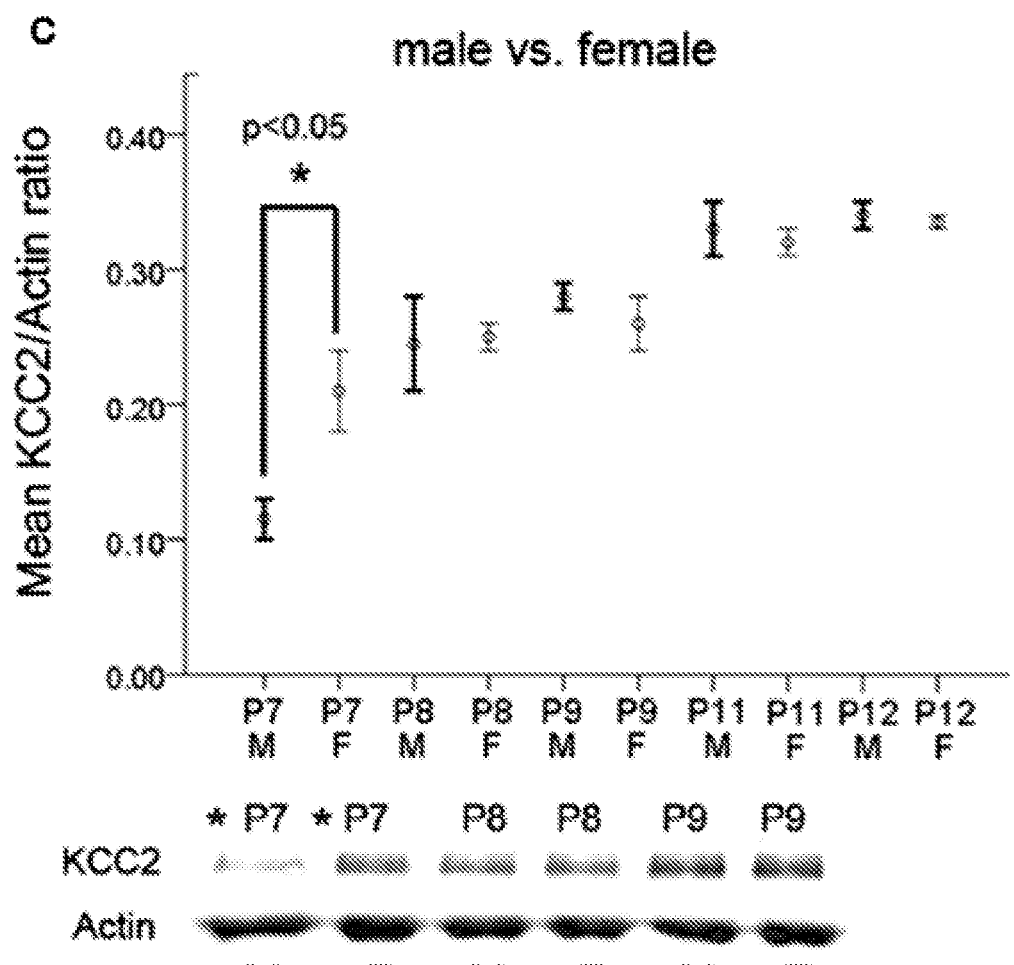
Figure 18:
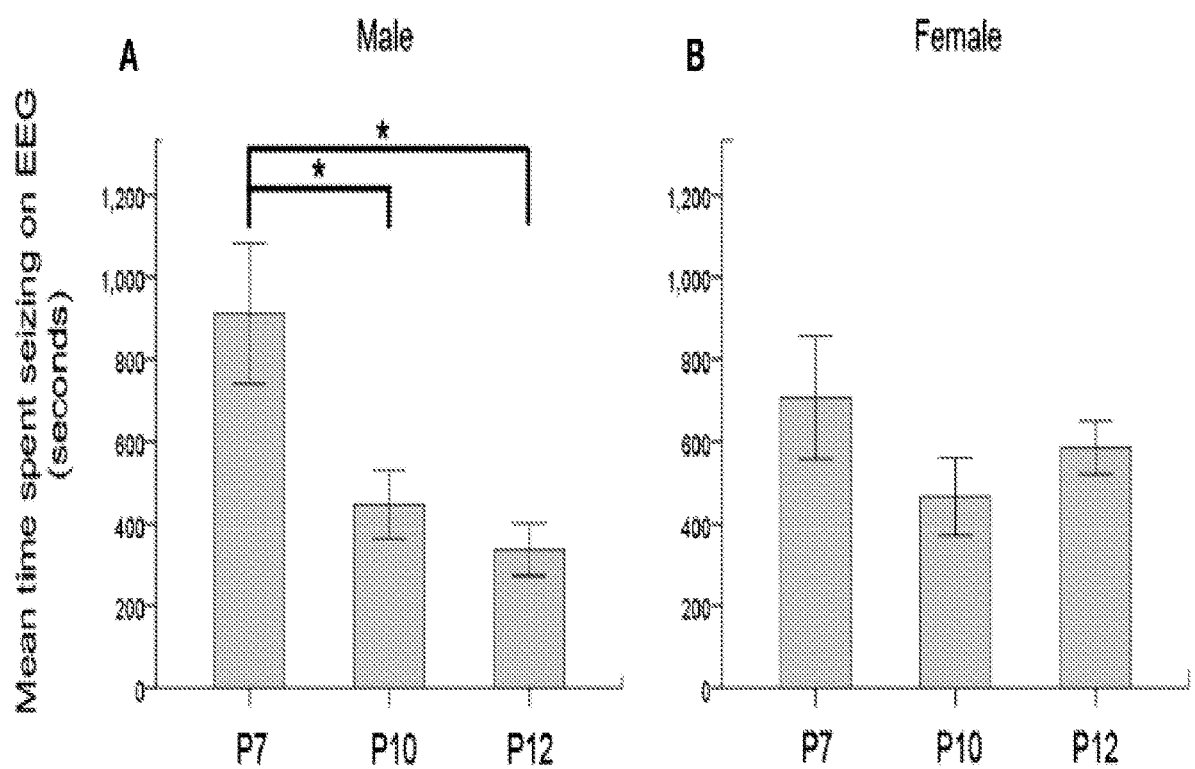
FIG. 18. Seizure severity by age and sex. A and B. Baseline seizure burdens pooled for ligated-control and ligated-treated pups showed an age-dependent susceptibility for ischemic seizures that was significant in males but not in females.

To establish an age-dependent expression profile for the CD1 mouse strain used in this model, we examined KCC2 and NKCC1 expression in naïve pup brains in ages advancing from P3 to P22 (FIG. 18A). As reported previously in both rodents and humans, we saw an age-dependent increase in the expression of KCC2 examined both by IHC and western blot analyses (FIGS. 18A and B). In contrast, NKCC1 [i.e.; detecting NKCC1a, the non-dominant spice-isoform (see methods section V.)] showed an age-dependent decrease using the same samples (not shown). Additionally at P7, a sex-dependent lag in the KCC2 expression levels was detected in naïve males compared to the age-matched females, which was not detected at older ages when examined up to the age of P12 (FIG. 18C). Similar sex-dependent maturational lags have been previously reported for males. No sex-dependent maturational lags were detected with NKCC1 (not shown). These findings, in addition to the higher susceptibility to ischemic seizures detected in P7 males (see FIGS. 17A and B) may indicate KCC2 as the major player underlying the age-dependent seizure susceptibility detected in this model.

Sex-dependent susceptibility to ischemic seizures and response to anticonvulsants.

When the baseline EEG scores (i.e.; seizure burden in the 1st hour post-ligation) for both ligated-control and ligated-treated were pooled to further analyze the effect of sex on the age-dependence of seizure susceptibility, a one-way ANOVA showed a significance for males only. Post-hoc (Bonferroni) comparisons showed P7 males to be significantly more susceptible to seizures than either P10 (p=0.04) or P12 (p=0.01) males (FIG. 17A). No significant differences were noted for females (FIG. 17B). Based on this finding, future studies need to address this sex and age-dependent ischemic-seizure susceptibility when evaluating the efficacy of PB and BTN treatment.

Figure 19A:
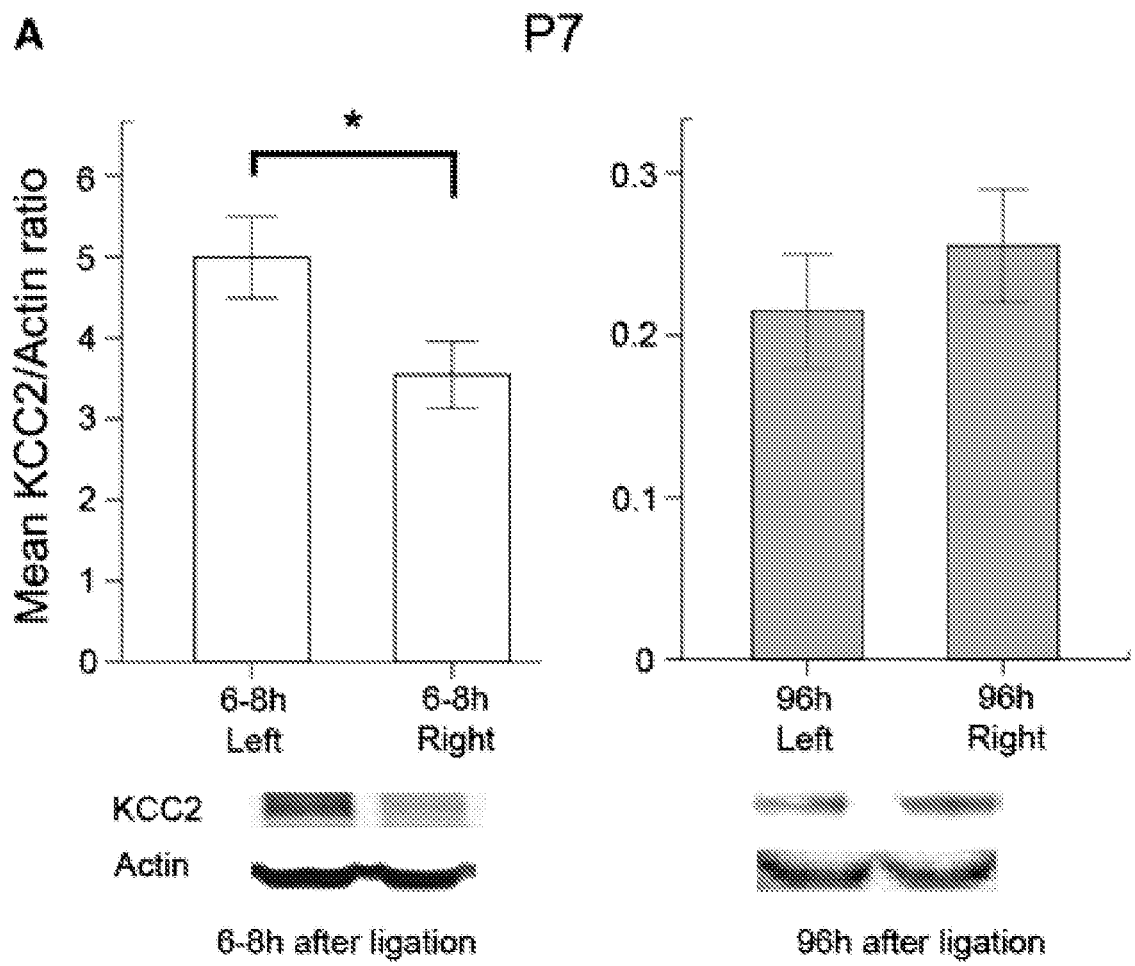
FIG. 19. Post-ischemic KCC2 downregulation. Western blot quantification of post-ligation expression of KCC2 in P7, P10, and P12 ligated pups at acute and sub-acute time-points after ischemia (n=3 each) in ipsi- and contralateral (i.e.; injured and uninjured hemispheres respectively) hemispheres; A. At P7, the significant downregulation of KCC2 detected within 6-8 h of ligation (p=0.004) showed a complete recovery by 96 h. B. At P10, KCC2 downregulation showed the same trend as at P7 at 48 h. C. P12F pups showed a significant downregulation of KCC2 at 24 h (p<0.02). D. Scatter plot of KCC2 expression levels, normalized to actin and shown as the percent of levels in their respective contralateral uninjured hemispheres. All acute time-points (6-48 h) were pooled from all three age groups (n=13). Data show that ischemia in the CD1 mice results in an acute KCC2 downregulation in the ischemic injured hemispheres with approximately 45.35% reduction in mean expression (pairwise t-test, p=0.0002; contralateral control is 100%, which is represented as a dotted gray line as a ratio of 1).
Figure 19B:
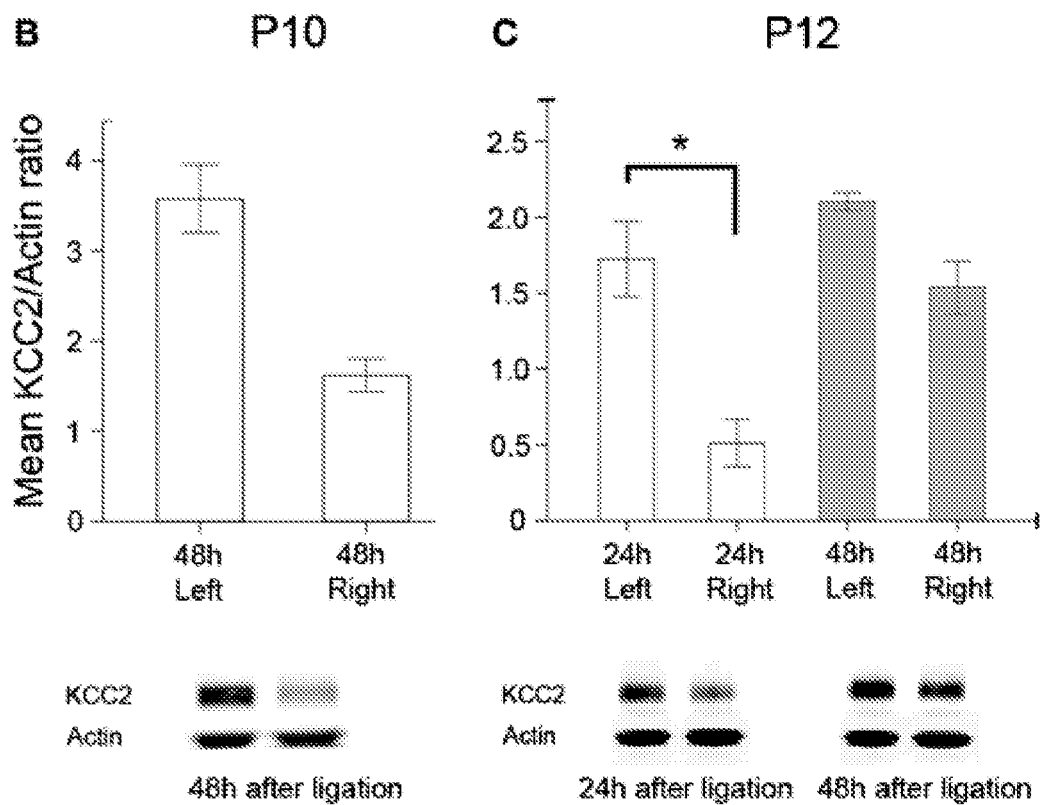
Figure 19C:
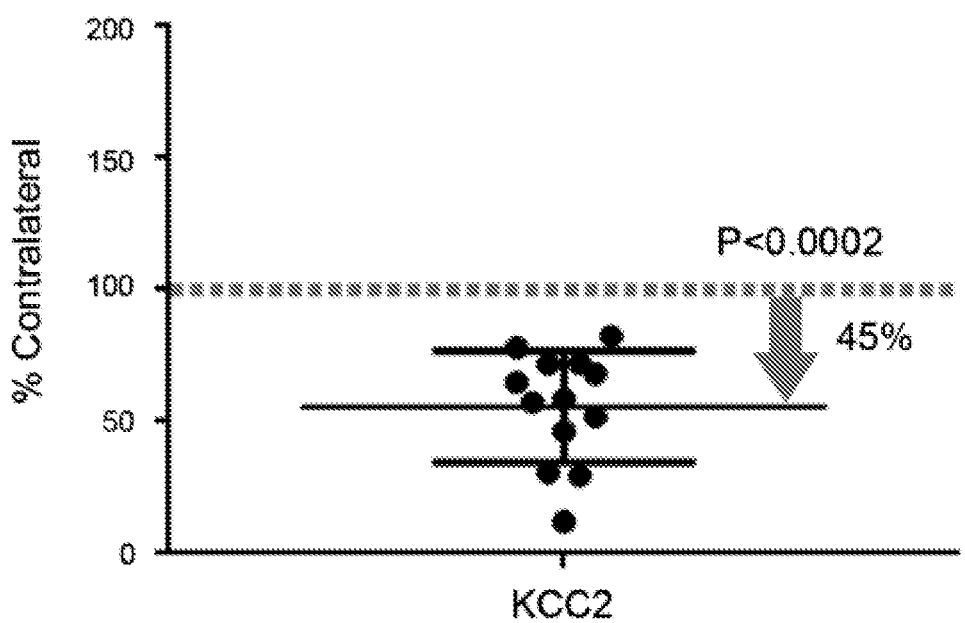

PB-resistant ischemic seizures and an acute downregulation of KCC2 expression. In this study, an acute post-ischemic downregulation of KCC2 expression was detected in the ipsilateral hemisphere compared to the contralateral hemisphere beginning from a few hours to 48 h after ischemia at all ages tested (FIG. 19A-D). The post-ischemic down-regulation of KCC2 expression in ipsilateral hemisphere was ~45% compared to uninjured contralateral hemisphere (FIG. 19D; pairwise t-test, p=0.0002). A trend towards recovery from the downregulation was also detected in the P7 age group at 96 h after ischemia (FIG. 19A-D). Although in humans NKCC1a represents a non-dominant isoform of NKCC1 splice variant, the analogous expression profiles in rodents are not known due to the current lack of a pan-NKKC1 antibody. Using the currently available antibodies, our data matched the previously published data where NKCC1 was shown to decrease with advancing age in naïve brains (not shown). There were paradoxical trends towards post-ischemic increase in NKCC1 levels in the ipsilateral hemisphere at ≤48 h in this study (not shown), as it was shown in a lesion study. Similar findings have also been noted after neonatal hypoxia-ischemia. These results indicate that neonatal ischemia significantly alters the acute and sub-acute developmental profiles of the adult-form chloride transporter KCC2; however, NKCC1 developmental expression profiles remain relatively unaltered or increased. While ischemia-related changes in cellular populations were expected with the stroke lesions, both co-transporters, KCC2 and NKCC1 would be similarly affected by these changes at the three age groups evaluated (i.e.; P7 group where no infarct lesions were seen at P18 vs. P10 and P12 where they were commonly detected; see FIG. 16). Both of these co-transporters were evaluated in the same homogenized brain samples, and KCC2 showed consistent downregulation at 6 to 48 h and recovery at 96 h. More importantly, the finding of PB-resistance at P7 and the seizure-burden dependent efficacy at P10 validates the P7-P10 CD1 mouse model of neonatal ischemia reported here as a novel tool to test the efficacy of novel anti-seizure pharmacotherapies in a clinically relevant model of seizure induction.

Discussion

This study has several salient findings to report. 1. A new mouse model of ischemic seizures that developed both primarily PB-resistant seizures at P7 and PB-responsive seizures at P10. At P10, PB-efficacy was dependent on the baseline seizure burden (i.e.; lower the seizure burden better the anti-seizure efficacy). The acute seizures recorded in the first three hours after initiation of ischemia represented a status-like seizure burden state well described for severities typically seen clinically in HIE. 2. The age-dependent seizure susceptibility after ischemia was significantly higher at P7 than both at P10 and P12. This susceptibility may represent the underlying age-dependent upregulation of KCC2 expression in maturing brains. 3. An acute and significant post-ischemic KCC2 downregulation was detected at all ages tested. The post-ischemic KCC2 downregulation catches up with the age-dependent developmental increase, representing recovery from ischemic insult within a few days. Therefore, ischemic injury significantly modulates the developmental profile of the adult-form chloride co-transporter KCC2, and thus dictates the efficacy of anti-seizure medications that follow. 4. The NKCC1 antagonist, BTN, failed to act as an adjunct in the new model for the primary PB-resistant seizures. Additionally, BTN blunted the anti-seizure efficacy of PB treatment at P10 with the follow-on treatment paradigm, by aggravating the PB-subdued seizures. Hence, NKCC1 blockage fails to rescue ischemic seizures regardless of the anti-seizure efficacy of $GABA_A$ agonists which fail at P7 but work at P10 and P12. 5. The sex-dependent seizure susceptibility detected in P7 males may correlate with the developmental lag of KCC2 expression in naïve males compared to females at that age. This lag goes away with advancing age.

Neonatal seizures, especially those associated with ischemia, are known to be transient in the neonatal period. HIE seizures also show hours of increasing seizure burdens alternating with quiet or low-seizing periods with crests and troughs during their natural temporal progression. How aggressively we treat these transient seizures, which may be severe in some cases, with drugs that may also alter the developmental profile of an immature brain, is a subject of debate. The exact time of onset of ischemia in neonates is rarely known, and clinical seizures are detected a few hours to days later. This may be due to either, a failure to detect the subtle early seizures since most of the EEG seizures are non-clinical, or a slower paced evolution of the ischemic injury. The dynamics of this evolution is however poorly understood and difficult to quantitate clinically. Recent studies that have tried to evaluate the issue are difficult to interpret with regards to evolution because the baseline seizure burdens before onset of treatment are rarely known or quantifiable without EEG. This limitation in reported clinical studies persists due to the nature of the disease and the lack of EEG data to accurately assess pre-treatment seizure burdens of non-clinical seizures. Even so, PB-inefficacy as first-line treatment is now widely reported.

Intrinsic features of immature networks make $GABA_A$-based pharmacotherapy more difficult. Following recurrent seizures, it has been shown that intracellular chloride ions accumulate, making GABA strongly excitatory. Recent research has shown that KCC2 downregulation following excitotoxic injury may underlie these findings. Developmentally, NKCC1 mediates influx of chloride ions; however, this chloride co-transporter is neither necessary nor sufficient, as these shifts of GABA polarity also occur in NKCC1 KOs. Additionally, recent study has identified two spice variants of NKCC1 in the human brain, NKCC1a [1-27] and NKCC1b [1-27 (Δ21)]. NKCC1b is the dominant splice variant in human brains, which shows an age-dependent upregulation. No reliable pan-NKCC1 antibodies, capable of detecting both variants, are currently available for reevaluating the NKCC1 data reported here (not shown) or the similar published data in animal models that may have only quantitated NKCC1a, which was shown to downregulate with advancing age. The activity-dependent downregulation of KCC2 after NMDA-induced excitotoxicity may lead to appearance of PB-resistance, and pre-clinical animal models of neonatal seizures that do not result in KCC2 downregulation may not be relevant to ischemic seizures. Reports of KCC2 downregulation in the white-matter of premature babies with white matter lesions support this hypothesis. Even in adult models of epilepsy, downregulation of KCC2 has been detected in human cortices resected for refractory seizures and in peritumoral neurons in mouse cortical slices, further confirming that KCC2 is the key player in maintaining chloride homeostasis in mature neurons. The expression profile of the co-transporters in HIE brains remains unknown and has the potential to add significant insights into pre-clinical animal modeling. Therefore, preventing KCC2 downregulation following injury may help delay the intracellular chloride accumulation during repetitive ischemic seizures and thus increase the efficacy of $GABA_A$-agonists. The critical role of KCC2 for chloride homeostasis and ultimately neuronal survival has been well established in KCC2 knockout (KO) model of in vitro and in vivo. Knockout of isoforms, KCC2a and b are lethal in mice due to respiratory failure, while KCC2b KO mice can survive up to P17, with frequent and severe spontaneous seizures. In addition, the now known role of KCC2 in spine development and cortical interneuron migration may indicate that post-excitotoxic downregulation of KCC2 may underlie the development of long-term sequelae like cognitive and behavioral deficits. In contrast, the NKCC1 KO mouse does not have spontaneous seizures, is non-lethal but deaf. Since our study showed a strong correlation between the severity of the early untreated ischemic seizures and PB-efficacy as a function of age, this animal model of PB-resistant seizures would be a useful tool to test this hypothesis further.

Using physiologic techniques, the intracellular chloride shift has been shown to be primarily due to the downregulation and internalization of the chloride exporter KCC2. It has been shown that KCC2 downregulation occurs immediately within minutes after an excitotoxic injury. This finding complements data from other studies showing that this co-transporter is highly sensitive to serine and tyrosine phosphorylation and seizures that control its turnover. The diuretic NKCC1 antagonist, BTN, has been proposed as a novel anti-seizure medication and is the basis of a current clinical trial (NEMO, FP7-EU clinical trial: and ClinicalTrials.gov; NCT00830531); however, BTN blocks seizures in some but not all models of seizures. Even with a pretreatment protocol used in a chemoconvulsant model in neonatal rats, studies have shown an age-dependent specificity of the lack of efficacy of BTN where higher doses actually decreased the latency to generalized seizures in the older pups (i.e.; P12). With the recent reports of the termination of the European clinical trial reporting BTN-inefficacy for HIE seizures associated with ototoxicity, testing higher doses of BTN seems counterproductive. The results of our experiments using a clinically relevant post-treatment protocol support these reports. In the immature brain, it is possible that the very early seizures, which occur before a significant KCC2 downregulation has begun, may be efficaciously blocked by BTN alone or as an adjunct treatment after PB. In addition, BTN as an adjunct treatment to PB may work efficaciously in neonatal seizures that are not associated with KCC2 downregulation. However, after recurrent seizures and KCC2 degradation, GABA strongly excites neurons in the immature brain, and drugs like PB that act as $GABA_A$ agonists fail to act. Similarly, our findings suggest that PB efficacy is dependent on the baseline seizure burdens specifically at P10 in our model. Our studies show that BTN fails to improve PB-efficacy when given as a follow-on treatment at P7. Our results also show that BTN can blunt PB-subdued seizures at P10. The BTN aggravation in our study following PB-efficacy may not be detected clinically, since BTN would not be administered to a patient whose seizures have responded well to PB. However, this finding is of scientific significance and deserves further evaluation to understand the underlying mechanism.

In general, the use of BTN in critically ill patients requires caution. Blocking NKCC1 function in the brain during development may interfere with critical circuit formation. BTN non-specificity as a NKCC1 antagonist and its ability to also block KCC2 at higher doses should be an additional concern in a seizing brain. The associated ototoxicity detected in the NEMO trial associated with the expression of the same NKCC1 isoform in the inner hair cells, should raise caution for all neonatologists who use BTN for its approved use as a diuretic. In a model of hypoxic seizures, the maximum concentration of BTN in the brain was estimated to be 1.2 ng/ml following an acute dose of BTN injected IP at 0.3 mg/kg. Recent review also discusses the various reasons for the low bioavailability of BTN in brain, a significant caveat to this line of pharmacotherapy. Although BTN prodrugs designed for better brain bioavailability now exist, the anti-seizure efficacies of those BTN prodrugs were recently investigated and show no clear effect. Additionally, the issue of side-effects such as diuresis and ototoxicity remain. The phenomenon of BTN aggravation of seizures reported here occurred only after PB was efficacious in subduing the ischemic seizures (not shown) in an immature brain where KCC2 is already significantly downregulated. In addition to the acute side-effects, BTN has also been shown to result in deleterious long-term effects. A significant increase in the percentage of rats having spontaneous seizures has been reported in response to the acute administration of BTN following PB in a pilocarpine model of temporal epilepsy. BTN may also attenuate the seizure-induced activation of HPA by blocking NKCC1 in periventricular neurons. However, this study was done in adult rodents, and the effect of BTN on HPA axis in immature brains is not known. Overall, further work is required to understand the potential cause of post-BTN aggravation of seizures reported in this model.

Early and effective treatment of neonatal seizures following excitotoxic insults is of course the gold standard for management; but early and efficacious treatment is not always attainable. Inability to detect the exact onset of ischemia, failure to detect subtle neonatal seizures, and the likelihood of preceding in-utero ischemic insults may lead to the early KCC2 downregulation and a lag in developmental profile that may underlie the increased seizure susceptibility and PB-resistance of the first detected seizures. Ischemia in the developing brain likely alters the expression profile of a multitude of factors that modulate transmembrane ionic gradients. This study shows that the pathology underlying the occurrence of neonatal seizures may dictate drug responses. Current clinical trials for BTN were initiated based on earlier reports of BTN-efficacy from non-ischemic models that may depend on the stable KCC2 expression following the initial insult. However, our data show that KCC2 downregulation, beginning in-utero following ischemia or possibly infection/inflammation, may make early interventions with BTN futile. In conditions where KCC2 is already downregulated before birth or lagging in the age-dependent upregulation, blocking Cl− import through NKCC1 cannot compensate for the role of KCC2 as a Cl− extruder. Additionally, we do not clearly understand the BTN-induced aggravation of seizures detected in our study that was also differentially modulated by sex. BTN half-life in rodents is short and at ~30 min, clearly less than the 1 h of seizure burden quantitated in this study. BTN aggravation, when noted, began within 5-10 min of the treatment and lasted throughout the 1 h of recording (not shown). Recent evidence of estradiol modulation of NKCC1 shows that many details of this process and its sex-dependent modulation remain to be understood. The overall age-dependent susceptibility of males to ischemic seizures in this study and the additional window period of a lag in KCC2 development in naïve brains may add to the accumulating data on male susceptibility to developmental injury and differential effects of neonatal treatments by sex.

In conclusion, this study highlights the variability of drug responses in animal models based on the mechanism by which the seizures are induced. For BTN, these model-specific outcomes have already been reported to be very variable. Dose-dependent efficacy detected for higher doses of BTN has been shown to suppress neonatal kindling when given as a pre-treatment protocol and has been proposed as a reason behind the failure of lower dose regimens reported in other models. However, pre-treatment protocols have also resulted in an aggravation of seizure onset latencies with higher doses in immature rats using chemoconvulsants. Additionally, BTN failed to work at P7 in that study which highlights the age-dependency for its efficacy. The findings of our study suggest that when KCC2 levels remain unaltered or become enhanced after kindling, such protocols may not be translationally relevant to the HIE patients being recruited in the current clinical trials where ischemia is the prominent underlying cause. This hypothesis is now supported by outcomes reported in the recently published NEMO study. The same caveat would apply to the translational value for the BTN pre-treatment paradigms that alter the chloride gradients in the naïve brains prior to insult induction in a dose dependent manner. The variable effects of BTN reported in recent literature and in this current study, highlight the need for further translational research using BTN. A recent study, Cleary et al has reported beneficial dose-dependent effects of PB+BTN pre-treatment in a rat model of hypoxic neonatal seizures. Since they also reported a significant upregulation KCC2 in hippocampus on the day of assessment of BTN treatment efficacy, these data strongly suggest that KCC2 downregulation after ischemia may be a major player in the development of PB-resistance. BTN efficacies were shown to be age- and sex-specific even within the relatively narrow age range investigated in this study. None of the pre-treatment studies noted above examined sex differences. Our results also indicate that neonatal stroke/seizures left undetected or untreated for extended periods of time alter the acute and sub-acute developmental profiles of the adult-form chloride co-transporter KCC2 such that the later seizures may become resistant to treatment with the conventional anticonvulsants that act as $GABA_A$ agonists. Prolonged seizures are also known to alter $GABA_R$ such that it reduces the efficacy of AEDs. In neonates, the transient downregulation and the developmental lag in the KCC2 expression profile may additionally result in chronic alteration of the way the immature brain is getting wired within that critical developmental window. This study shows that a novel focus on preventing KCC2 downregulation or enhancing KCC2 function following neonatal insults may be critical in guiding future approaches for treating PB-resistant seizures in neonates.

Example 3: Efficacy of KCC2 Agonist Treatment of Neonatal Seizures

Figure 20:
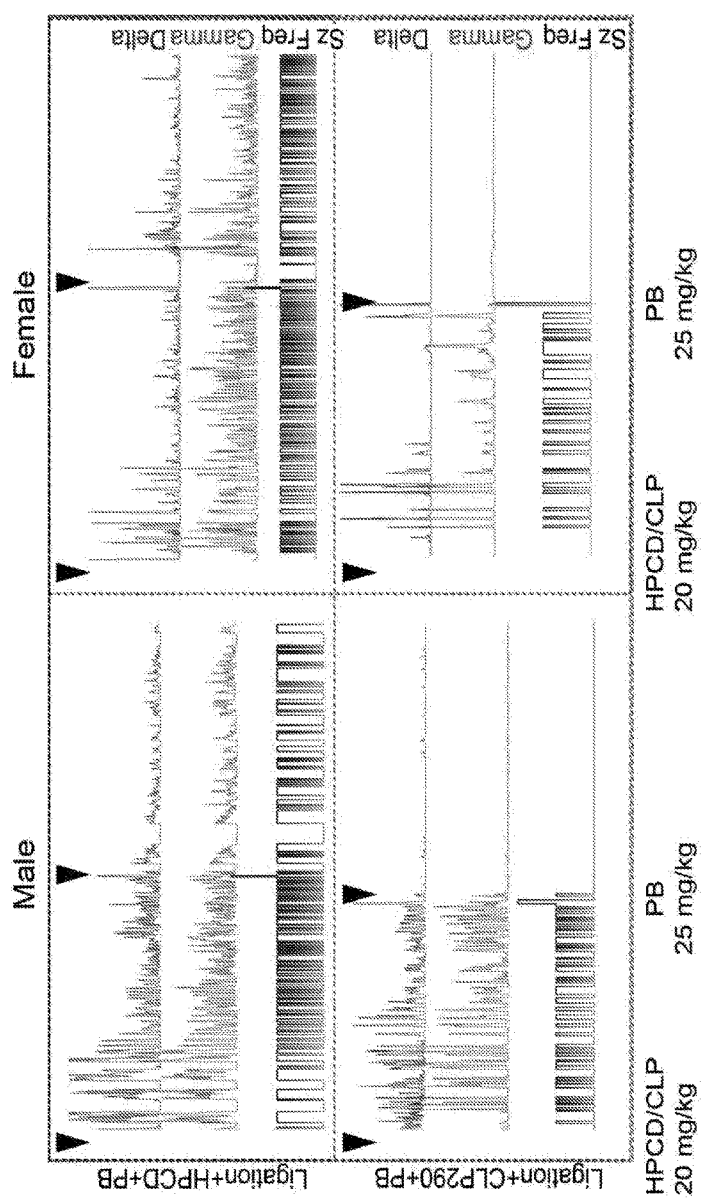
FIG. 20. Data using CLP290 (n=4) in an experimental paradigm similar to ANA-12 indicating that the KCC2 agonist can act independently as an anti-seizure agent and with PB to completely block all ischemic seizures at a 20 mg/kg dose in the model when compared to the vehicle injection (HPCD). Bottom trace in each panel shows the seizure frequency as scored by electrographic seizure activity on raw EEG in blue. Middle trace shows gamma frequency seizure burst activity on 3 h EEG and top blue trace shows low frequency activity due to movement artifacts during ischemia induced status. This finding indicates that as a KCC2 agonist CLP290 also works efficiently to not only reverse PB-resistant seizures but act as an anti-seizure agent by itself. Arrow heads indicate time of 1 hourly drug injections from start of the 3 h recording.

FIG. 20 presents data using CLP290 (n=4) in an experimental paradigm similar to ANA-12 indicating that a KCC2 agonist can act independently as an anti-seizure agent and with PB to completely block all ischemic seizures at a 20 mg/kg dose in the model when compared to the vehicle injection (HPCD). Bottom trace in each panel shows the seizure frequency as scored by electrographic seizure activity on raw EEG in blue. Middle trace shows gamma frequency seizure burst activity on 3 h EEG and top blue trace shows low frequency activity due to movement artifacts during ischemia induced status. This finding indicates that as a KCC2 agonist CLP290 also works efficiently to not only reverse PB-resistant seizures but act as an anti-seizure agent by itself. Arrow heads indicate time of 1 hourly drug injections from start of the 3 h recording.

I claim:

1. A method for rescuing phenobarbital-resistance of seizures in a neonatal patient comprising the steps of:
    a. administering to the patient an amount of N-[2-[[(Hexahydro-2-oxo-1H-azepin-3-yl)amino]carbonyl]phenyl]-benzo[b]thiophene-2-carboxamide (ANA-12) or ANA-12 in combination with [5-Fluoro-2-[(Z)-(2-hexahydropyridazin-1-yl-4-oxo-thiazol-5-ylidene) methyl]phenyl] pyrrolidine-1-carboxylate (CLP290) effective to rescue the down regulation of $K^+Cl^-$ co-transporter 2 (KCC2) expression; and
    b. administering to the patient an effective amount of phenobarbital.

2. The method of claim 1, wherein the seizure is an ischemia-related seizure.

* * * * *